US006759213B1

(12) United States Patent
St. Geme et al.

(10) Patent No.: US 6,759,213 B1
(45) Date of Patent: **\*Jul. 6, 2004**

(54) HAEMOPHILUS ADHESION PROTEINS

(75) Inventors: Joseph St. Geme, St. Louis, MO (US); Stephen J. Barenkamp, Webster Groves, MO (US)

(73) Assignee: Washington University, St. Louis, MO (US)

( * ) Notice: Subject to any disclaimer, the term of this patent is extended or adjusted under 35 U.S.C. 154(b) by 2 days.

This patent is subject to a terminal disclaimer.

(21) Appl. No.: 09/684,707

(22) Filed: Oct. 4, 2000

Related U.S. Application Data

(62) Division of application No. 08/913,942, filed as application No. PCT/US96/04031 on Mar. 22, 1996, now Pat. No. 6,200,578, which is a continuation of application No. 08/409,995, filed on Mar. 24, 1995, now Pat. No. 5,646,259.

(51) Int. Cl.$^7$ .................. C07H 21/04; C12N 15/00; C12P 21/06

(52) U.S. Cl. ................. 435/69.1; 435/320.1; 435/325; 435/252.3; 435/254.11; 536/23.7

(58) Field of Search ................. 536/23.7; 435/69.1, 435/320.1, 325, 252.3, 254.11; 424/256.1; 530/350, 300

(56) References Cited

FOREIGN PATENT DOCUMENTS

| WO | WO92/10936 | 7/1992 |
| WO | WO94/00149 | 1/1994 |
| WO | WO96/02648 | 2/1996 |

OTHER PUBLICATIONS

Sambrook et al in "Molecular Cloning A Laboratory Manual", Cold Spring Harbor Laboratory Press Inc., pp. 17.2–17.44, 1989.*
Newhard et al, Eur. J. Biochem 146:597–603, 1985.*
Wilson et al., Nature 368:32–38, 1994.*
Skurnik et al, Mol. Microbiol. 3:517–529, 1989.*
Barenkamp et al., "Genes Encoding High–Molecular–Weight Adhesion Proteins of Nontypeable Haemophilus Influenzae are Part of Gene Clusters," *Infection and Immunity*, 62(8):3320–3328 (1994).
Barenkamp et al., "Identification of a Second Family of High Molecular Weight Adhesion Proteins Expressed by Nontypeable Haemophilus Influenzae (NTHI)," 105th Annual Meeting of the American Pediatric Society and the 64th Annual Meeting of the Society for Pediatric Research, San Diego, California (May 7–11, 1995), *Pediatric Research*, 37(4 part 2):170A (1994).
Fleischmann et al., "Whole–Genome Random Sequencing and Assembly of Haemophilus Influenzae Rd," *Science*, 269(5223):496–498 and 507–512 (1995).

Barenkamp et al., "Identification of a Second Family of High–Molecular–Weight Adhesion Proteins Expressed by Non–Typable Haemophilus Influenzae," *Molecular Microbiology*, 19(6):1215–1223 (1996).
Pechichero et al., "Do Pili Play a Role in Pathogenicity of Haemophilus Influenzae Type B," *The Lancet*, 960–962 (1982).
Bakaletz et al., "Frequency of Fimbriation of Nontypable Haemophilus Influenzae and Its Ability to Adhere to Chinchilla and Human Respiratory Epithelium," *Infection and Immunity*, 56(2):331–335 (1988).
Van Ham et al., "Cloning and Expression in Escherichia coli of Haemophilus Influenzae Fimbrial Genes Establishes Adherence to Oropharyngeal Epithelial Cells," *The EMBO Journal*, 8(11):3535–3540 (1989).
Barenkamp et al., "Cloning, Expression, and DNA Sequence Analysis of Genes Encoding Nontypeable Haemophilus influenzae High–Molecular–Weight Surface–Exposed Proteins Related to Filamentous Hemagglutinin of Bordetella pertussis," *Infection and Immunity*, 60(4):1302–1313 (1992).
St. Geme et al., "Surface Structures and Adherence Properties of Diverse Strains of Haemophilus influenzae Biogroup aegyptius," *Infection and Immunity*, 59(10):3366–3371 (1991).
St. Geme et al., "High–Molecular–Weight Proteins of Nontypable Haemophilus influenzae Mediate Attachment to Human Epithelial Cells," *Proc. Natl. Acad. Sci. USA*, 90:2875–2879 (1993).
St. Geme et al., "Haemophilus influenzae Adheres to and Enters Cultured Human Epithelial Cells," *Infection and Immunity*, 58(12):4036–4044 (1990).
St. Geme et al., "Evidence that Surface Fibrils Expressed by Haemophilus influenzae Type b Promote Attachment to Human Epithelial Cells," *Molecular Microbiology*, 15(1):77–85 (1995).
St. Geme et al., "A Haemophilus influenzae IgA Protease–Like Protein Promotes Intimate Interaction with Human Epithelial Cells," *Molecular Microbiology*, 14(2):217–233 (1994).
Sirakova et al., "Role of Fimbriae Expressed by Nontypeable Haemophilus influenzae in Pathogenesis of and Protection against Otitis Media and Relatedness of the fimbrin Subunit to Outer Membrane Protein A," *Infection and Immunity*, 62(5):2002–2020 (1994).

(List continued on next page.)

Primary Examiner—Patricia A. Duffy
(74) Attorney, Agent, or Firm—Dorsey & Whitney LLP; Richard F. Trecartin; David C. Foster

(57) ABSTRACT

The invention relates to novel Haemophilus adhesion proteins, nucleic acids, and antibodies.

8 Claims, 26 Drawing Sheets

OTHER PUBLICATIONS

Van Ham et al., "The Fimbrial Gene cluster of Haemophilus influenzae type b," *Molecular Microbiology,* 13(4):673–684 (1994).

Van Ham et al., "Contribution of the Major and Minor Subunits to Fimbria–Mediated Adherence of *Haemophilus influenzae* to Human Epithelial Cells and Erythrocytes," *Infection and Immunity,* 63(12):4883–4889 (1995).

Murphy et al., "Somatic antigens of *Haemophilus influenzae* as vaccine components," *Pediatr. Infect. Dis. J.* 8(1):S66–S68 (1989).

Yamanaka et al., "Antibody response to outer membrane protein of nontypeable *Haemophilus influenzae* in otitis–prone children," *J. Pediatr.* 122:212–218 (1993).

* cited by examiner

| | | | | | |
|---|---|---|---|---|---|
| ATGAACAAAA | TTTTTAACGT | TATTTGGAAT | GTTGTGACTC | AAACTTGGGT | TGTCGTATCT | 60 |
| GAACTCACTC | GCACCCACAC | CAAATGCGCC | TCCGCCACCG | TGGCGGTTGC | CGTATTGGCA | 120 |
| ACCCTGTTGT | CCGCAACGGT | TGAGGCGAAC | AACAATACTC | CTGTTACGAA | TAAGTTGAAG | 180 |
| GCTTATGGCG | ATGCGAATTT | TAATTTCACT | AATAATTCGA | TAGCAGATGC | AGAAAAACAA | 240 |
| GTTCAAGAGG | CTTATAAAGG | TTTATTAAAT | CTAAATGAAA | AAAATGCGAG | TGATAAACTG | 300 |
| TTGGTGGAGG | ACAATACTGC | GGCGACCGTA | GGCAATTTGC | GTAAATTGGG | CTGGGTATTG | 360 |
| TCTAGCAAAA | ACGGCACAAG | GAACGAGAAA | AGCCAACAAG | TCAAACATGC | GGATGAAGTG | 420 |
| TTGTTTGAAG | GCAAAGGCGG | TGTGCAGGTT | ACTTCCACCT | CTGAAAACGG | CAAACACACC | 480 |
| ATTACCTTTG | CTTTAGCGAA | AGACCTTGGT | GTGAAAACTG | CGACTGTGAG | TGATACCTTA | 540 |
| ACGATTGGCG | GTGGTGCTGC | TGCAGGTGCT | ACAACAACAC | CGAAAGTGAA | TGTAACTAGT | 600 |
| ACAACTGATG | GCTTGAAGTT | CGCTAAAGAT | GCTGCGGGTG | CTAATGGCGA | TACTACGGTT | 660 |
| CACTTGAATG | GTATTGGTTC | AACCTTGACA | GACACGCTTG | TGGGTTCTCC | TGCTACTCAT | 720 |
| ATTGACGGAG | GAGATCAAAG | TACGCATTAC | ACTCGTGCAG | CAAGTATCAA | GGATGTCTTG | 780 |
| AATGCGGGTT | GGAATATCAA | GGGTGTTAAA | GCTGGCTCAA | CAACTGGTCA | ATCAGAAAAT | 840 |
| GTCGATTTTG | TTCATACTTA | CGATACTGTT | GAGTTCTTGA | GTGCGGATAC | AGAGACCACG | 900 |
| ACTGTTACTG | TAGATAGCAA | AGAAAACGGT | AAGAGAACCG | AAGTTAAAAT | CGGTGCGAAG | 960 |
| ACTTCTGTTA | TCAAAGAAAA | AGACGGTAAG | TTATTTACTG | GAAAAGCTAA | CAAAGAGACA | 1020 |
| AATAAAGTTG | ATGGTGCTAA | CGCGACTGAA | GATGCAGACG | AAGGCAAAGG | CTTAGTGACT | 1080 |
| GCGAAAGATG | TGATTGACGC | AGTGAATAAG | ACTGGTTGGA | GAATTAAAAC | AACCGATGCT | 1140 |
| AATGGTCAAA | ATGGCGACTT | CGCAACTGTT | GCATCAGGCA | CAAATGTAAC | CTTTGCTAGT | 1200 |
| GGTAATGGTA | CAACTGCGAC | TGTAACTAAT | GGCACCGATG | GTATTACCGT | TAAGTATGAT | 1260 |
| GCGAAAGTTG | GCGACGGCTT | AAAACTAGAT | GGCGATAAAA | TCGCTGCAGA | TACGACCGCA | 1320 |

FIG._1A

```
CTTACTGTGA ATGATGGTAA GAACGCTAAT AATCCGAAAG GTAAAGTGGC TGATGTTGCT    1380
TCAACTGACG AGAAGAAATT GGTTACAGCA AAAGGTTTAG TAACAGCCTT AAACAGTCTA    1440
AGCTGGACTA CAACTGCTGC TGAGGCGGAC GGTGGTACGC TTGATGGAAA TGCAAGTGAG    1500
CAAGAAGTTA AAGCGGGCGA TAAAGTAACC TTTAAAGCAG GCAAGAACTT AAAAGTGAAA    1560
CAAGAGGGTG CGAACTTTAC TTATTCACTG CAAGATGCTT TAACAGGCTT AACGAGCATT    1620
ACTTTAGGTA CAGGAAATAA TGGTGCGAAA ACTGAAATCA ACAAAGACGG CTTAACCATC    1680
ACACCAGCAA ATGGTGCGGG TGCAAATAAT GCAAACACCA TCAGCGTAAC CAAAGACGGC    1740
ATTAGTGCGG GCGGTCAGTC GGTTAAAAAC GTTGTGAGCG GACTGAAGAA ATTTGGTGAT    1800
GCGAATTTCG ATCCGCTGAC TAGCTCCGCC GACAACTTAA CGAAACAAAA TGACGATGCC    1860
TATAAAGGCT TGACCAATTT GGATGAAAAA GGTACAGACA AGCAAACTCC AGTTGTTGCC    1920
GACAATACCG CCGCAACCGT GGGCGATTTG CGCGGCTTGG GCTGGGTCAT TTCTGCGGAC    1980
AAAACCACAG GCGGCTCAAC GGAATATCAC GATCAAGTTC GGAATGCGAA CGAAGTGAAA    2040
TTCAAAAGCG GCAACGGTAT CAATGTTTCC GGTAAAACGG TCAACGGTAG GCGTGAAATT    2100
ACTTTTGAAT TGGCTAAAGG TGAAGTGGTT AAATCGAATG AATTTACCGT CAAAGAAACC    2160
AATGGAAAGG AAACGAGCCT GGTTAAAGTT GGCGATAAAT ATTACAGCAA AGAGGATATT    2220
GACTTAACAA CAGGTCAGCC TAAATTAAAA GATGGCAATA CAGTTGCTGC GAAATATCAA    2280
GATAAAGGTG GCAAAGTCGT TTCTGTAACG GATAATACTG AAGCTACCAT AACCAACAAA    2340
GGTTCTGGCT ATGTAACAGG TAACCAAGTG GCAGATGCGA TTGCGAAATC AGGCTTTGAG    2400
CTTGGCTTGG CTGATGAAGC TGATGCGAAA CGGGCGTTTG ATGATAAGAC AAAAGCCTTA    2460
TCTGCTGGTA CAACGGAAAT TGTAAATGCC CACGATAAAG TCCGTTTTGC TAATGGTTTA    2520
AATACCAAAG TGAGCGCGGC AACGGTGGAA AGCACCGATG CAAACGGCGA TAAAGTGACC    2580
ACAACCTTTG TGAAAACCGA TGTGGAATTG CCTTTAACGC AAATCTACAA TACCGATGCA    2640
```

FIG._1B

```
AACGGTAAGA AAATCACTAA AGTTGTCAAA GATGGGCAAA CTAAATGGTA TGAACTGAAT    2700
GCTGACGGTA CGGCTGATAT GACCAAAGAA GTTACCCTCG GTAACGTGGA TTCAGACGGC    2760
AAGAAAGTTG TGAAAGACAA CGATGGCAAG TGGTATCACG CCAAAGCTGA CGGTACTGCG    2820
GATAAAACCA AAGGCGAAGT GAGCAATGAT AAAGTTTCTA CCGATGAAAA ACACGTTGTC    2880
AGCCTTGATC CAAATGATCA ATCAAAAGGT AAAGGTGTCG TGATTGACAA TGTGGCTAAT    2940
GGCGATATTT CTGCCACTTC CACCGATGCG ATTAACGGAA GTCAGTTGTA TGCTGTGGCA    3000
AAAGGGGTAA CAAACCTTGC TGGACAAGTG AATAATCTTG AGGGCAAAGT GAATAAAGTG    3060
GGCAAACGTG CAGATGCAGG TACAGCAAGT GCATTAGCGG CTTCACAGTT ACCACAAGCC    3120
ACTATGCCAG GTAAATCAAT GGTTGCTATT GCGGGAAGTA GTTATCAAGG TCAAAATGGT    3180
TTAGCTATCG GGGTATCAAG AATTTCCGAT AATGGCAAAG TGATTATTCG CTTGTCAGGC    3240
ACAACCAATA GTCAAGGTAA AACAGGCGTT GCAGCAGGTG TTGGTTACCA GTGG          3294
```

FIG._1C

```
Met Asn Lys Ile Phe Asn Val Ile Trp Asn Val Val Thr Gln Thr Trp
1               5               10                  15
Val Val Val Ser Glu Leu Thr Arg Thr His Thr Lys Cys Ala Ser Ala
            20              25                  30
Thr Val Ala Val Ala Val Leu Ala Thr Leu Leu Ser Ala Thr Val Glu
        35              40              45
Ala Asn Asn Asn Thr Pro Val Thr Asn Lys Leu Lys Ala Tyr Gly Asp
    50              55              60
Ala Asn Phe Asn Phe Thr Asn Asn Ser Ile Ala Asp Ala Glu Lys Gln
65              70              75              80
Val Gln Glu Ala Tyr Lys Gly Leu Leu Asn Leu Asn Glu Lys Asn Ala
            85              90              95
Ser Asp Lys Leu Leu Val Glu Asp Asn Thr Ala Ala Thr Val Gly Asn
            100             105             110
Leu Arg Lys Leu Gly Trp Val Leu Ser Ser Lys Asn Gly Thr Arg Asn
            115             120             125
Glu Lys Ser Gln Gln Val Lys His Ala Asp Glu Val Leu Phe Glu Gly
    130             135             140
Lys Gly Gly Val Gln Val Thr Ser Thr Ser Glu Asn Gly Lys His Thr
145             150             155             160
Ile Thr Phe Ala Leu Ala Lys Asp Leu Gly Val Lys Thr Ala Thr Val
                165             170             175
Ser Asp Thr Leu Thr Ile Gly Gly Gly Ala Ala Ala Gly Ala Thr Thr
            180             185             190
Thr Pro Lys Val Asn Val Thr Ser Thr Thr Asp Gly Leu Lys Phe Ala
        195             200             205
Lys Asp Ala Ala Gly Ala Asn Gly Asp Thr Thr Val His Leu Asn Gly
    210             215             220
Ile Gly Ser Thr Leu Thr Asp Thr Leu Val Gly Ser Pro Ala Thr His
225             230             235             240
Ile Asp Gly Gly Asp Gln Ser Thr His Tyr Thr Arg Ala Ala Ser Ile
            245             250             255
Lys Asp Val Leu Asn Ala Gly Trp Asn Ile Lys Gly Val Lys Ala Gly
            260             265             270
Ser Thr Thr Gly Gln Ser Glu Asn Val Asp Phe Val His Thr Tyr Asp
        275             280             285
```

FIG._2A

```
Thr Val Glu Phe Leu Ser Ala Asp Thr Glu Thr Thr Val Thr Val
    290             295             300
Asp Ser Lys Glu Asn Gly Lys Arg Thr Glu Val Lys Ile Gly Ala Lys
305             310             315             320
Thr Ser Val Ile Lys Glu Lys Asp Gly Lys Leu Phe Thr Gly Lys Ala
                325             330             335
Asn Lys Glu Thr Asn Lys Val Asp Gly Ala Asn Ala Thr Glu Asp Ala
            340             345             350
Asp Glu Gly Lys Gly Leu Val Thr Ala Lys Asp Val Ile Asp Ala Val
            355             360             365
Asn Lys Thr Gly Trp Arg Ile Lys Thr Thr Asp Ala Asn Gly Gln Asn
370             375             380
Gly Asp Phe Ala Thr Val Ala Ser Gly Thr Asn Val Thr Phe Ala Ser
385             390             395             400
Gly Asn Gly Thr Thr Ala Thr Val Thr Asn Gly Thr Asp Gly Ile Thr
            405             410             415
Val Lys Tyr Asp Ala Lys Val Gly Asp Gly Leu Lys Leu Asp Gly Asp
            420             425             430
Lys Ile Ala Ala Asp Thr Thr Ala Leu Thr Val Asn Asp Gly Lys Asn
        435             440             445
Ala Asn Asn Pro Lys Gly Lys Val Ala Asp Val Ala Ser Thr Asp Glu
450             455             460
Lys Lys Leu Val Thr Ala Lys Gly Leu Val Thr Ala Leu Asn Ser Leu
465             470             475             480
Ser Trp Thr Thr Thr Ala Ala Glu Ala Asp Gly Gly Thr Leu Asp Gly
            485             490             495
Asn Ala Ser Glu Gln Glu Val Lys Ala Gly Asp Lys Val Thr Phe Lys
            500             505             510
Ala Gly Lys Asn Leu Lys Val Lys Gln Glu Gly Ala Asn Phe Thr Tyr
        515             520             525
Ser Leu Gln Asp Ala Leu Thr Gly Leu Thr Ser Ile Thr Leu Gly Thr
530             535             540
Gly Asn Asn Gly Ala Lys Thr Glu Ile Asn Lys Asp Gly Leu Thr Ile
545             550             555             560
Thr Pro Ala Asn Gly Ala Gly Ala Asn Asn Ala Asn Thr Ile Ser Val
            565             570             575
Thr Lys Asp Gly Ile Ser Ala Gly Gly Gln Ser Val Lys Asn Val Val
            580             585             590
```

FIG. 2B

```
Ser Gly Leu Lys Lys Phe Gly Asp Ala Asn Phe Asp Pro Leu Thr Ser
            595             600             605

Ser Ala Asp Asn Leu Thr Lys Gln Asn Asp Asp Ala Tyr Lys Gly Leu
    610              615             620

Thr Asn Leu Asp Glu Lys Gly Thr Asp Lys Gln Thr Pro Val Val Ala
625              630             635              640

Asp Asn Thr Ala Ala Thr Val Gly Asp Leu Arg Gly Leu Gly Trp Val
            645             650             655

Ile Ser Ala Asp Lys Thr Thr Gly Gly Ser Thr Glu Tyr His Asp Gln
            660             665             670

Val Arg Asn Ala Asn Glu Val Lys Phe Lys Ser Gly Asn Gly Ile Asn
        675             680             685

Val Ser Gly Lys Thr Val Asn Gly Arg Arg Glu Ile Thr Phe Glu Leu
    690             695             700

Ala Lys Gly Glu Val Val Lys Ser Asn Glu Phe Thr Val Lys Glu Thr
705             710             715             720

Asn Gly Lys Glu Thr Ser Leu Val Lys Val Gly Asp Lys Tyr Tyr Ser
                725             730             735

Lys Glu Asp Ile Asp Leu Thr Thr Gly Gln Pro Lys Leu Lys Asp Gly
            740             745             750

Asn Thr Val Ala Ala Lys Tyr Gln Asp Lys Gly Gly Lys Val Val Ser
        755             760             765

Val Thr Asp Asn Thr Glu Ala Thr Ile Thr Asn Lys Gly Ser Gly Tyr
    770             775             780

Val Thr Gly Asn Gln Val Ala Asp Ala Ile Ala Lys Ser Gly Phe Glu
785             790             795             800

Leu Gly Leu Ala Asp Glu Ala Asp Ala Lys Arg Ala Phe Asp Asp Lys
            805             810             815

Thr Lys Ala Leu Ser Ala Gly Thr Thr Glu Ile Val Asn Ala His Asp
            820             825             830

Lys Val Arg Phe Ala Asn Gly Leu Asn Thr Lys Val Ser Ala Ala Thr
        835             840             845

Val Glu Ser Thr Asp Ala Asn Gly Asp Lys Val Thr Thr Phe Val
    850             855             860

Lys Thr Asp Val Glu Leu Pro Leu Thr Gln Ile Tyr Asn Thr Asp Ala
865             870             875             880

Asn Gly Lys Lys Ile Thr Lys Val Val Lys Asp Gly Gln Thr Lys Trp
            885             890             895
```

FIG._2C

Tyr Glu Leu Asn Ala Asp Gly Thr Ala Asp Met Thr Lys Glu Val Thr
                    900                 905                 910

Leu Gly Asn Val Asp Ser Asp Gly Lys Lys Val Val Lys Asp Asn Asp
            915                 920                 925

Gly Lys Trp Tyr His Ala Lys Ala Asp Gly Thr Ala Asp Lys Thr Lys
        930                 935                 940

Gly Glu Val Ser Asn Asp Lys Val Ser Thr Asp Glu Lys His Val Val
945                 950                 955                 960

Ser Leu Asp Pro Asn Asp Gln Ser Lys Gly Lys Gly Val Val Ile Asp
                965                 970                 975

Asn Val Ala Asn Gly Asp Ile Ser Ala Thr Ser Thr Asp Ala Ile Asn
                980                 985                 990

Gly Ser Gln Leu Tyr Ala Val Ala Lys Gly Val Thr Asn Leu Ala Gly
            995                 1000                1005

Gln Val Asn Asn Leu Glu Gly Lys Val Asn Lys Val Gly Lys Arg Ala
    1010                1015                1020

Asp Ala Gly Thr Ala Ser Ala Leu Ala Ala Ser Gln Leu Pro Gln Ala
1025                1030                1035                1040

Thr Met Pro Gly Lys Ser Met Val Ala Ile Ala Gly Ser Ser Tyr Gln
                1045                1050                1055

Gly Gln Asn Gly Leu Ala Ile Gly Val Ser Arg Ile Ser Asp Asn Gly
            1060                1065                1070

Lys Val Ile Ile Arg Leu Ser Gly Thr Thr Asn Ser Gln Gly Lys Thr
        1075                1080                1085

Gly Val Ala Ala Gly Val Gly Tyr Gln Trp
    1090                1095

FIG._2D

```
  1 TTTNTTTTTCTTATTTTTTTTTTTTTTTTTTTTTTTTTTTGAGGCTAAACTTTTNGNA   60

61 AAATATCACTTTTTTATTCTCCAAATATAGAATAGAATACGCACGATTTCACTAAGAAAA 120

121 GTATATTTATCATTAATTTTATTAAATATAAGGTAAATAAAAATGAACAAAATTTTTAAC 180
                                              M  N  K  I  F  N

181 GTTATTTGGAATGTTATGACTCAAACTTGGGTTGTCGTATCTGAACTCACTCGCACCCAC 240
     V  I  W  N  V  M  T  Q  T  W  V  V  V  S  E  L  T  R  T  H

241 ACCAAACGCGCCTCCGCAACCGTGGAGACCGCCGTATTGGCGACACTGTTGTTTGCAACG 300
     T  K  R  A  S  A  T  V  E  T  A  V  L  A  T  L  L  F  A  T

301 GTTCAGGCGAATGCTACCGATGAAGATGAAGAGTTAGACCCCGTAGTACGCACTGCTCCC 360
     V  Q  A  N  A  T  D  E  D  E  E  L  D  P  V  V  R  T  A  P

361 GTGTTGAGCTTCCATTCCGATAAAGAAGGCACGGGAGAAAAAGAAGTTACAGAAAATTCA 420
     V  L  S  F  H  S  D  K  E  G  T  G  E  K  E  V  T  E  N  S

421 AATTGGGGAATATATTTCGACAATAAAGGAGTACTAAAAGCCGGAGCAATCACCCTCAAA 480
     N  W  G  I  Y  F  D  N  K  G  V  L  K  A  G  A  I  T  L  K

481 GCCGGCGACAACCTGAAAATCAAACAAAACACCGATGAAAGCACCAATGCCAGTAGCTTC 540
     A  G  D  N  L  K  I  K  Q  N  T  D  E  S  T  N  A  S  S  F

541 ACCTACTCGCTGAAAAAAGACCTCACAGATCTGACCAGTGTTGCAACTGAAAAATTATCG 600
     T  Y  S  L  K  K  D  L  T  D  L  T  S  V  A  T  E  K  L  S

601 TTTGGCGCAAACGGCGATAAAGTTGATATTACCAGTGATGCAAATGGCTTGAAATTGGCG 660
     F  G  A  N  G  D  K  V  D  I  T  S  D  A  N  G  L  K  L  A

661 AAAACAGGTAACGGAAATGTTCATTTGAATGGTTTGGATTCAACTTTGCCTGATGCGGTA 720
     K  T  G  N  G  N  V  H  L  N  G  L  D  S  T  L  P  D  A  V

721 ACGAATACAGGTGTGTTAAGTTCATCAAGTTTTACACCTAATGATGTTGAAAAAACAAGA 780
     T  N  T  G  V  L  S  S  S  S  F  T  P  N  D  V  E  K  T  R

781 GCTGCAACTGTTAAAGATGTTTTAAATGCAGGTTGGAACATTAAAGGTGCTAAAACTGCT 840
     A  A  T  V  K  D  V  L  N  A  G  W  N  I  K  G  A  K  T  A

841 GGAGGTAATGTTGAGAGTGTTGATTTAGTGTCCGCTTATAATAATGTTGAATTTATTACA 900
     G  G  N  V  E  S  V  D  L  V  S  A  Y  N  N  V  E  F  I  T

901 GGCGATAAAAACACGCTTGATGTTGTATTAACAGCTAAAGAAAACGGTAAAACAACCGAA 960
     G  D  K  N  T  L  D  V  V  L  T  A  K  E  N  G  K  T  T  E

961 GTGAAATTCACACCGAAAACCTCTGTTATCAAAGAAAAGACGGTAAGTTATTTACTGGA 1020
     V  K  F  T  P  K  T  S  V  I  K  E  K  D  G  K  L  F  T  G

1021 AAAGAGAATAACGACACAAATAAAGTTACAAGTAACACGGCGACTGATAATACAGATGAG 1080
      K  E  N  N  D  T  N  K  V  T  S  N  T  A  T  D  N  T  D  E

1081 GGTAATGGCTTAGTCACTGCAAAAGCTGTGATTGATGCTGTGAACAAGGCTGGTTGGAGA 1140
      G  N  G  L  V  T  A  K  A  V  I  D  A  V  N  K  A  G  W  R
```

FIG._3A

```
1141  GTTAAAACAACTACTGCTAATGGTCAAAATGGCGACTTCGCAACTGTTGCGTCAGGCACA  1200
       V  K  T  T  T  A  N  G  Q  N  G  D  F  A  T  V  A  S  G  T

1201  AATGTAACCTTTGAAAGTGGCGATGGTACAACAGCGTCAGTAACTAAAGATACTAACGGC  1260
       N  V  T  F  E  S  G  D  G  T  T  A  S  V  T  K  D  T  N  G

1261  AATGGCATCACTGTTAAGTACGACGCGAAAGTTGGCGACGGCTTGAAATTTGATAGCGAT  1320
       N  G  I  T  V  K  Y  D  A  K  V  G  D  G  L  K  F  D  S  D

1321  AAAAAAATCGTTGCAGATACGACCGCACTTACTGTGACAGGTGGTAAGGTAGCTGAAATT  1380
       K  K  I  V  A  D  T  T  A  L  T  V  T  G  G  K  V  A  E  I

1381  GCTAAAGAAGATGACAAGAAAAAACTTGTTAATGCAGGCGATTTGGTAACAGCTTTAGGT  1440
       A  K  E  D  D  K  K  K  L  V  N  A  G  D  L  V  T  A  L  G

1441  AATCTAAGTTGGAAAGCAAAAGCTGAGGCTGATACTGATGGTGCGCTTGAGGGGATTTCA  1500
       N  L  S  W  K  A  K  A  E  A  D  T  D  G  A  L  E  G  I  S

1501  AAAGACCAAGAAGTCAAAGCAGGCGAAACGGTAACCTTTAAAGCGGGCAAGAACTTAAAA  1560
       K  D  Q  E  V  K  A  G  E  T  V  T  F  K  A  G  K  N  L  K

1561  GTGAAACAGGATGGTGCGAACTTTACTTATTCACTGCAAGATGCTTTAACGGGTTTAACG  1620
       V  K  Q  D  G  A  N  F  T  Y  S  L  Q  D  A  L  T  G  L  T

1621  AGCATTACTTTAGGTGGTACAACTAATGGCGGAAATGATGCGAAAACCGTCATCAACAAA  1680
       S  I  T  L  G  G  T  T  N  G  G  N  D  A  K  T  V  I  N  K

1681  GACGGTTTAACCATCACGCCAGCAGGTAATGGCGGTACGACAGGTACAAACACCATCAGC  1740
       D  G  L  T  I  T  P  A  G  N  G  G  T  T  G  T  N  T  I  S

1741  GTAACCAAAGATGGCATTAAAGCAGGTAATAAAGCTATTACTAATGTTGCGAGTGGTTTA  1800
       V  T  K  D  G  I  K  A  G  N  K  A  I  T  N  V  A  S  G  L

1801  AGAGCTTATGACGATGCGAATTTTGATGTTTTAAATAACTCTGCAACTGATTTAAATAGA  1860
       R  A  Y  D  D  A  N  F  D  V  L  N  N  S  A  T  D  L  N  R

1861  CACGTTGAAGATGCTTATAAAGGTTTATTAAATCTAAATGAAAAAAATGCAAATAAACAA  1920
       H  V  E  D  A  Y  K  G  L  L  N  L  N  E  K  N  A  N  K  Q

1921  CCGTTGGTGACTGACAGCACGGCGGCGACTGTAGGCGATTTACGTAAATTGGGTTGGGTA  1980
       P  L  V  T  D  S  T  A  A  T  V  G  D  L  R  K  L  G  W  V

1981  GTATCAACCAAAAACGGTACGAAAGAAGAAAGCAATCAAGTTAAACAAGCTGATGAAGTC  2040
       V  S  T  K  N  G  T  K  E  E  S  N  Q  V  K  Q  A  D  E  V

2041  CTCTTTACCGGAGCCGGTGCTGCTACGGTTACTTCCAAATCTGAAAACGGTAAACATACG  2100
       L  F  T  G  A  G  A  A  T  V  T  S  K  S  E  N  G  K  H  T

2101  ATTACCGTTAGTGTGGCTGAAACTAAAGCGGATTGCGGTCTTGAAAAAGATGGCGATACT  2160
       I  T  V  S  V  A  E  T  K  A  D  C  G  L  E  K  D  G  D  T

2161  ATTAAGCTCAAAGTGGATAATCAAAACACTGATAATGTTTTAACTGTTGGTAATAATGGT  2220
       I  K  L  K  V  D  N  Q  N  T  D  N  V  L  T  V  G  N  N  G

2221  ACTGCTGTCACTAAAGGTGGCTTTGAAACTGTTAAAACTGGAGCGACTGATGCAGATCGC  2280
       T  A  V  T  K  G  G  F  E  T  V  K  T  G  A  T  D  A  D  R
```

*FIG._3B*

```
2281  GGTAAAGTAACTGTAAAAGATGCTACTGCTAATGACGCTGATAAGAAAGTCGCAACTGTA  2340
      G   K   V   T   V   K   D   A   T   A   N   D   A   D   K   K   V   A   T   V

2341  AAAGATGTTGCAACCGCAATTAATAGTGCGGCGACTTTTGTGAAAACAGAGAATTTAACT  2400
      K   D   V   A   T   A   I   N   S   A   A   T   F   V   K   T   E   N   L   T

2401  ACCTCTATTGATGAAGATAATCCTACAGATAACGGCAAAGATGACGCACTTAAAGCGGGC  2460
      T   S   I   D   E   D   N   P   T   D   N   G   K   D   D   A   L   K   A   G

2461  GATACCTTAACCTTTAAAGCAGGTAAAAACCTGAAAGTTAAACGTGATGGAAAAAATATT  2520
      D   T   L   T   F   K   A   G   K   N   L   K   V   K   R   D   G   K   N   I

2521  ACTTTTGACTTGGCGAAAAACCTTGAGGTGAAAACTGCGAAAGTGAGTGATACTTTAACG  2580
      T   F   D   L   A   K   N   L   E   V   K   T   A   K   V   S   D   T   L   T

2581  ATTGGCGGGAATACACCTACAGGTGGCACTACTGCGACGCCAAAAGTGAATATTACTAGC  2640
      I   G   G   N   T   P   T   G   G   T   T   A   T   P   K   V   N   I   T   S

2641  ACGGCTGATGGTTTGAATTTTGCAAAAGAAACAGCCGATGCCTCGGGTTCTAAGAATGTT  2700
      T   A   D   G   L   N   F   A   K   E   T   A   D   A   S   G   S   K   N   V

2701  TATTTGAAAGGTATTGCGACAACTTTAACTGAGCCAAGCGCGGGAGCGAAGTCTTCACAC  2760
      Y   L   K   G   I   A   T   T   L   T   E   P   S   A   G   A   K   S   S   H

2761  GTTGATTTAAATGTGGATGCGACGAAAAAATCCAATGCAGCAAGTATTGAAGATGTATTG  2820
      V   D   L   N   V   D   A   T   K   K   S   N   A   A   S   I   E   D   V   L

2821  CGCGCAGGTTGGAATATTCAAGGTAATGGTAATAATGTTGATTATGTAGCGACGTATGAC  2880
      R   A   G   W   N   I   Q   G   N   G   N   N   V   D   Y   V   A   T   Y   D

2881  ACAGTAAACTTTACCGATGACAGCACAGGTACAACAACGGTAACCGTAACCCAAAAAGCA  2940
      T   V   N   F   T   D   D   S   T   G   T   T   T   V   T   V   T   Q   K   A

2941  GATGGCAAAGGTGCTGACGTTAAAATCGGTGCGAAAACTTCTGTTATCAAAGACCACAAC  3000
      D   G   K   G   A   D   V   K   I   G   A   K   T   S   V   I   K   D   H   N

3001  GGCAAACTGTTTACAGGCAAAGACCTGAAAGATGCGAATAATGGTGCAACCGTTAGTGAA  3060
      G   K   L   F   T   G   K   D   L   K   D   A   N   N   G   A   T   V   S   E

3061  GATGATGGCAAAGACACCGGCACAGGCTTAGTTACTGCAAAAACTGTGATTGATGCAGTA  3120
      D   D   G   K   D   T   G   T   G   L   V   T   A   K   T   V   I   D   A   V

3121  AATAAAAGCGGTTGGAGGGTAACCGGTGAGGGCGCGACTGCCGAAACCGGTGCAACCGCC  3180
      N   K   S   G   W   R   V   T   G   E   G   A   T   A   E   T   G   A   T   A

3181  GTGAATGCGGGTAACGCTGAAACCGTTACATCAGGCACGAGCGTGAACTTCAAAAACGGC  3240
      V   N   A   G   N   A   E   T   V   T   S   G   T   S   V   N   F   K   N   G

3241  AATGCGACCACAGCGACCGTAAGCAAAGATAATGGCAACATCAATGTCAAATACGATGTA  3300
      N   A   T   T   A   T   V   S   K   D   N   G   N   I   N   V   K   Y   D   V

3301  AATGTTGGTGACGGCTTGAAGATTGGCGATGACAAAAAAATCGTTGCAGACACGACCACA  3360
      N   V   G   D   G   L   K   I   G   D   D   K   K   I   V   A   D   T   T   T

3361  CTTACTGTAACAGGTGGTAAGGTGTCTGTTCCTGCTGGTGCTAATAGTGTTAATAACAAT  3420
      L   T   V   T   G   G   K   V   S   V   P   A   G   A   N   S   V   N   N   N
```

FIG._3C

```
3421 AAGAAACTTGTTAATGCAGAGGGTTTAGCGACTGCTTTAAACAACCTAAGCTGGACGGCA 3480
      K  K  L  V  N  A  E  G  L  A  T  A  L  N  N  L  S  W  T  A

3481 AAAGCCGATAAATATGCAGATGGCGAGTCAGAGGGCGAAACCGACCAAGAAGTCAAAGCA 3540
      K  A  D  K  Y  A  D  G  E  S  E  G  E  T  D  Q  E  V  K  A

3541 GGCGACAAAGTAACCTTTAAAGCAGGCAAGAACTTAAAAGTGAAACAGTCTGAAAAAGAC 3600
      G  D  K  V  T  F  K  A  G  K  N  L  K  V  K  Q  S  E  K  D

3601 TTTACTTATTCACTGCAAGACACTTTAACAGGCTTAACGAGCATTACTTTAGGTGGTACA 3660
      F  T  Y  S  L  Q  D  T  L  T  G  L  T  S  I  T  L  G  G  T

3661 GCTAATGGCAGAAATGATACGGGAACCGTCATCAACAAAGACGGCTTAACCATCACGCTG 3720
      A  N  G  R  N  D  T  G  T  V  I  N  K  D  G  L  T  I  T  L

3721 GCAAATGGTGCTGCGGCAGGCACAGATGCGTCTAACGGAAACACCATCAGTGTAACCAAA 3780
      A  N  G  A  A  A  G  T  D  A  S  N  G  N  T  I  S  V  T  K

3781 GACGGCATTAGTGCGGGTAATAAAGAAATTACCAATGTTAAGAGTGCTTTAAAAACCTAT 3840
      D  G  I  S  A  G  N  K  E  I  T  N  V  K  S  A  L  K  T  Y

3841 AAAGATACTCAAAACACTGCAGATGAAACACAAGATAAAGAGTTCCACGCCGCCGTTAAA 3900
      K  D  T  Q  N  T  A  D  E  T  Q  D  K  E  F  H  A  A  V  K

3901 AACGCAAATGAAGTTGAGTTCGTGGGTAAAAACGGTGCAACCGTGTCTGCAAAAACTGAT 3960
      N  A  N  E  V  E  F  V  G  K  N  G  A  T  V  S  A  K  T  D

3961 AACAACGGAAAACATACTGTAACGATTGATGTTGCAGAAGCCAAAGTTGGTGATGGTCTT 4020
      N  N  G  K  H  T  V  T  I  D  V  A  E  A  K  V  G  D  G  L

4021 GAAAAAGATACTGACGGCAAGATTAAACTCAAAGTAGATAATACAGATGGGAATAATCTA 4080
      E  K  D  T  D  G  K  I  K  L  K  V  D  N  T  D  G  N  N  L

4081 TTAACCGTTGATGCAACAAAAGGTGCATCCGTTGCCAAGGGCGAGTTTAATGCCGTAACA 4140
      L  T  V  D  A  T  K  G  A  S  V  A  K  G  E  F  N  A  V  T

4141 ACAGATGCAACTACAGCCCAAGGCACAAATGCCAATGAGCGCGGTAAAGTGGTTGTCAAG 4200
      T  D  A  T  T  A  Q  G  T  N  A  N  E  R  G  K  V  V  V  K

4201 GGTTCAAATGGTGCAACTGCTACCGAAACTGACAAGAAAAAAGTGGCAACTGTTGGCGAC 4260
      G  S  N  G  A  T  A  T  E  T  D  K  K  K  V  A  T  V  G  D

4261 GTTGCTAAAGCGATTAACGACGCAGCAACTTTCGTGAAAGTGGAAAATGACGACAGTGCT 4320
      V  A  K  A  I  N  D  A  A  T  F  V  K  V  E  N  D  D  S  A

4321 ACGATTGATGATAGCCCAACAGATGATGGCGCAAATGATGCTCTCAAAGCAGGCGACACC 4380
      T  I  D  D  S  P  T  D  D  G  A  N  D  A  L  K  A  G  D  T

4381 TTGACCTTAAAAGCGGGTAAAAACTTAAAAGTTAAACGTGATGGTAAAAATATTACTTTT 4440
      L  T  L  K  A  G  K  N  L  K  V  K  R  D  G  K  N  I  T  F

4441 GCCCTTGCGAACGACCTTAGTGTAAAAAGCGCAACCGTTAGCGATAAATTATCGCTTGGT 4500
      A  L  A  N  D  L  S  V  K  S  A  T  V  S  D  K  L  S  L  G

4501 ACAAACGGCAATAAAGTCAATATCACAAGCGACACCAAAGGCTTGAACTTCGCTAAAGAT 4560
      T  N  G  N  K  V  N  I  T  S  D  T  K  G  L  N  F  A  K  D
```

FIG._3D

```
4561  AGTAAGACAGGCGATGATGCTAATATTCACTTAAATGGCATTGCTTCAACTTTAACTGAT  4620
       S  K  T  G  D  D  A  N  I  H  L  N  G  I  A  S  T  L  T  D

4621  ACATTGTTAAATAGTGGTGCGACAACCAATTTAGGTGGTAATGGTATTACTGATAACGAG  4680
       T  L  L  N  S  G  A  T  T  N  L  G  G  N  G  I  T  D  N  E

4681  AAAAAACGCGCGGCGAGCGTTAAAGATGTCTTGAATGCGGGTTGGAATGTTCGTGGTGTT  4740
       K  K  R  A  A  S  V  K  D  V  L  N  A  G  W  N  V  R  G  V

4741  AAACCGGCATCTGCAAATAATCAAGTGGAGAATATCGACTTTGTAGCAACCTACGACACA  4800
       K  P  A  S  A  N  N  Q  V  E  N  I  D  F  V  A  T  Y  D  T

4801  GTGGACTTTGTTAGTGGAGATAAAGACACCACGAGTGTAACTGTTGAAAGTAAAGATAAT  4860
       V  D  F  V  S  G  D  K  D  T  T  S  V  T  V  E  S  K  D  N

4861  GGCAAGAGAACCGAAGTTAAAATCGGTGCGAAGACTTCTGTTATCAAAGACCACAACGGC  4920
       G  K  R  T  E  V  K  I  G  A  K  T  S  V  I  K  D  H  N  G

4921  AAACTGTTTACAGGCAAAGAGCTGAAGGATGCTAACAATAATGGCGTAACTGTTACCGAA  4980
       K  L  F  T  G  K  E  L  K  D  A  N  N  N  G  V  T  V  T  E

4981  ACCGACGGCAAAGACGAGGGTAATGGTTTAGTGACTGCAAAAGCTGTGATTGATGCCGTG  5040
       T  D  G  K  D  E  G  N  G  L  V  T  A  K  A  V  I  D  A  V

5041  AATAAGGCTGGTTGGAGAGTTAAAACAACAGGTGCTAATGGTCAGAATGATGACTTCGCA  5100
       N  K  A  G  W  R  V  K  T  T  G  A  N  G  Q  N  D  D  F  A

5101  ACTGTTGCGTCAGGCACAAATGTAACCTTTGCTGATGGTAATGGCACAACTGCCGAAGTA  5160
       T  V  A  S  G  T  N  V  T  F  A  D  G  N  G  T  T  A  E  V

5161  ACTAAAGCAAACGACGGTAGTATTACTGTTAAATACAATGTTAAAGTGGCTGATGGCTTA  5220
       T  K  A  N  D  G  S  I  T  V  K  Y  N  V  K  V  A  D  G  L

5221  AAACTAGACGGCGATAAAATCGTTGCAGACACGACCGTACTTACTGTGGCAGATGGTAAA  5280
       K  L  D  G  D  K  I  V  A  D  T  T  V  L  T  V  A  D  G  K

5281  GTTACAGCTCCGAATAATGGCGATGGTAAGAAATTTGTTGATGCAAGTGGTTTAGCGGAT  5340
       V  T  A  P  N  N  G  D  G  K  K  F  V  D  A  S  G  L  A  D

5341  GCGTTAAATAAATTAAGCTGGACGGCAACTGCTGGTAAAGAAGGCACTGGTGAAGTTGAT  5400
       A  L  N  K  L  S  W  T  A  T  A  G  K  E  G  T  G  E  V  D

5401  CCTGCAAATTCAGCAGGGCAAGAAGTCAAAGCGGGCGACAAAGTAACCTTTAAAGCCGGC  5460
       P  A  N  S  A  G  Q  E  V  K  A  G  D  K  V  T  F  K  A  G

5461  GACAACCTGAAAATCAAACAAAGCGGCAAAGACTTTACCTACTCGCTGAAAAAAGAGCTG  5520
       D  N  L  K  I  K  Q  S  G  K  D  F  T  Y  S  L  K  K  E  L

5521  AAAGACCTGACCAGCGTAGAGTTCAAAGACGCAAACGGCGGTACAGGCAGTGAAAGCACC  5580
       K  D  L  T  S  V  E  F  K  D  A  N  G  G  T  G  S  E  S  T

5581  AAGATTACCAAAGACGGCTTGACCATTACGCCGGCAAACGGTGCGGGTGCGGCAGGTGCA  5640
       K  I  T  K  D  G  L  T  I  T  P  A  N  G  A  G  A  A  G  A

5641  AACACTGCAAACACCATTAGCGTAACCAAAGATGGCATTAGCGCGGGTAATAAAGCAGTT  5700
       N  T  A  N  T  I  S  V  T  K  D  G  I  S  A  G  N  K  A  V
```

FIG._3E

```
5701  ACAAACGTTGTGAGCGGACTGAAGAAATTTGGTGATGGTCATACGTTGGCAAATGGCACT  5760
       T  N  V  V  S  G  L  K  K  F  G  D  G  H  T  L  A  N  G  T

5761  GTTGCTGATTTTGAAAAGCATTATGACAATGCCTATAAAGACTTGACCAATTTGGATGAA  5820
       V  A  D  F  E  K  H  Y  D  N  A  Y  K  D  L  T  N  L  D  E

5821  AAAGGCGCGGATAATAATCCGACTGTTGCCGACAATACCGCTGCAACCGTGGGCGATTTG  5880
       K  G  A  D  N  N  P  T  V  A  D  N  T  A  A  T  V  G  D  L

5881  CGCGGCTTGGGCTGGGTCATTTCTGCGGACAAAACCACAGGCGAACCCAATCAGGAATAC  5940
       R  G  L  G  W  V  I  S  A  D  K  T  T  G  E  P  N  Q  E  Y

5941  AACGCGCAAGTGCGTAACGCCAATGAAGTGAAATTCAAGAGCGGCAACGGTATCAATGTT  6000
       N  A  Q  V  R  N  A  N  E  V  K  F  K  S  G  N  G  I  N  V

6001  TCCGGTAAAACATTGAACGGTACGCGCGTGATTACCTTTGAATTGGCTAAAGGCGAAGTG  6060
       S  G  K  T  L  N  G  T  R  V  I  T  F  E  L  A  K  G  E  V

6061  GTTAAATCGAATGAATTTACCGTTAAGAATGCCGATGGTTCGGAAACGAACTTGGTTAAA  6120
       V  K  S  N  E  F  T  V  K  N  A  D  G  S  E  T  N  L  V  K

6121  GTTGGCGATATGTATTACAGCAAAGAGGATATTGACCCGGCAACCAGTAAACCGATGACA  6180
       V  G  D  M  Y  Y  S  K  E  D  I  D  P  A  T  S  K  P  M  T

6181  GGTAAAACTGAAAAATATAAGGTTGAAAACGGCAAAGTCGTTTCTGCTAACGGCAGCAAG  6240
       G  K  T  E  K  Y  K  V  E  N  G  K  V  V  S  A  N  G  S  K

6241  ACCGAAGTTACCCTAACCAACAAAGGTTCCGGCTATGTAACAGGTAACCAAGTGGCTGAT  6300
       T  E  V  T  L  T  N  K  G  S  G  Y  V  T  G  N  Q  V  A  D

6301  GCGATTGCGAAATCAGGCTTTGAGCTTGGTTTGGCTGATGCGGCAGAAGCTGAAAAAGCC  6360
       A  I  A  K  S  G  F  E  L  G  L  A  D  A  A  E  A  E  K  A

6361  TTTGCAGAAAGCGCAAAAGACAAGCAATTGTCTAAAGATAAAGCGGAAACTGTAAATGCC  6420
       F  A  E  S  A  K  D  K  Q  L  S  K  D  K  A  E  T  V  N  A

6421  CACGATAAAGTCCGTTTTGCTAATGGTTTAAATACCAAAGTGAGCGCGGCAACGGTGGAA  6480
       H  D  K  V  R  F  A  N  G  L  N  T  K  V  S  A  A  T  V  E

6481  AGCACTGATGCAAACGGCGATAAAGTGACCACAACCTTTGTGAAAACCGATGTGGAATTG  6540
       S  T  D  A  N  G  D  K  V  T  T  T  F  V  K  T  D  V  E  L

6541  CCTTTAACGCAAATCTACAATACCGATGCAAACGGTAATAAGATCGTTAAAAAAGCTGAC  6600
       P  L  T  Q  I  Y  N  T  D  A  N  G  N  K  I  V  K  K  A  D

6601  GGAAAATGGTATGAACTGAATGCTGATGGTACGGCGAGTAACAAAGAAGTGACACTTGGT  6660
       G  K  W  Y  E  L  N  A  D  G  T  A  S  N  K  E  V  T  L  G

6661  AACGTGGATGCAAACGGTAAGAAAGTTGTGAAAGTAACCGAAAATGGTGCGGATAAGTGG  6720
       N  V  D  A  N  G  K  K  V  V  K  V  T  E  N  G  A  D  K  W

6721  TATTACACCAATGCTGACGGTGCTGCGGATAAAACCAAAGGCGAAGTGAGCAATGATAAA  6780
       Y  Y  T  N  A  D  G  A  A  D  K  T  K  G  E  V  S  N  D  K

6781  GTTTCTACCGATGAAAAACACGTTGTCCGCCTTGATCCGAACAATCAATCGAACGGCAAA  6840
       V  S  T  D  E  K  H  V  V  R  L  D  P  N  N  Q  S  N  G  K
```

FIG._3F

```
6841  GGCGTGGTCATTGACAATGTGGCTAATGGCGAAATTTCTGCCACTTCCACCGATGCGATT  6900
       G  V  V  I  D  N  V  A  N  G  E  I  S  A  T  S  T  D  A  I

6901  AACGGAAGTCAGTTGTATGCCGTGGCAAAAGGGGTAACAAACCTTGCTGGACAAGTGAAT  6960
       N  G  S  Q  L  Y  A  V  A  K  G  V  T  N  L  A  G  Q  V  N

6961  AATCTTGAGGGCAAAGTGAATAAAGTGGGCAAACGTGCAGATGCAGGTACAGCAAGTGCA  7020
       N  L  E  G  K  V  N  K  V  G  K  R  A  D  A  G  T  A  S  A

7021  TTAGCGGCTTCACAGTTACCACAAGCCACTATGCCAGGTAAATCAATGGTTGCTATTGCG  7080
       L  A  A  S  Q  L  P  Q  A  T  M  P  G  K  S  M  V  A  I  A

7081  GGAAGTAGTTATCAAGGTCAAAATGGTTTAGCTATCGGGGTATCAAGAATTTCCGATAAT  7140
       G  S  S  Y  Q  G  Q  N  G  L  A  I  G  V  S  R  I  S  D  N

7141  GGCAAAGTGATTATTCGCTTGTCAGGCACAACCAATAGTCAAGGTAAAACAGGCGTTGCA  7200
       G  K  V  I  I  R  L  S  G  T  T  N  S  Q  G  K  T  G  V  A

7201  GCAGGTGTTGGTTACCAGTGGTAAAGTTTGGATTATCTCTCTTAAAAAGCGGCATTTGCC  7260
       A  G  V  G  Y  Q  W

7261  GCTTTTTTTATGGGTGGCTATTATGTATCGT  7291
```

FIG._3G

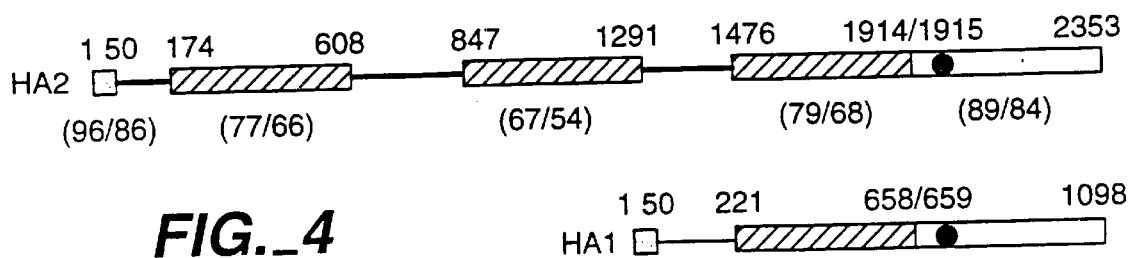
FIG._4

```
HA2    1 MNKIFNVIWNVMTQTWVVVSELTRTHTKRLRNR.GDPVLATLLFATVQA.  48
         ||||||||||:||||||||||||||||||   .. : :|||||| |||:|
HA1    1 MNKIFNVIWNVVTQTWVVVSELTRTHTKCASATVAVAVLATLLSATVEAN  50

49 NATDEDEELDPVVRTAPVLSFHSDKEGTGEKEVTENSNWGIYFDNKG...  95
         |.|. ..:.|.:    ...: :.| .:.  :.:|||:| |. .  : :::|.
      51 NNTPVTNKLKAY..GDANFNFTNNSIADAEKQVQEAYKGLLNLNEKNASD  98

96 ...VLKAGAITL.....................KAGDNLKXKQXTD    117
         ...| ...| |:                      .|:: |  . .
      99 KLLVEDNTAATVGNLRKLGWVLSSKNGTRNEKSQQVKHADEVLFEGKGGV 148

118 EXTNAS.....SFTYSLKKDLTDLTSVATEKLSFGANGD.......KVDI 155
         : |..|    .:|:.| |||. |.....|.:|:..:.        ||::
     149 QVTSTSENGKHTITFALAKDLGVKTATVSDTLTIGGGAAAGATTTPKVNV 198

156 TSDANGLKLAK.....TGNGNVHLNGLDSTLPDAVTNTGVLSSSSFTPND 200
         ||..:|||:||      .|:..||||||::|||.|.:....   ..: ....
     199 TSTTDGLKFAKDAAGANGDTTVHLNGIGSTLTDTLVGSPATHIDG.GDQS 247

201 VEKTRAATVKDVLNAGWNIKGAKTAG..GNVESVDLVSAYNNVEFITGDK 248
         .. ||||.:|||||||||||||.|.:: |. |.||:| .|:.|||:.:|.
     248 THYTRAASIKDVLNAGWNIKGVKAGSTTGQSENVDFVHTYDTVEFLSADT 297

249 NTLDVVLTAKENXKTTEVKFTPKTSVIKEKDGKLFTGKENNDTNKVTSNT 298
         :| .|.:..||| | ||||:.:||||||||||||||||.|.:||||.:..
     298 ETTTVTVDSKENGKRTEVKIGAKTSVIKEKDGKLFTGKANKETNKVDGAN 347

299 ATDNTDEGNGLVTAKAVIDAVNKAGWRVKTTTANGQNGDFATVASGTNVT 348
         ||::.|||.||||||.|||||||.|||:|||.||||||||||||||||||
     348 ATEDADEGKGLVTAKDVIDAVNKTGWRIKTTDANGQNGDFATVASGTNVT 397

349 FESGDGTTASVTKDTNGNGITVKYDAKVGDGLKFDSDKKIVADTTALTVT 398
         |.||:||||.||.:|  :||||||||||||||||:|:| ||.||||||||.
     398 FASGNGTTATVTNGT..DGITVKYDAKVGDGLKLDGD.KIAADTTALTVN 444

399 G........GKVAEIAKEDDKKKLVNAGDLVTALGNLSWKAKAEADTDGA 440
         :        ||||::|..|: ||||.| :||||..|||...|....:|.
     445 DGKNANNPKGKVADVASTDE.KKLVTAKGLVTALNSLSWTTTAAEADGGT 493

441 LEGISKDQEVKAGETVTFKAGKNLKVKQDGANFTYSLQDALTGLTSITLG 490
         |:|  ..:|||||||:.||||||||||||||:||||||||||||||||||
     494 LDGNASEQEVKAGDKVTFKAGKNLKVKQEGANFTYSLQDALTGLTSITLG 543

491 GTTNGGNDAKTVINKDGLTITPAGNGGTTGTNTISVTKDGIKAGNKAITN 540
         .  |.|:|||  ||||||||||||..:|....||||||||||.||...:..|
```

FIG._5A

```
544 T...GNNGAKTEINKDGLTITPANGAGANNANTISVTKDGISAGGQSVKN 590

541 VASGLRAYDDANFDVLNNSATDLNRHVEDAYKGLLNLNEKNANKQ.PLVT 589
    |.|||: ::|||||.|..||.:|.:: :||||||  ||:||..:|| |:|.
591 VVSGLKKFGDANFDPLTSSADNLTKQNDDAYKGLTNLDEKGTDKQTPVVA 640

590 DSTAATVGDLRKLGWVVS 607
    |.||||||||| ||||:|
641 DNTAATVGDLRGLGWVIS 658
```

FIG._5B

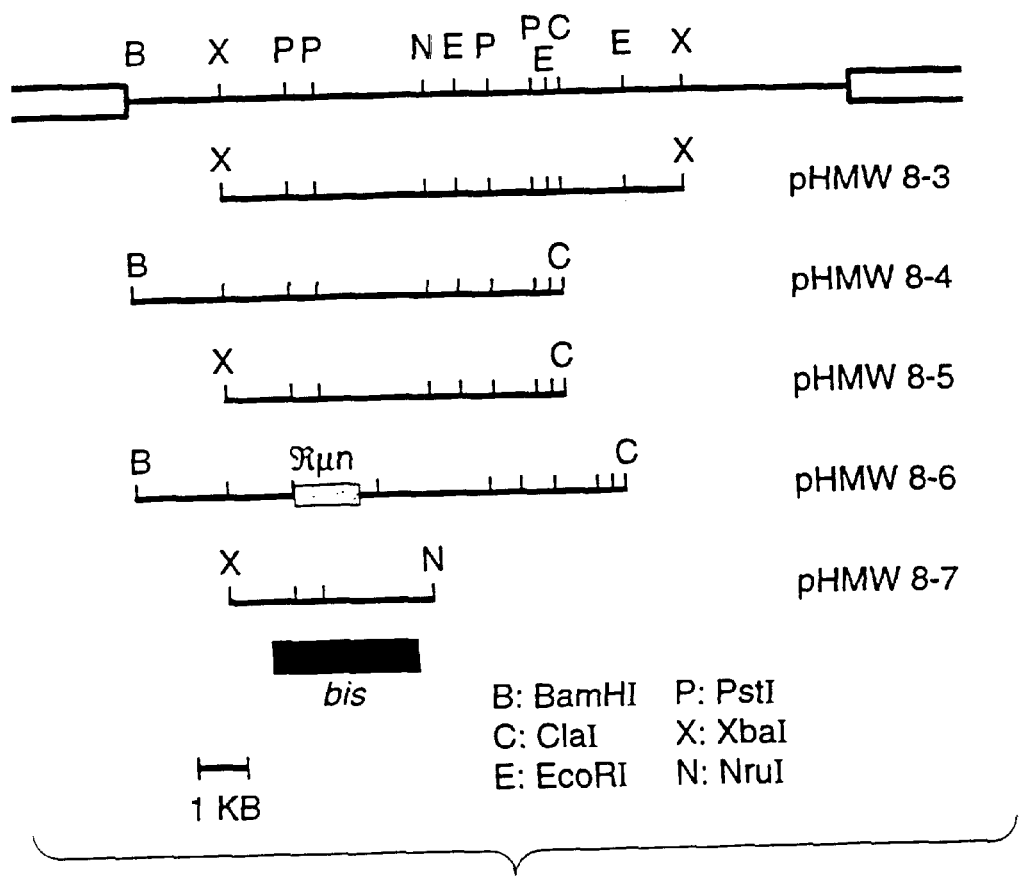
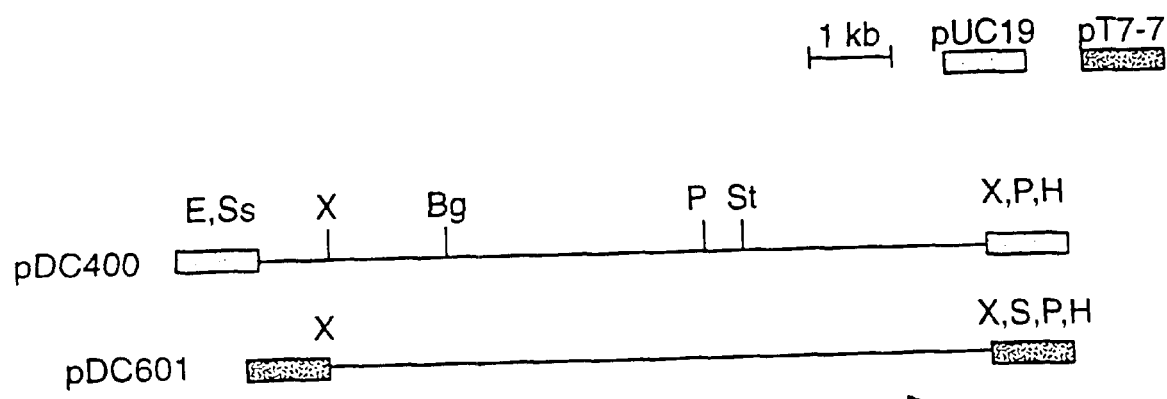

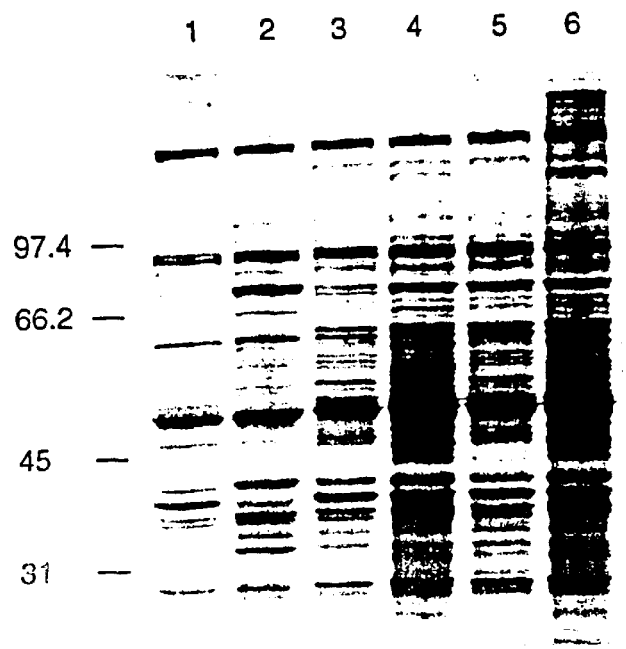
FIG._8
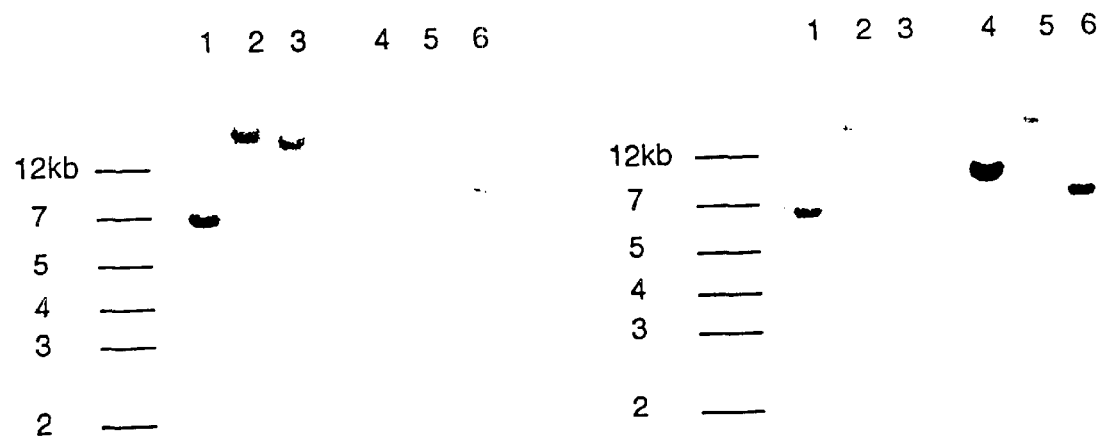
FIG._9A    FIG._9B

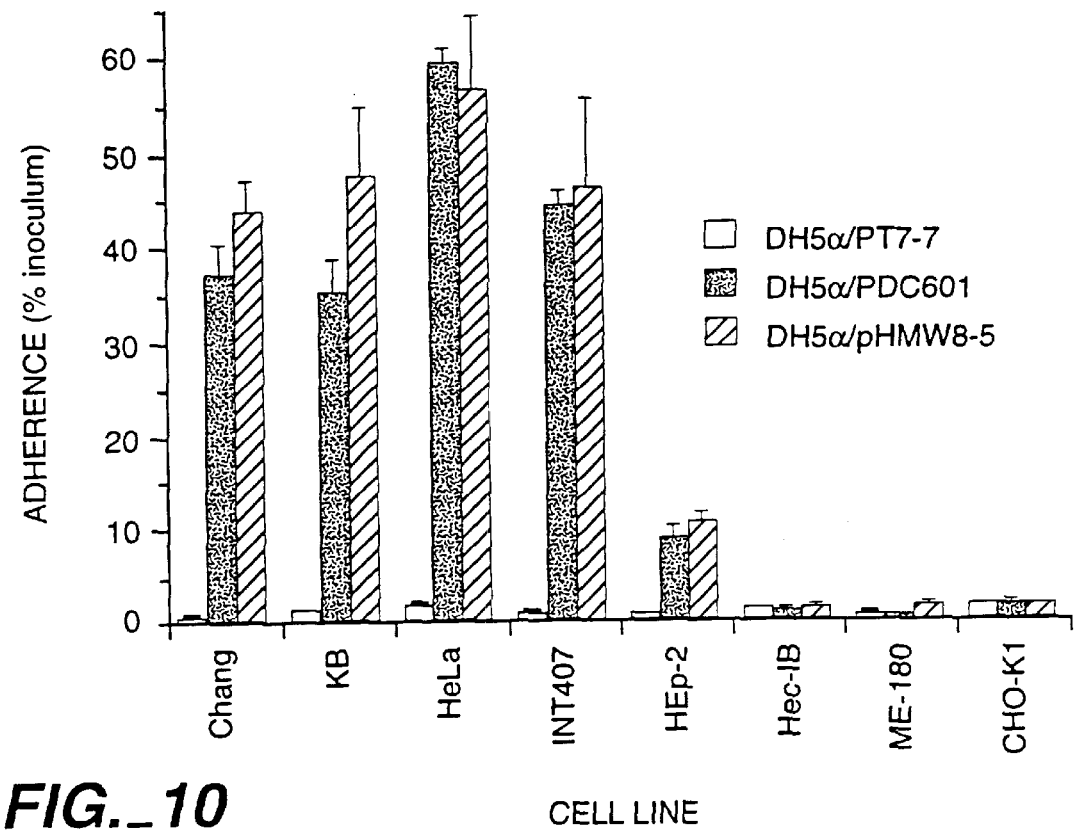
FIG._10
| | 1 | | |
|---|---|---|---|
| HA2 | MNKIFNVIWN | VMTQTWVVS | ELTR |
| HA1 | MNKIFNVIWN | VVTQTWVVS | ELTR |
| HMW1 | MNKIYRLKFS | KRLNALVAVS | ELAR |
| HMW2 | MNKIYRLKFS | KRLNALVAVS | ELAR |
| AIDA-1 | MNKAYSIIWS | HSRQAWIVAS | ELAR |
| Tsh | MNRIYSLRYS | AVARGFIAVS | EFAR |
| SepA | MNKIYYLKYC | HITKSLIAVS | ELAR |
| Consensus | MNKIY--IWS | -VTQ-W--VS | ELAR |
FIG._11

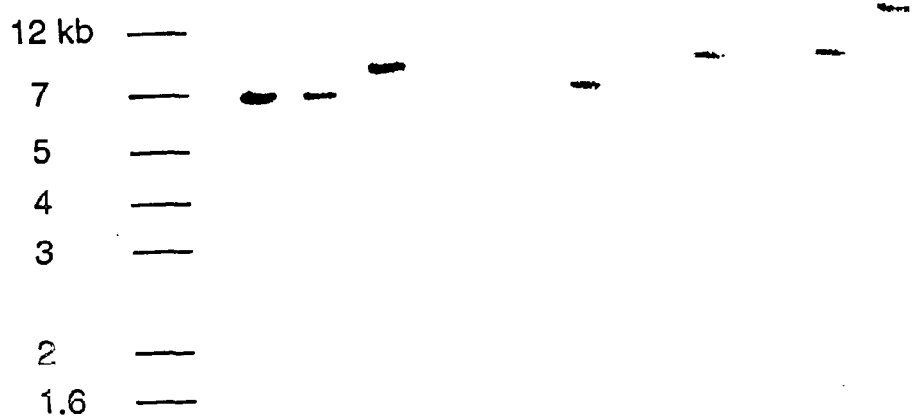
FIG._12
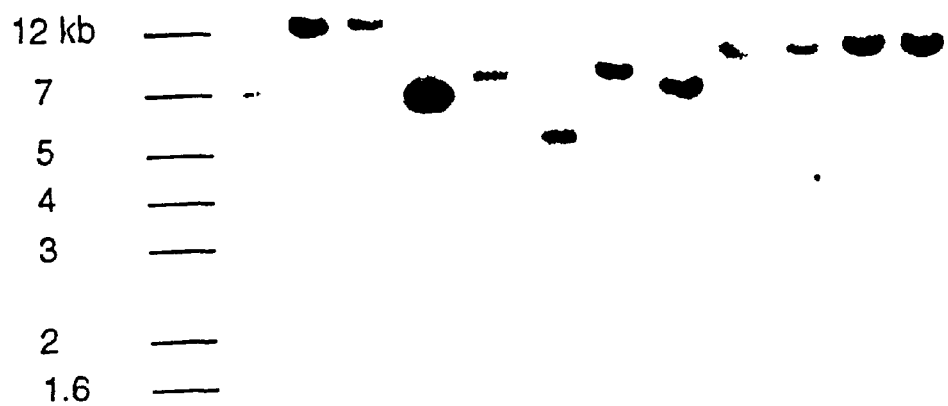
FIG._13

```
  1  ATGAACAAAA TTTTTAACGT TATTTGGAAT GTTGTGACTC AAACTTGGGT
 51  TGTCGTATCT GAACTCACTC GCACCCACAC CAAATGCGCC TCCGCCACCG
101  TGGCAGTTGC CGTATTGGCA ACCCTGTTGT CCGCAACGGT TCAGGCGAAT
151  GCTACCGATG AAAACGAAGA TGATGAAGAA GAGTTAGAAC CCGTACAACG
201  CTCTGTTTTA AGGTGGAGCT TCAAATCCGC TAAGGAAGGC ACTGGAGAAC
251  AAGAGGGAAC AACAGAGGTA ATAAATTTGA ACACAGATTC ATCAGGAAAT
301  GCAGTAGGAA GCAGCACAAT CACCTTCAAA GCCGGCGACA ACCTGAAAAT
351  CAAACAAAGC GGCAATGACT TCACCTACTC GCTGAAAAAA GAGCTGAAAA
401  ACCTGACCAG TGTTGAAACT GAAAATTAT CGTTTGGCGC AAACGGCAAT
451  AAAGTTGATA TTACCAGTGA TGCAAATGGC TTGAAATTGG CGAAAACAGG
501  TAACGGAAAT GGTCAAAACA GTAATGTTCA CTTAAACGGT ATTGCTTCGA
551  CTTTGACCGA TACGCTTGCC GGTGGCACAA CAGGACACGT TGACACCAAC
601  ATTGATGCGG TTAATTATCA TCGCGCTGCA AGCGTACAAG ATGTGTTAAA
651  CAGCGGTTGG AATATCCAAG GCAATGGAAA CAATGTCGAT TTTGTCCGTA
701  CTTACGACAC CGTGGACTTT GTCAATGGCG CGAATGCCAA TGTGAGCGTT
751  ACGGCTGATA CGGCTCACAA AAAGACAACT GTCCGTGTGG ATGTAACAGG
801  CTTGCCGGTT CAATATGTTA CGGAAGACGG CAAAACCGTT GTGAAAGTGG
851  GCAATGAGTA TTACAAAGCC AAAGATGACG GTTCGGCGGA TATGAATCAA
901  AAAGTCGAAA ACGGCGAGCT GGCGAAAACC AAAGTGAAAT TGGTATCGGC
951  AAGCGGTACA AATCCGGTGA AAATTAGCAA TGTTGCAGAC GGCACGGAAG
```

FIG._14A

```
1001  ACACCGATGC GGTCAGCTTT AAGCAATTAA AAGCCTTGCA AGACAAACAG
1051  GTTACGTTGA GCACGAGCAA TGCTTATGCC AATGGCGGTA CAGATAACGA
1101  CGGCGGCAAG GCAACTCAAA CTTTAAGCAA TGGTTTGAAT TTTAAATTTA
1151  AATCTAGCGA TGGCGAGTTG TTGAAAATTA GCGCGACCGG CGATACGGTT
1201  ACTTTTACGC CGAAAAAAGG TTCGGTACAG GTTGGCGATG ATGGCAAGGC
1251  TTCAATTTCA AAAGGTGCAA ATACAACTGA AGGTTTGGTT GAGGCTTCTG
1301  AATTGGTTGA AAGCCTGAAC AAACTGGGTT GGAAAGTAGG GGTTGAGAAA
1351  GTCGGCAGCG GCGAGCTTGA TGGTACATCC AAGGAAACTT TAGTGAAGTC
1401  GGGCGATAAA GTAACTTTGA AAGCCGGCGA CAATCTGAAG GTCAAACAAG
1451  AGGGCACAAA CTTCACTTAC GCGCTCAAAG ATGAATTGAC GGGCGTGAAG
1501  AGCGTGGAGT TTAAAGACAC GGCGAATGGT GCAAACGGTG CAAGCACGAA
1551  GATTACCAAA GACGGCTTGA CCATTACGCT GGCAAACGGT GCGAATGGTG
1601  CGACGGTGAC TGATGCCGAC AAGATTAAAG TTGCTTCGGA CGGCATTAGC
1651  GCGGGTAATA AAGCAGTTAA AAACGTCGCG GCAGGCGAAA TTTCTGCCAC
1701  TTCCACCGAT GCGATTAACG GAAGCCAGTT GTATGCCGTG GCAAAAGGGG
1751  TAACAAACCT TGCTGGACAA GTGAATAATC TTGAGGGCAA AGTGAATAAA
1801  GTGGGCAAAC GTGCAGATGC AGGTACTGCA AGTGCATTAG CGGCTTCACA
1851  GTTACCACAA GCCACTATGC CAGGTAAATC AATGGTTTCT ATTGCGGGAA
1901  GTAGTTATCA AGGTCAAAAT GGTTTAGCTA TCGGGGTATC AAGAATTTCC
1951  GATAATGGCA AAGTGATTAT TCGCTTGTCT GGCACAACCA ATAGTCAAGG
2001  TAAAACAGGC GTTGCAGCAG GTGTTGGTTA CCAGTGG
```

FIG._14B

|     |            |            |            |            |            |
|-----|------------|------------|------------|------------|------------|
| 1   | MNKIFNVIWN | VVTQTWVVVS | ELTRTHTKCA | SATVAVAVLA | TLLSATVQAN |
| 51  | ATDENEDDEE | ELEPVQRSVL | RWSFKSAKEG | TGEQEGTTEV | INLNTDSSGN |
| 101 | AVGSSTITFK | AGDNLKIKQS | GNDFTYSLKK | ELKNLTSVET | EKLSFGANGN |
| 151 | KVDITSDANG | LKLAKTGNGN | GQNSNVHLNG | IASTLTDTLA | GGTTGHVDTN |
| 201 | IDAVNYHRAA | SVQDVLNSGW | NIQGNGNNVD | FVRTYDTVDF | VNGANANVSV |
| 251 | TADTAHKKTT | VRVDVTGLPV | QYVTEDGKTV | VKVGNEYYKA | KDDGSADMNQ |
| 301 | KVENGELAKT | KVKLVSASGT | NPVKISNVAD | GTEDTDAVSF | KQLKALQDKQ |
| 351 | VTLSTSNAYA | NGGTDNDGGK | ATQTLSNGLN | FKFKSSDGEL | LKISATGDTV |
| 401 | TFTPKKGSVQ | VGDDGKASIS | KGANTTEGLV | EASELVESLN | KLGWKVGVEK |
| 451 | VGSGELDGTS | KETLVKSGDK | VTLKAGDNLK | VKQEGTNFTY | ALKDELTGVK |
| 501 | SVEFKDTANG | ANGASTKITK | DGLTITLANG | ANGATVTDAD | KIKVASDGIS |
| 551 | AGNKAVKNVA | AGEISATSTD | AINGSQLYAV | AKGVTNLAGQ | VNNLEGKVNK |
| 601 | VGKRADAGTA | SALAASQLPQ | ATMPGKSMVS | IAGSSYQGQN | GLAIGVSRIS |
| 651 | DNGKVIIRLS | GTTNSQGKTG | VAAGVGYQW  |            |            |

FIG._15

```
  1 MNKIFNVIWNVVTQTWVVVSELTRTHTKCASATVAVAVLATLLSATVEAN  50
    ||||||||||||||||||||||||||||||||||||||||||||||:||
  1 MNKIFNVIWNVVTQTWVVVSELTRTHTKCASATVAVAVLATLLSATVQAN  50

51 NNTPVTNKLKAYGDANFNFTNNSIADAEKQVQEAYKGLLNLNEKNASDKL 100
                         ..:.  .|.|..::..  :::|.:.  |.|.:
 51 ....................ATDENEDDEEELEPVQRSVLRWSFKSAKEG.  80

101 LVEDNTAATVGNLRKLGWVLSSKNGTRNEKSQQVKHADEVLFEGKGGVQV 150
    .|::....|  ||           ..:.|...   ...:  |.:  :.:.:
 81 TGEQEGTTEVINL..............NTDSSGNAVGSSTITFKAGDNLKI 117

151 TSTSENGKHTITFALAKDLGVKTATVSDTLTIGGGAAAGATTTPKVNVTS 200
    .  .::::    :|:.|  |:|    |..  .:.|.:|:.:.         ||::||
118 KQSGND....FTYSLKKELKNLTSVETEKLSFGANGN.......KVDITS 156

201 TTDGLKFAKDAAGANGDTTVHLNGIGSTLTDTLVGSPATHIDGGDQSTHY 250
    ..:|||:||.:.|....:..|||||:|||||||.|:...|:|..  :..:|
157 DANGLKLAKTGNGNGQNSNVHLNGIASTLTDTLAGGTTGHVDTNIDAVNY 206

251 TRAASIKDVLNAGWNIKGVKAGSTTGQSENVDFVHTYDTVEFLSADTETT 300
    ||||:.||||.||||.           |.:::|||||:|||||:|:.::......
207 HRAASVQDVLNSGWNIQ........GNGNNVDFVRTYDTVDFVNGANANV 248

301 TVTVDSKENGKRTEVKIGAKTSVIKEKDGKLFTGKANKETNKVDGANATE 350
    .||.|.  ..  .  .  |.:.:     .  ..|||   ..    :|.  .    |::.|.
249 SVTADTAHKKTTVRVDVTGLPVQYVTEDGKTVVKVGNEYYKAKDDGSADM 298

351 DADEGKGLVTAKDVIDAVNKTGWRIKTTDANGQNGDFATVA.......SG 393
    :...  :.|  :..  ..|    .  ....  .:|...:...:|  ..|.        :
299 NQKVENGELAKTKVKLVSASGTNPVKISNVADGTEDTDAVSFKQLKALQD 348

394 TNVTFASGNGTTATVTNG.........TDGITVKYDAKVGDGLKLDGDKI 434
    ..||:..:|:  ....|:.         .:|:..|:...  |:  ||:.:
349 KQVTLSTSNAYANGGTDNDGGKATQTLSNGLNFKFKSSDGELLKISA... 395

435 AADTTALTVNDG..KNANNPKGKVADVASTDEKKLVTAKGLVTALNSLSW 482
    .:||..:|...|   .  :::.|:.:....|.|.|    ||.|.:||..||.|:|
396 TGDTVTFTPKKGSVQVGDDGKASISKGANTTE.GLVEASELVESLNKLGW 444

483 TTTAAEADGGTLDGNASEQEVKAGDKVTFKAGKNLKVKQEGANFTYSLQD 532
    ........::|.|||...|    ||.|||||:|||.||||||||.||||.|.|
445 KVGVEKVGSGELDGTSKETLVKSGDKVTLKAGDNLKVKQEGTNFTYALKD 494

533 ALTGLTSITL...GTNNGAKTEINKDGLTIT...PANGAGANNANTISV 576
    .|||:.|:..:     :.|.|||.|.|.|||||||   .||||...::.|.|
495 ELTGVKSVEFKDTANGANGASTKITKDGLTITLANGANGATVTDADKIKV 544

577 TKDGISAGGQSVKNVVSGLKKFGDANFDPLTSSADNLTKQNDDAYKGLTN 626
    ..||||||...||
545 ASDGISAGNKAVK.................................... 557
```

FIG._16A

```
      977 NVANGDISATSTDAINGSQLYAVAKGVTNLAGQVNNLEGKVNKVGKRADA 1026
          |||.|:|||||||||||||||||||||||||||||||||||||||||||
      558 NVAAGEISATSTDAINGSQLYAVAKGVTNLAGQVNNLEGKVNKVGKRADA  607

1027 GTASALAASQLPQATMPGKSMVAIAGSSYQGQNGLAIGVSRISDNGKVII 1076
          |||||||||||||||||||||||||.||||||||||||||||||||||||
      608 GTASALAASQLPQATMPGKSMVSIAGSSYQGQNGLAIGVSRISDNGKVII  657

1077 RLSGTTNSQGKTGVAAGVGYQW 1098
          ||||||||||||||||||||||
      658 RLSGTTNSQGKTGVAAGVGYQW  679
```

FIG._16B

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
       (A) LENGTH: 3294 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 1:

```
ATGAACAAAA TTTTTAACGT TATTTGGAAT GTTGTGACTC AAACTTGGGT TGTCGTATCT      60

GAACTCACTC GCACCCACAC CAAATGCGCC TCCGCCACCG TGGCGGTTGC CGTATTGGCA     120

ACCCTGTTGT CCGCAACGGT TGAGGCGAAC AACAATACTC CTGTTACGAA TAAGTTGAAG     180

GCTTATGGCG ATGCGAATTT TAATTTCACT AATAATTCGA TAGCAGATGC AGAAAAACAA     240

GTTCAAGAGG CTTATAAAGG TTTATTAAAT CTAAATGAAA AAAATGCGAG TGATAAACTG     300

TTGGTGGAGG ACAATACTGC GGCGACCGTA GGCAATTTGC GTAAATTGGG CTGGGTATTG     360

TCTAGCAAAA ACGGCACAAG GAACGAGAAA AGCCAACAAG TCAAACATGC GGATGAAGTG     420

TTGTTTGAAG GCAAAGGCGG TGTGCAGGTT ACTTCCACCT CTGAAAACGG CAAACACACC     480

ATTACCTTTG CTTTAGCGAA AGACCTTGGT GTGAAAACTG CGACTGTGAG TGATACCTTA     540

ACGATTGGCG GTGGTGCTGC TGCAGGTGCT ACAACAACAC CGAAAGTGAA TGTAACTAGT     600

ACAACTGATG GCTTGAAGTT CGCTAAAGAT GCTGCGGGTG CTAATGGCGA TACTACGGTT     660

CACTTGAATG GTATTGGTTC AACCTTGACA GACACGCTTG TGGGTTCTCC TGCTACTCAT     720

ATTGACGGAG GAGATCAAAG TACGCATTAC ACTCGTGCAG CAAGTATCAA GGATGTCTTG     780

AATGCGGGTT GGAATATCAA GGGTGTTAAA GCTGGCTCAA CAACTGGTCA ATCAGAAAAT     840

GTCGATTTTG TTCATACTTA CGATACTGTT GAGTTCTTGA GTGCGGATAC AGAGACCACG     900

ACTGTTACTG TAGATAGCAA AGAAAACGGT AAGAGAACCG AAGTTAAAAT CGGTGCGAAG     960

ACTTCTGTTA TCAAAGAAAA AGACGGTAAG TTATTTACTG GAAAAGCTAA CAAAGAGACA    1020

AATAAAGTTG ATGGTGCTAA CGCGACTGAA GATGCAGACG AAGGCAAAGG CTTAGTGACT    1080

GCGAAAGATG TGATTGACGC AGTGAATAAG ACTGGTTGGA GAATTAAAAC AACCGATGCT    1140

AATGGTCAAA ATGGCGACTT CGCAACTGTT GCATCAGGCA CAAATGTAAC CTTTGCTAGT    1200

GGTAATGGTA CAACTGCGAC TGTAACTAAT GGCACCGATG GTATTACCGT TAAGTATGAT    1260

GCGAAAGTTG GCGACGGCTT AAAAACTAGA TGGCGATAAAA TCGCTGCAGA TACGACCGCA    1320

CTTACTGTGA ATGATGGTAA GAACGCTAAT AATCCGAAAG GTAAAGTGGC TGATGTTGCT    1380

TCAACTGACG AGAAGAAATT GGTTACAGCA AAAGGTTTAG TAACAGCCTT AAACAGTCTA    1440

AGCTGGACTA CAACTGCTGC TGAGGCGGAC GGTGGTACGC TTGATGGAAA TGCAAGTGAG    1500

CAAGAAGTTA AGCGGGCGA TAAAGTAACC TTTAAAGCAG GCAAGAACTT AAAAGTGAAA    1560

CAAGAGGGTG CGAACTTTAC TTATTCACTG CAAGATGCTT TAACAGGCTT AACGAGCATT    1620

ACTTTAGGTA CAGGAAATAA TGGTGCGAAA ACTGAAATCA ACAAAGACGG CTTAACCATC    1680

ACACCAGCAA ATGGTGCGGG TGCAAATAAT GCAAACACCA TCAGCGTAAC CAAAGACGGC    1740

ATTAGTGCGG GCGGTCAGTC GGTTAAAAAC GTTGTGAGCG GACTGAAGAA ATTTGGTGAT    1800
```

```
GCGAATTTCG ATCCGCTGAC TAGCTCCGCC GACAACTTAA CGAAACAAAA TGACGATGCC    1860

TATAAAGGCT TGACCAATTT GGATGAAAAA GGTACAGACA AGCAAACTCC AGTTGTTGCC    1920

GACAATACCG CCGCAACCGT GGGCGATTTG CGCGGCTTGG GCTGGGTCAT TTCTGCGGAC    1980

AAAACCACAG GCGGCTCAAC GGAATATCAC GATCAAGTTC GGAATGCGAA CGAAGTGAAA    2040

TTCAAAAGCG GCAACGGTAT CAATGTTTCC GGTAAAACGG TCAACGGTAG GCGTGAAATT    2100

ACTTTTGAAT TGGCTAAAGG TGAAGTGGTT AAATCGAATG AATTTACCGT CAAAGAAACC    2160

AATGGAAAGG AAACGAGCCT GGTTAAAGTT GGCGATAAAT ATTACAGCAA AGAGGATATT    2220

GACTTAACAA CAGGTCAGCC TAAATTAAAA GATGGCAATA CAGTTGCTGC GAAATATCAA    2280

GATAAAGGTG GCAAAGTCGT TTCTGTAACG GATAATACTG AAGCTACCAT AACCAACAAA    2340

GGTTCTGGCT ATGTAACAGG TAACCAAGTG GCAGATGCGA TTGCGAAATC AGGCTTTGAG    2400

CTTGGCTTGG CTGATGAAGC TGATGCGAAA CGGGCGTTTG ATGATAAGAC AAAAGCCTTA    2460

TCTGCTGGTA CAACGGAAAT TGTAAATGCC CACGATAAAG TCCGTTTTGC TAATGGTTTA    2520

AATACCAAAG TGAGCGCGGC AACGGTGGAA AGCACCGATG CAAACGGCGA TAAAGTGACC    2580

ACAACCTTTG TGAAAACCGA TGTGGAATTG CCTTTAACGC AAATCTACAA TACCGATGCA    2640

AACGGTAAGA AAATCACTAA AGTTGTCAAA GATGGGCAAA CTAAATGGTA TGAACTGAAT    2700

GCTGACGGTA CGGCTGATAT GACCAAAGAA GTTACCCTCG GTAACGTGGA TTCAGACGGC    2760

AAGAAAGTTG TGAAAGACAA CGATGGCAAG TGGTATCACG CCAAAGCTGA CGGTACTGCG    2820

GATAAAACCA AAGGCGAAGT GAGCAATGAT AAAGTTTCTA CCGATGAAAA ACACGTTGTC    2880

AGCCTTGATC CAAATGATCA ATCAAAAGGT AAAGGTGTCG TGATTGACAA TGTGGCTAAT    2940

GGCGATATTT CTGCCACTTC CACCGATGCG ATTAACGGAA GTCAGTTGTA TGCTGTGGCA    3000

AAAGGGGTAA CAAACCTTGC TGGACAAGTG AATAATCTTG AGGGCAAAGT GAATAAAGTG    3060

GGCAAACGTG CAGATGCAGG TACAGCAAGT GCATTAGCGG CTTCACAGTT ACCACAAGCC    3120

ACTATGCCAG GTAAATCAAT GGTTGCTATT GCGGGAAGTA GTTATCAAGG TCAAAATGGT    3180

TTAGCTATCG GGGTATCAAG AATTTCCGAT AATGGCAAAG TGATTATTCG CTTGTCAGGC    3240

ACAACCAATA GTCAAGGTAA AACAGGCGTT GCAGCAGGTG TTGGTTACCA GTGG         3294

(2) INFORMATION FOR SEQ ID NO: 2:

(i) SEQUENCE CHARACTERISTICS:
        (A) LENGTH: 1098 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 2:

Met Asn Lys Ile Phe Asn Val Ile Trp Asn Val Val Thr Gln Thr Trp
1               5                   10                  15

Val Val Val Ser Glu Leu Thr Arg Thr His Thr Lys Cys Ala Ser Ala
            20                  25                  30

Thr Val Ala Val Ala Val Leu Ala Thr Leu Leu Ser Ala Thr Val Glu
        35                  40                  45

Ala Asn Asn Asn Thr Pro Val Thr Asn Lys Leu Lys Ala Tyr Gly Asp
    50                  55                  60

Ala Asn Phe Asn Phe Thr Asn Asn Ser Ile Ala Asp Ala Glu Lys Gln
65                  70                  75                  80
```

-continued

```
Val Gln Glu Ala Tyr Lys Gly Leu Leu Asn Leu Asn Glu Lys Asn Ala
                85                  90                  95
Ser Asp Lys Leu Leu Val Glu Asp Asn Thr Ala Ala Thr Val Gly Asn
            100                 105                 110
Leu Arg Lys Leu Gly Trp Val Leu Ser Lys Asn Gly Thr Arg Asn
        115                 120                 125
Glu Lys Ser Gln Gln Val Lys His Ala Asp Glu Val Leu Phe Glu Gly
    130                 135                 140
Lys Gly Gly Val Gln Val Thr Ser Thr Ser Glu Asn Gly Lys His Thr
145                 150                 155                 160
Ile Thr Phe Ala Leu Ala Lys Asp Leu Gly Val Lys Thr Ala Thr Val
                165                 170                 175
Ser Asp Thr Leu Thr Ile Gly Gly Ala Ala Ala Gly Ala Thr Thr
            180                 185                 190
Thr Pro Lys Val Asn Val Thr Ser Thr Asp Gly Leu Lys Phe Ala
            195                 200                 205
Lys Asp Ala Ala Gly Ala Asn Gly Asp Thr Thr Val His Leu Asn Gly
210                 215                 220
Ile Gly Ser Thr Leu Thr Asp Thr Leu Val Gly Ser Pro Ala Thr His
225                 230                 235                 240
Ile Asp Gly Gly Asp Gln Ser Thr His Tyr Thr Arg Ala Ala Ser Ile
                245                 250                 255
Lys Asp Val Leu Asn Ala Gly Trp Asn Ile Lys Gly Val Lys Ala Gly
            260                 265                 270
Ser Thr Thr Gly Gln Ser Glu Asn Val Asp Phe Val His Thr Tyr Asp
        275                 280                 285
Thr Val Glu Phe Leu Ser Ala Asp Thr Glu Thr Thr Val Thr Val
    290                 295                 300
Asp Ser Lys Glu Asn Gly Lys Arg Thr Glu Val Lys Ile Gly Ala Lys
305                 310                 315                 320
Thr Ser Val Ile Lys Glu Lys Asp Gly Lys Leu Phe Thr Gly Lys Ala
                325                 330                 335
Asn Lys Glu Thr Asn Lys Val Asp Gly Ala Asn Ala Thr Glu Asp Ala
            340                 345                 350
Asp Glu Gly Lys Gly Leu Val Thr Ala Lys Asp Val Ile Asp Ala Val
        355                 360                 365
Asn Lys Thr Gly Trp Arg Ile Lys Thr Thr Asp Ala Asn Gly Gln Asn
    370                 375                 380
Gly Asp Phe Ala Thr Val Ala Ser Gly Thr Asn Val Thr Phe Ala Ser
385                 390                 395                 400
Gly Asn Gly Thr Thr Ala Thr Val Thr Asn Gly Thr Asp Gly Ile Thr
                405                 410                 415
Val Lys Tyr Asp Ala Lys Val Gly Asp Gly Leu Lys Leu Asp Gly Asp
            420                 425                 430
Lys Ile Ala Ala Asp Thr Thr Ala Leu Thr Val Asn Asp Gly Lys Asn
        435                 440                 445
Ala Asn Asn Pro Lys Gly Lys Val Ala Asp Val Ala Ser Thr Asp Glu
    450                 455                 460
Lys Lys Leu Val Thr Ala Lys Gly Leu Val Thr Ala Leu Asn Ser Leu
465                 470                 475                 480
Ser Trp Thr Thr Thr Ala Ala Glu Ala Asp Gly Gly Thr Leu Asp Gly
                485                 490                 495
Asn Ala Ser Glu Gln Glu Val Lys Ala Gly Asp Lys Val Thr Phe Lys
```

-continued

```
                500                 505                 510
Ala Gly Lys Asn Leu Lys Val Lys Gln Glu Gly Ala Asn Phe Thr Tyr
            515                 520                 525

Ser Leu Gln Asp Ala Leu Thr Gly Leu Thr Ser Ile Thr Leu Gly Thr
    530                 535                 540

Gly Asn Asn Gly Ala Lys Thr Glu Ile Asn Lys Asp Gly Leu Thr Ile
545                 550                 555                 560

Thr Pro Ala Asn Gly Ala Gly Asn Asn Ala Asn Thr Ile Ser Val
                565                 570                 575

Thr Lys Asp Gly Ile Ser Ala Gly Gly Gln Ser Val Lys Asn Val Val
            580                 585                 590

Ser Gly Leu Lys Lys Phe Gly Asp Ala Asn Phe Asp Pro Leu Thr Ser
    595                 600                 605

Ser Ala Asp Asn Leu Thr Lys Gln Asn Asp Asp Ala Tyr Lys Gly Leu
    610                 615                 620

Thr Asn Leu Asp Glu Lys Gly Thr Asp Lys Gln Thr Pro Val Val Ala
625                 630                 635                 640

Asp Asn Thr Ala Ala Thr Val Gly Asp Leu Arg Gly Leu Gly Trp Val
            645                 650                 655

Ile Ser Ala Asp Lys Thr Thr Gly Gly Ser Thr Glu Tyr His Asp Gln
            660                 665                 670

Val Arg Asn Ala Asn Glu Val Lys Phe Lys Ser Gly Asn Gly Ile Asn
    675                 680                 685

Val Ser Gly Lys Thr Val Asn Gly Arg Arg Glu Ile Thr Phe Glu Leu
    690                 695                 700

Ala Lys Gly Glu Val Val Lys Ser Asn Glu Phe Thr Val Lys Glu Thr
705                 710                 715                 720

Asn Gly Lys Glu Thr Ser Leu Val Lys Val Gly Asp Lys Tyr Tyr Ser
            725                 730                 735

Lys Glu Asp Ile Asp Leu Thr Thr Gly Gln Pro Lys Leu Lys Asp Gly
            740                 745                 750

Asn Thr Val Ala Ala Lys Tyr Gln Asp Lys Gly Gly Lys Val Val Ser
    755                 760                 765

Val Thr Asp Asn Thr Glu Ala Thr Ile Thr Asn Lys Gly Ser Gly Tyr
    770                 775                 780

Val Thr Gly Asn Gln Val Ala Asp Ala Ile Ala Lys Ser Gly Phe Glu
785                 790                 795                 800

Leu Gly Leu Ala Asp Glu Ala Asp Ala Lys Arg Ala Phe Asp Asp Lys
            805                 810                 815

Thr Lys Ala Leu Ser Ala Gly Thr Thr Glu Ile Val Asn Ala His Asp
            820                 825                 830

Lys Val Arg Phe Ala Asn Gly Leu Asn Thr Lys Val Ser Ala Ala Thr
    835                 840                 845

Val Glu Ser Thr Asp Ala Asn Gly Asp Lys Val Thr Thr Phe Val
    850                 855                 860

Lys Thr Asp Val Glu Leu Pro Leu Thr Gln Ile Tyr Asn Thr Asp Ala
865                 870                 875                 880

Asn Gly Lys Lys Ile Thr Lys Val Val Lys Asp Gly Gln Thr Lys Trp
            885                 890                 895

Tyr Glu Leu Asn Ala Asp Gly Thr Ala Asp Met Thr Lys Glu Val Thr
            900                 905                 910

Leu Gly Asn Val Asp Ser Asp Gly Lys Lys Val Val Lys Asp Asn Asp
    915                 920                 925
```

```
Gly Lys Trp Tyr His Ala Lys Ala Asp Gly Thr Ala Asp Lys Thr Lys
        930                 935                 940

Gly Glu Val Ser Asn Asp Lys Val Ser Thr Asp Glu Lys His Val Val
945                 950                 955                 960

Ser Leu Asp Pro Asn Asp Gln Ser Lys Gly Lys Val Val Ile Asp
                965                 970                 975

Asn Val Ala Asn Gly Asp Ile Ser Ala Thr Ser Thr Asp Ala Ile Asn
            980                 985                 990

Gly Ser Gln Leu Tyr Ala Val Ala Lys Gly Val Thr Asn Leu Ala Gly
        995                 1000                1005

Gln Val Asn Asn Leu Glu Gly Lys Val Asn Lys Val Gly Lys Arg Ala
    1010                1015                1020

Asp Ala Gly Thr Ala Ser Ala Leu Ala Ala Ser Gln Leu Pro Gln Ala
1025                1030                1035                1040

Thr Met Pro Gly Lys Ser Met Val Ala Ile Ala Gly Ser Ser Tyr Gln
                1045                1050                1055

Gly Gln Asn Gly Leu Ala Ile Gly Val Ser Arg Ile Ser Asp Asn Gly
            1060                1065                1070

Lys Val Ile Ile Arg Leu Ser Gly Thr Thr Asn Ser Gln Gly Lys Thr
        1075                1080                1085

Gly Val Ala Ala Gly Val Gly Tyr Gln Trp
    1090                1095
```

(2) INFORMATION FOR SEQ ID NO: 3:

(i) SEQUENCE CHARACTERISTICS:
        (A) LENGTH: 7291 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 163..7221

(xi) SEQUENCE DESCRIPTION: SEQ ID NO: 3:

```
TTTNTTTTTC TTATTTTTTT TTTTTTTTTT TTTTTTTTTT TTGAGGCTAA ACTTTTNGNA    60

AAATATCACT TTTTTATTCT CCAAATATAG AATAGAATAC GCACGATTTC ACTAAGAAAA   120

GTATATTTAT CATTAATTTT ATTAAATATA AGGTAAATAA AA ATG AAC AAA ATT      174
                                               Met Asn Lys Ile
                                                 1

TTT AAC GTT ATT TGG AAT GTT ATG ACT CAA ACT TGG GTT GTC GTA TCT     222
Phe Asn Val Ile Trp Asn Val Met Thr Gln Thr Trp Val Val Val Ser
  5              10                  15                  20

GAA CTC ACT CGC ACC CAC ACC AAA CGC GCC TCC GCA ACC GTG GAG ACC     270
Glu Leu Thr Arg Thr His Thr Lys Arg Ala Ser Ala Thr Val Glu Thr
                25                  30                  35

GCC GTA TTG GCG ACA CTG TTG TTT GCA ACG GTT CAG GCG AAT GCT ACC     318
Ala Val Leu Ala Thr Leu Leu Phe Ala Thr Val Gln Ala Asn Ala Thr
            40                  45                  50

GAT GAA GAT GAA GAG TTA GAC CCC GTA GTA CGC ACT GCT CCC GTG TTG     366
Asp Glu Asp Glu Glu Leu Asp Pro Val Val Arg Thr Ala Pro Val Leu
        55                  60                  65

AGC TTC CAT TCC GAT AAA GAA GGC ACG GGA GAA AAA GAA GTT ACA GAA     414
Ser Phe His Ser Asp Lys Glu Gly Thr Gly Glu Lys Glu Val Thr Glu
    70                  75                  80
```

-continued

```
AAT TCA AAT TGG GGA ATA TAT TTC GAC AAT AAA GGA GTA CTA AAA GCC    462
Asn Ser Asn Trp Gly Ile Tyr Phe Asp Asn Lys Gly Val Leu Lys Ala
 85              90                  95                 100

GGA GCA ATC ACC CTC AAA GCC GGC GAC AAC CTG AAA ATC AAA CAA AAC    510
Gly Ala Ile Thr Leu Lys Ala Gly Asp Asn Leu Lys Ile Lys Gln Asn
             105                 110                 115

ACC GAT GAA AGC ACC AAT GCC AGT AGC TTC ACC TAC TCG CTG AAA AAA    558
Thr Asp Glu Ser Thr Asn Ala Ser Ser Phe Thr Tyr Ser Leu Lys Lys
         120                 125                 130

GAC CTC ACA GAT CTG ACC AGT GTT GCA ACT GAA AAA TTA TCG TTT GGC    606
Asp Leu Thr Asp Leu Thr Ser Val Ala Thr Glu Lys Leu Ser Phe Gly
     135                 140                 145

GCA AAC GGC GAT AAA GTT GAT ATT ACC AGT GAT GCA AAT GGC TTG AAA    654
Ala Asn Gly Asp Lys Val Asp Ile Thr Ser Asp Ala Asn Gly Leu Lys
 150                 155                 160

TTG GCG AAA ACA GGT AAC GGA AAT GTT CAT TTG AAT GGT TTG GAT TCA    702
Leu Ala Lys Thr Gly Asn Gly Asn Val His Leu Asn Gly Leu Asp Ser
165             170                 175                 180

ACT TTG CCT GAT GCG GTA ACG AAT ACA GGT GTG TTA AGT TCA TCA AGT    750
Thr Leu Pro Asp Ala Val Thr Asn Thr Gly Val Leu Ser Ser Ser Ser
             185                 190                 195

TTT ACA CCT AAT GAT GTT GAA AAA ACA AGA GCT GCA ACT GTT AAA GAT    798
Phe Thr Pro Asn Asp Val Glu Lys Thr Arg Ala Ala Thr Val Lys Asp
         200                 205                 210

GTT TTA AAT GCA GGT TGG AAC ATT AAA GGT GCT AAA ACT GCT GGA GGT    846
Val Leu Asn Ala Gly Trp Asn Ile Lys Gly Ala Lys Thr Ala Gly Gly
     215                 220                 225

AAT GTT GAG AGT GTT GAT TTA GTG TCC GCT TAT AAT AAT GTT GAA TTT    894
Asn Val Glu Ser Val Asp Leu Val Ser Ala Tyr Asn Asn Val Glu Phe
 230                 235                 240

ATT ACA GGC GAT AAA AAC ACG CTT GAT GTT GTA TTA ACA GCT AAA GAA    942
Ile Thr Gly Asp Lys Asn Thr Leu Asp Val Val Leu Thr Ala Lys Glu
245             250                 255                 260

AAC GGT AAA ACA ACC GAA GTG AAA TTC ACA CCG AAA ACC TCT GTT ATC    990
Asn Gly Lys Thr Thr Glu Val Lys Phe Thr Pro Lys Thr Ser Val Ile
             265                 270                 275

AAA GAA AAA GAC GGT AAG TTA TTT ACT GGA AAA GAG AAT AAC GAC ACA   1038
Lys Glu Lys Asp Gly Lys Leu Phe Thr Gly Lys Glu Asn Asn Asp Thr
         280                 285                 290

AAT AAA GTT ACA AGT AAC ACG GCG ACT GAT AAT ACA GAT GAG GGT AAT   1086
Asn Lys Val Thr Ser Asn Thr Ala Thr Asp Asn Thr Asp Glu Gly Asn
     295                 300                 305

GGC TTA GTC ACT GCA AAA GCT GTG ATT GAT GCT GTG AAC AAG GCT GGT   1134
Gly Leu Val Thr Ala Lys Ala Val Ile Asp Ala Val Asn Lys Ala Gly
 310                 315                 320

TGG AGA GTT AAA ACA ACT ACT GCT AAT GGT CAA AAT GGC GAC TTC GCA   1182
Trp Arg Val Lys Thr Thr Thr Ala Asn Gly Gln Asn Gly Asp Phe Ala
325             330                 335                 340

ACT GTT GCG TCA GGC ACA AAT GTA ACC TTT GAA AGT GGC GAT GGT ACA   1230
Thr Val Ala Ser Gly Thr Asn Val Thr Phe Glu Ser Gly Asp Gly Thr
             345                 350                 355

ACA GCG TCA GTA ACT AAA GAT ACT AAC GGC AAT GGC ATC ACT GTT AAG   1278
Thr Ala Ser Val Thr Lys Asp Thr Asn Gly Asn Gly Ile Thr Val Lys
         360                 365                 370

TAC GAC GCG AAA GTT GGC GAC GGC TTG AAA TTT GAT AGC GAT AAA AAA   1326
Tyr Asp Ala Lys Val Gly Asp Gly Leu Lys Phe Asp Ser Asp Lys Lys
     375                 380                 385

ATC GTT GCA GAT ACG ACC GCA CTT ACT GTG ACA GGT GGT AAG GTA GCT   1374
Ile Val Ala Asp Thr Thr Ala Leu Thr Val Thr Gly Gly Lys Val Ala
 390                 395                 400
```

-continued

```
GAA ATT GCT AAA GAA GAT GAC AAG AAA AAA CTT GTT AAT GCA GGC GAT        1422
Glu Ile Ala Lys Glu Asp Asp Lys Lys Lys Leu Val Asn Ala Gly Asp
405                 410                 415                 420

TTG GTA ACA GCT TTA GGT AAT CTA AGT TGG AAA GCA AAA GCT GAG GCT        1470
Leu Val Thr Ala Leu Gly Asn Leu Ser Trp Lys Ala Lys Ala Glu Ala
                425                 430                 435

GAT ACT GAT GGT GCG CTT GAG GGG ATT TCA AAA GAC CAA GAA GTC AAA        1518
Asp Thr Asp Gly Ala Leu Glu Gly Ile Ser Lys Asp Gln Glu Val Lys
            440                 445                 450

GCA GGC GAA ACG GTA ACC TTT AAA GCG GGC AAG AAC TTA AAA GTG AAA        1566
Ala Gly Glu Thr Val Thr Phe Lys Ala Gly Lys Asn Leu Lys Val Lys
        455                 460                 465

CAG GAT GGT GCG AAC TTT ACT TAT TCA CTG CAA GAT GCT TTA ACG GGT        1614
Gln Asp Gly Ala Asn Phe Thr Tyr Ser Leu Gln Asp Ala Leu Thr Gly
    470                 475                 480

TTA ACG AGC ATT ACT TTA GGT GGT ACA ACT AAT GGC GGA AAT GAT GCG        1662
Leu Thr Ser Ile Thr Leu Gly Gly Thr Thr Asn Gly Gly Asn Asp Ala
485                 490                 495                 500

AAA ACC GTC ATC AAC AAA GAC GGT TTA ACC ATC ACG CCA GCA GGT AAT        1710
Lys Thr Val Ile Asn Lys Asp Gly Leu Thr Ile Thr Pro Ala Gly Asn
                505                 510                 515

GGC GGT ACG ACA GGT ACA AAC ACC ATC AGC GTA ACC AAA GAT GGC ATT        1758
Gly Gly Thr Thr Gly Thr Asn Thr Ile Ser Val Thr Lys Asp Gly Ile
            520                 525                 530

AAA GCA GGT AAT AAA GCT ATT ACT AAT GTT GCG AGT GGT TTA AGA GCT        1806
Lys Ala Gly Asn Lys Ala Ile Thr Asn Val Ala Ser Gly Leu Arg Ala
        535                 540                 545

TAT GAC GAT GCG AAT TTT GAT GTT TTA AAT AAC TCT GCA ACT GAT TTA        1854
Tyr Asp Asp Ala Asn Phe Asp Val Leu Asn Asn Ser Ala Thr Asp Leu
    550                 555                 560

AAT AGA CAC GTT GAA GAT GCT TAT AAA GGT TTA TTA AAT CTA AAT GAA        1902
Asn Arg His Val Glu Asp Ala Tyr Lys Gly Leu Leu Asn Leu Asn Glu
565                 570                 575                 580

AAA AAT GCA AAT AAA CAA CCG TTG GTG ACT GAC AGC ACG GCG GCG ACT        1950
Lys Asn Ala Asn Lys Gln Pro Leu Val Thr Asp Ser Thr Ala Ala Thr
                585                 590                 595

GTA GGC GAT TTA CGT AAA TTG GGT TGG GTA GTA TCA ACC AAA AAC GGT        1998
Val Gly Asp Leu Arg Lys Leu Gly Trp Val Val Ser Thr Lys Asn Gly
            600                 605                 610

ACG AAA GAA GAA AGC AAT CAA GTT AAA CAA GCT GAT GAA GTC CTC TTT        2046
Thr Lys Glu Glu Ser Asn Gln Val Lys Gln Ala Asp Glu Val Leu Phe
        615                 620                 625

ACC GGA GCC GGT GCT GCT ACG GTT ACT TCC AAA TCT GAA AAC GGT AAA        2094
Thr Gly Ala Gly Ala Ala Thr Val Thr Ser Lys Ser Glu Asn Gly Lys
    630                 635                 640

CAT ACG ATT ACC GTT AGT GTG GCT GAA ACT AAA GCG GAT TGC GGT CTT        2142
His Thr Ile Thr Val Ser Val Ala Glu Thr Lys Ala Asp Cys Gly Leu
645                 650                 655                 660

GAA AAA GAT GGC GAT ACT ATT AAG CTC AAA GTG GAT AAT CAA AAC ACT        2190
Glu Lys Asp Gly Asp Thr Ile Lys Leu Lys Val Asp Asn Gln Asn Thr
                665                 670                 675

GAT AAT GTT TTA ACT GTT GGT AAT AAT GGT ACT GCT GTC ACT AAA GGT        2238
Asp Asn Val Leu Thr Val Gly Asn Asn Gly Thr Ala Val Thr Lys Gly
            680                 685                 690

GGC TTT GAA ACT GTT AAA ACT GGA GCG ACT GAT GCA GAT CGC GGT AAA        2286
Gly Phe Glu Thr Val Lys Thr Gly Ala Thr Asp Ala Asp Arg Gly Lys
        695                 700                 705

GTA ACT GTA AAA GAT GCT ACT GCT AAT GAC GCT GAT AAG AAA GTC GCA        2334
Val Thr Val Lys Asp Ala Thr Ala Asn Asp Ala Asp Lys Lys Val Ala
```

-continued

```
            710                 715                 720
ACT GTA AAA GAT GTT GCA ACC GCA ATT AAT AGT GCG GCG ACT TTT GTG      2382
Thr Val Lys Asp Val Ala Thr Ala Ile Asn Ser Ala Ala Thr Phe Val
725                 730                 735                 740

AAA ACA GAG AAT TTA ACT ACC TCT ATT GAT GAA GAT AAT CCT ACA GAT      2430
Lys Thr Glu Asn Leu Thr Thr Ser Ile Asp Glu Asp Asn Pro Thr Asp
                745                 750                 755

AAC GGC AAA GAT GAC GCA CTT AAA GCG GGC GAT ACC TTA ACC TTT AAA      2478
Asn Gly Lys Asp Asp Ala Leu Lys Ala Gly Asp Thr Leu Thr Phe Lys
            760                 765                 770

GCA GGT AAA AAC CTG AAA GTT AAA CGT GAT GGA AAA AAT ATT ACT TTT      2526
Ala Gly Lys Asn Leu Lys Val Lys Arg Asp Gly Lys Asn Ile Thr Phe
        775                 780                 785

GAC TTG GCG AAA AAC CTT GAG GTG AAA ACT GCG AAA GTG AGT GAT ACT      2574
Asp Leu Ala Lys Asn Leu Glu Val Lys Thr Ala Lys Val Ser Asp Thr
    790                 795                 800

TTA ACG ATT GGC GGG AAT ACA CCT ACA GGT GGC ACT ACT GCG ACG CCA      2622
Leu Thr Ile Gly Gly Asn Thr Pro Thr Gly Gly Thr Thr Ala Thr Pro
805                 810                 815                 820

AAA GTG AAT ATT ACT AGC ACG GCT GAT GGT TTG AAT TTT GCA AAA GAA      2670
Lys Val Asn Ile Thr Ser Thr Ala Asp Gly Leu Asn Phe Ala Lys Glu
                825                 830                 835

ACA GCC GAT GCC TCG GGT TCT AAG AAT GTT TAT TTG AAA GGT ATT GCG      2718
Thr Ala Asp Ala Ser Gly Ser Lys Asn Val Tyr Leu Lys Gly Ile Ala
            840                 845                 850

ACA ACT TTA ACT GAG CCA AGC GCG GGA GCG AAG TCT TCA CAC GTT GAT      2766
Thr Thr Leu Thr Glu Pro Ser Ala Gly Ala Lys Ser Ser His Val Asp
        855                 860                 865

TTA AAT GTG GAT GCG ACG AAA AAA TCC AAT GCA GCA AGT ATT GAA GAT      2814
Leu Asn Val Asp Ala Thr Lys Lys Ser Asn Ala Ala Ser Ile Glu Asp
    870                 875                 880

GTA TTG CGC GCA GGT TGG AAT ATT CAA GGT AAT GGT AAT AAT GTT GAT      2862
Val Leu Arg Ala Gly Trp Asn Ile Gln Gly Asn Gly Asn Asn Val Asp
885                 890                 895                 900

TAT GTA GCG ACG TAT GAC ACA GTA AAC TTT ACC GAT GAC AGC ACA GGT      2910
Tyr Val Ala Thr Tyr Asp Thr Val Asn Phe Thr Asp Asp Ser Thr Gly
                905                 910                 915

ACA ACA ACG GTA ACC GTA ACC CAA AAA GCA GAT GGC AAA GGT GCT GAC      2958
Thr Thr Thr Val Thr Val Thr Gln Lys Ala Asp Gly Lys Gly Ala Asp
            920                 925                 930

GTT AAA ATC GGT GCG AAA ACT TCT GTT ATC AAA GAC CAC AAC GGC AAA      3006
Val Lys Ile Gly Ala Lys Thr Ser Val Ile Lys Asp His Asn Gly Lys
        935                 940                 945

CTG TTT ACA GGC AAA GAC CTG AAA GAT GCG AAT AAT GGT GCA ACC GTT      3054
Leu Phe Thr Gly Lys Asp Leu Lys Asp Ala Asn Asn Gly Ala Thr Val
    950                 955                 960

AGT GAA GAT GAT GGC AAA GAC ACC GGC ACA GGC TTA GTT ACT GCA AAA      3102
Ser Glu Asp Asp Gly Lys Asp Thr Gly Thr Gly Leu Val Thr Ala Lys
965                 970                 975                 980

ACT GTG ATT GAT GCA GTA AAT AAA AGC GGT TGG AGG GTA ACC GGT GAG      3150
Thr Val Ile Asp Ala Val Asn Lys Ser Gly Trp Arg Val Thr Gly Glu
                985                 990                 995

GGC GCG ACT GCC GAA ACC GGT GCA ACC GCC GTG AAT GCG GGT AAC GCT      3198
Gly Ala Thr Ala Glu Thr Gly Ala Thr Ala Val Asn Ala Gly Asn Ala
            1000                1005                1010

GAA ACC GTT ACA TCA GGC ACG AGC GTG AAC TTC AAA AAC GGC AAT GCG      3246
Glu Thr Val Thr Ser Gly Thr Ser Val Asn Phe Lys Asn Gly Asn Ala
        1015                1020                1025

ACC ACA GCG ACC GTA AGC AAA GAT AAT GGC AAC ATC AAT GTC AAA TAC      3294
```

```
                                              -continued

Thr Thr Ala Thr Val Ser Lys Asp Asn Gly Asn Ile Asn Val Lys Tyr
    1030                1035                1040

GAT GTA AAT GTT GGT GAC GGC TTG AAG ATT GGC GAT GAC AAA AAA ATC       3342
Asp Val Asn Val Gly Asp Gly Leu Lys Ile Gly Asp Asp Lys Lys Ile
1045                1050                1055                1060

GTT GCA GAC ACG ACC ACA CTT ACT GTA ACA GGT GGT AAG GTG TCT GTT       3390
Val Ala Asp Thr Thr Thr Leu Thr Val Thr Gly Gly Lys Val Ser Val
                1065                1070                1075

CCT GCT GGT GCT AAT AGT GTT AAT AAC AAT AAG AAA CTT GTT AAT GCA       3438
Pro Ala Gly Ala Asn Ser Val Asn Asn Asn Lys Lys Leu Val Asn Ala
                    1080                1085                1090

GAG GGT TTA GCG ACT GCT TTA AAC AAC CTA AGC TGG ACG GCA AAA GCC       3486
Glu Gly Leu Ala Thr Ala Leu Asn Asn Leu Ser Trp Thr Ala Lys Ala
            1095                1100                1105

GAT AAA TAT GCA GAT GGC GAG TCA GAG GGC GAA ACC GAC CAA GAA GTC       3534
Asp Lys Tyr Ala Asp Gly Glu Ser Glu Gly Glu Thr Asp Gln Glu Val
        1110                1115                1120

AAA GCA GGC GAC AAA GTA ACC TTT AAA GCA GGC AAG AAC TTA AAA GTG       3582
Lys Ala Gly Asp Lys Val Thr Phe Lys Ala Gly Lys Asn Leu Lys Val
1125                1130                1135                1140

AAA CAG TCT GAA AAA GAC TTT ACT TAT TCA CTG CAA GAC ACT TTA ACA       3630
Lys Gln Ser Glu Lys Asp Phe Thr Tyr Ser Leu Gln Asp Thr Leu Thr
                1145                1150                1155

GGC TTA ACG AGC ATT ACT TTA GGT GGT ACA GCT AAT GGC AGA AAT GAT       3678
Gly Leu Thr Ser Ile Thr Leu Gly Gly Thr Ala Asn Gly Arg Asn Asp
            1160                1165                1170

ACG GGA ACC GTC ATC AAC AAA GAC GGC TTA ACC ATC ACG CTG GCA AAT       3726
Thr Gly Thr Val Ile Asn Lys Asp Gly Leu Thr Ile Thr Leu Ala Asn
        1175                1180                1185

GGT GCT GCG GCA GGC ACA GAT GCG TCT AAC GGA AAC ACC ATC AGT GTA       3774
Gly Ala Ala Ala Gly Thr Asp Ala Ser Asn Gly Asn Thr Ile Ser Val
    1190                1195                1200

ACC AAA GAC GGC ATT AGT GCG GGT AAT AAA GAA ATT ACC AAT GTT AAG       3822
Thr Lys Asp Gly Ile Ser Ala Gly Asn Lys Glu Ile Thr Asn Val Lys
1205                1210                1215                1220

AGT GCT TTA AAA ACC TAT AAA GAT ACT CAA AAC ACT GCA GAT GAA ACA       3870
Ser Ala Leu Lys Thr Tyr Lys Asp Thr Gln Asn Thr Ala Asp Glu Thr
                1225                1230                1235

CAA GAT AAA GAG TTC CAC GCC GCC GTT AAA AAC GCA AAT GAA GTT GAG       3918
Gln Asp Lys Glu Phe His Ala Ala Val Lys Asn Ala Asn Glu Val Glu
            1240                1245                1250

TTC GTG GGT AAA AAC GGT GCA ACC GTG TCT GCA AAA ACT GAT AAC AAC       3966
Phe Val Gly Lys Asn Gly Ala Thr Val Ser Ala Lys Thr Asp Asn Asn
        1255                1260                1265

GGA AAA CAT ACT GTA ACG ATT GAT GTT GCA GAA GCC AAA GTT GGT GAT       4014
Gly Lys His Thr Val Thr Ile Asp Val Ala Glu Ala Lys Val Gly Asp
    1270                1275                1280

GGT CTT GAA AAA GAT ACT GAC GGC AAG ATT AAA CTC AAA GTA GAT AAT       4062
Gly Leu Glu Lys Asp Thr Asp Gly Lys Ile Lys Leu Lys Val Asp Asn
1285                1290                1295                1300

ACA GAT GGG AAT AAT CTA TTA ACC GTT GAT GCA ACA AAA GGT GCA TCC       4110
Thr Asp Gly Asn Asn Leu Leu Thr Val Asp Ala Thr Lys Gly Ala Ser
                1305                1310                1315

GTT GCC AAG GGC GAG TTT AAT GCC GTA ACA ACA GAT GCA ACT ACA GCC       4158
Val Ala Lys Gly Glu Phe Asn Ala Val Thr Thr Asp Ala Thr Thr Ala
            1320                1325                1330

CAA GGC ACA AAT GCC AAT GAG CGC GGT AAA GTG GTT GTC AAG GGT TCA       4206
Gln Gly Thr Asn Ala Asn Glu Arg Gly Lys Val Val Val Lys Gly Ser
        1335                1340                1345
```

| | |
|---|---|
| AAT GGT GCA ACT GCT ACC GAA ACT GAC AAG AAA AAA GTG GCA ACT GTT<br>Asn Gly Ala Thr Ala Thr Glu Thr Asp Lys Lys Lys Val Ala Thr Val<br>　　　1350　　　　　　　　　1355　　　　　　　　　1360 | 4254 |
| GGC GAC GTT GCT AAA GCG ATT AAC GAC GCA GCA ACT TTC GTG AAA GTG<br>Gly Asp Val Ala Lys Ala Ile Asn Asp Ala Ala Thr Phe Val Lys Val<br>1365　　　　　　　　　1370　　　　　　　　　1375　　　　　　　　　1380 | 4302 |
| GAA AAT GAC GAC AGT GCT ACG ATT GAT GAT AGC CCA ACA GAT GAT GGC<br>Glu Asn Asp Asp Ser Ala Thr Ile Asp Asp Ser Pro Thr Asp Asp Gly<br>　　　　　　　　　1385　　　　　　　　　1390　　　　　　　　　1395 | 4350 |
| GCA AAT GAT GCT CTC AAA GCA GGC GAC ACC TTG ACC TTA AAA GCG GGT<br>Ala Asn Asp Ala Leu Lys Ala Gly Asp Thr Leu Thr Leu Lys Ala Gly<br>　　　1400　　　　　　　　　1405　　　　　　　　　1410 | 4398 |
| AAA AAC TTA AAA GTT AAA CGT GAT GGT AAA AAT ATT ACT TTT GCC CTT<br>Lys Asn Leu Lys Val Lys Arg Asp Gly Lys Asn Ile Thr Phe Ala Leu<br>　　　　　　　　　1415　　　　　　　　　1420　　　　　　　　　1425 | 4446 |
| GCG AAC GAC CTT AGT GTA AAA AGC GCA ACC GTT AGC GAT AAA TTA TCG<br>Ala Asn Asp Leu Ser Val Lys Ser Ala Thr Val Ser Asp Lys Leu Ser<br>　　　1430　　　　　　　　　1435　　　　　　　　　1440 | 4494 |
| CTT GGT ACA AAC GGC AAT AAA GTC AAT ATC ACA AGC GAC ACC AAA GGC<br>Leu Gly Thr Asn Gly Asn Lys Val Asn Ile Thr Ser Asp Thr Lys Gly<br>1445　　　　　　　　　1450　　　　　　　　　1455　　　　　　　　　1460 | 4542 |
| TTG AAC TTC GCT AAA GAT AGT AAG ACA GGC GAT GAT GCT AAT ATT CAC<br>Leu Asn Phe Ala Lys Asp Ser Lys Thr Gly Asp Asp Ala Asn Ile His<br>　　　　　　　　　1465　　　　　　　　　1470　　　　　　　　　1475 | 4590 |
| TTA AAT GGC ATT GCT TCA ACT TTA ACT GAT ACA TTG TTA AAT AGT GGT<br>Leu Asn Gly Ile Ala Ser Thr Leu Thr Asp Thr Leu Leu Asn Ser Gly<br>　　　1480　　　　　　　　　1485　　　　　　　　　1490 | 4638 |
| GCG ACA ACC AAT TTA GGT GGT AAT GGT ATT ACT GAT AAC GAG AAA AAA<br>Ala Thr Thr Asn Leu Gly Gly Asn Gly Ile Thr Asp Asn Glu Lys Lys<br>　　　　　　　　　1495　　　　　　　　　1500　　　　　　　　　1505 | 4686 |
| CGC GCG GCG AGC GTT AAA GAT GTC TTG AAT GCG GGT TGG AAT GTT CGT<br>Arg Ala Ala Ser Val Lys Asp Val Leu Asn Ala Gly Trp Asn Val Arg<br>　　　1510　　　　　　　　　1515　　　　　　　　　1520 | 4734 |
| GGT GTT AAA CCG GCA TCT GCA AAT AAT CAA GTG GAG AAT ATC GAC TTT<br>Gly Val Lys Pro Ala Ser Ala Asn Asn Gln Val Glu Asn Ile Asp Phe<br>1525　　　　　　　　　1530　　　　　　　　　1535　　　　　　　　　1540 | 4782 |
| GTA GCA ACC TAC GAC ACA GTG GAC TTT GTT AGT GGA GAT AAA GAC ACC<br>Val Ala Thr Tyr Asp Thr Val Asp Phe Val Ser Gly Asp Lys Asp Thr<br>　　　　　　　　　1545　　　　　　　　　1550　　　　　　　　　1555 | 4830 |
| ACG AGT GTA ACT GTT GAA AGT AAA GAT AAT GGC AAG AGA ACC GAA GTT<br>Thr Ser Val Thr Val Glu Ser Lys Asp Asn Gly Lys Arg Thr Glu Val<br>　　　1560　　　　　　　　　1565　　　　　　　　　1570 | 4878 |
| AAA ATC GGT GCG AAG ACT TCT GTT ATC AAA GAC CAC AAC GGC AAA CTG<br>Lys Ile Gly Ala Lys Thr Ser Val Ile Lys Asp His Asn Gly Lys Leu<br>　　　　　　　　　1575　　　　　　　　　1580　　　　　　　　　1585 | 4926 |
| TTT ACA GGC AAA GAG CTG AAG GAT GCT AAC AAT AAT GGC GTA ACT GTT<br>Phe Thr Gly Lys Glu Leu Lys Asp Ala Asn Asn Asn Gly Val Thr Val<br>　　　1590　　　　　　　　　1595　　　　　　　　　1600 | 4974 |
| ACC GAA ACC GAC GGC AAA GAC GAG GGT AAT GGT TTA GTG ACT GCA AAA<br>Thr Glu Thr Asp Gly Lys Asp Glu Gly Asn Gly Leu Val Thr Ala Lys<br>1605　　　　　　　　　1610　　　　　　　　　1615　　　　　　　　　1620 | 5022 |
| GCT GTG ATT GAT GCC GTG AAT AAG GCT GGT TGG AGA GTT AAA ACA ACA<br>Ala Val Ile Asp Ala Val Asn Lys Ala Gly Trp Arg Val Lys Thr Thr<br>　　　　　　　　　1625　　　　　　　　　1630　　　　　　　　　1635 | 5070 |
| GGT GCT AAT GGT CAG AAT GAT GAC TTC GCA ACT GTT GCG TCA GGC ACA<br>Gly Ala Asn Gly Gln Asn Asp Asp Phe Ala Thr Val Ala Ser Gly Thr<br>　　　1640　　　　　　　　　1645　　　　　　　　　1650 | 5118 |
| AAT GTA ACC TTT GCT GAT GGT AAT GGC ACA ACT GCC GAA GTA ACT AAA<br>Asn Val Thr Phe Ala Asp Gly Asn Gly Thr Thr Ala Glu Val Thr Lys<br>　　　　　　　　　1655　　　　　　　　　1660　　　　　　　　　1665 | 5166 |

```
GCA AAC GAC GGT AGT ATT ACT GTT AAA TAC AAT GTT AAA GTG GCT GAT      5214
Ala Asn Asp Gly Ser Ile Thr Val Lys Tyr Asn Val Lys Val Ala Asp
    1670                1675                1680

GGC TTA AAA CTA GAC GGC GAT AAA ATC GTT GCA GAC ACG ACC GTA CTT      5262
Gly Leu Lys Leu Asp Gly Asp Lys Ile Val Ala Asp Thr Thr Val Leu
1685                1690                1695                1700

ACT GTG GCA GAT GGT AAA GTT ACA GCT CCG AAT AAT GGC GAT GGT AAG      5310
Thr Val Ala Asp Gly Lys Val Thr Ala Pro Asn Asn Gly Asp Gly Lys
                1705                1710                1715

AAA TTT GTT GAT GCA AGT GGT TTA GCG GAT GCG TTA AAT AAA TTA AGC      5358
Lys Phe Val Asp Ala Ser Gly Leu Ala Asp Ala Leu Asn Lys Leu Ser
            1720                1725                1730

TGG ACG GCA ACT GCT GGT AAA GAA GGC ACT GGT GAA GTT GAT CCT GCA      5406
Trp Thr Ala Thr Ala Gly Lys Glu Gly Thr Gly Glu Val Asp Pro Ala
        1735                1740                1745

AAT TCA GCA GGG CAA GAA GTC AAA GCG GGC GAC AAA GTA ACC TTT AAA      5454
Asn Ser Ala Gly Gln Glu Val Lys Ala Gly Asp Lys Val Thr Phe Lys
    1750                1755                1760

GCC GGC GAC AAC CTG AAA ATC AAA CAA AGC GGC AAA GAC TTT ACC TAC      5502
Ala Gly Asp Asn Leu Lys Ile Lys Gln Ser Gly Lys Asp Phe Thr Tyr
1765                1770                1775                1780

TCG CTG AAA AAA GAG CTG AAA GAC CTG ACC AGC GTA GAG TTC AAA GAC      5550
Ser Leu Lys Lys Glu Leu Lys Asp Leu Thr Ser Val Glu Phe Lys Asp
                1785                1790                1795

GCA AAC GGC GGT ACA GGC AGT GAA AGC ACC AAG ATT ACC AAA GAC GGC      5598
Ala Asn Gly Gly Thr Gly Ser Glu Ser Thr Lys Ile Thr Lys Asp Gly
                1800                1805                1810

TTG ACC ATT ACG CCG GCA AAC GGT GCG GGT GCG GCA GGT GCA AAC ACT      5646
Leu Thr Ile Thr Pro Ala Asn Gly Ala Gly Ala Ala Gly Ala Asn Thr
            1815                1820                1825

GCA AAC ACC ATT AGC GTA ACC AAA GAT GGC ATT AGC GCG GGT AAT AAA      5694
Ala Asn Thr Ile Ser Val Thr Lys Asp Gly Ile Ser Ala Gly Asn Lys
        1830                1835                1840

GCA GTT ACA AAC GTT GTG AGC GGA CTG AAG AAA TTT GGT GAT GGT CAT      5742
Ala Val Thr Asn Val Val Ser Gly Leu Lys Lys Phe Gly Asp Gly His
1845                1850                1855                1860

ACG TTG GCA AAT GGC ACT GTT GCT GAT TTT GAA AAG CAT TAT GAC AAT      5790
Thr Leu Ala Asn Gly Thr Val Ala Asp Phe Glu Lys His Tyr Asp Asn
                1865                1870                1875

GCC TAT AAA GAC TTG ACC AAT TTG GAT GAA AAA GGC GCG GAT AAT AAT      5838
Ala Tyr Lys Asp Leu Thr Asn Leu Asp Glu Lys Gly Ala Asp Asn Asn
            1880                1885                1890

CCG ACT GTT GCC GAC AAT ACC GCT GCA ACC GTG GGC GAT TTG CGC GGC      5886
Pro Thr Val Ala Asp Asn Thr Ala Ala Thr Val Gly Asp Leu Arg Gly
        1895                1900                1905

TTG GGC TGG GTC ATT TCT GCG GAC AAA ACC ACA GGC GAA CCC AAT CAG      5934
Leu Gly Trp Val Ile Ser Ala Asp Lys Thr Thr Gly Glu Pro Asn Gln
1910                1915                1920

GAA TAC AAC GCG CAA GTG CGT AAC GCC AAT GAA GTG AAA TTC AAG AGC      5982
Glu Tyr Asn Ala Gln Val Arg Asn Ala Asn Glu Val Lys Phe Lys Ser
1925                1930                1935                1940

GGC AAC GGT ATC AAT GTT TCC GGT AAA ACA TTG AAC GGT ACG CGC GTG      6030
Gly Asn Gly Ile Asn Val Ser Gly Lys Thr Leu Asn Gly Thr Arg Val
                1945                1950                1955

ATT ACC TTT GAA TTG GCT AAA GGC GAA GTG GTT AAA TCG AAT GAA TTT      6078
Ile Thr Phe Glu Leu Ala Lys Gly Glu Val Val Lys Ser Asn Glu Phe
            1960                1965                1970

ACC GTT AAG AAT GCC GAT GGT TCG GAA ACG AAC TTG GTT AAA GTT GGC      6126
Thr Val Lys Asn Ala Asp Gly Ser Glu Thr Asn Leu Val Lys Val Gly
```

-continued

```
                1975                1980                1985
GAT ATG TAT TAC AGC AAA GAG GAT ATT GAC CCG GCA ACC AGT AAA CCG       6174
Asp Met Tyr Tyr Ser Lys Glu Asp Ile Asp Pro Ala Thr Ser Lys Pro
    1990                1995                2000

ATG ACA GGT AAA ACT GAA AAA TAT AAG GTT GAA AAC GGC AAA GTC GTT       6222
Met Thr Gly Lys Thr Glu Lys Tyr Lys Val Glu Asn Gly Lys Val Val
2005                2010                2015                2020

TCT GCT AAC GGC AGC AAG ACC GAA GTT ACC CTA ACC AAC AAA GGT TCC       6270
Ser Ala Asn Gly Ser Lys Thr Glu Val Thr Leu Thr Asn Lys Gly Ser
            2025                2030                2035

GGC TAT GTA ACA GGT AAC CAA GTG GCT GAT GCG ATT GCG AAA TCA GGC       6318
Gly Tyr Val Thr Gly Asn Gln Val Ala Asp Ala Ile Ala Lys Ser Gly
                2040                2045                2050

TTT GAG CTT GGT TTG GCT GAT GCG GCA GAA GCT GAA AAA GCC TTT GCA       6366
Phe Glu Leu Gly Leu Ala Asp Ala Ala Glu Ala Glu Lys Ala Phe Ala
            2055                2060                2065

GAA AGC GCA AAA GAC AAG CAA TTG TCT AAA GAT AAA GCG GAA ACT GTA       6414
Glu Ser Ala Lys Asp Lys Gln Leu Ser Lys Asp Lys Ala Glu Thr Val
                2070                2075                2080

AAT GCC CAC GAT AAA GTC CGT TTT GCT AAT GGT TTA AAT ACC AAA GTG       6462
Asn Ala His Asp Lys Val Arg Phe Ala Asn Gly Leu Asn Thr Lys Val
2085                2090                2095                2100

AGC GCG GCA ACG GTG GAA AGC ACT GAT GCA AAC GGC GAT AAA GTG ACC       6510
Ser Ala Ala Thr Val Glu Ser Thr Asp Ala Asn Gly Asp Lys Val Thr
            2105                2110                2115

ACA ACC TTT GTG AAA ACC GAT GTG GAA TTG CCT TTA ACG CAA ATC TAC       6558
Thr Thr Phe Val Lys Thr Asp Val Glu Leu Pro Leu Thr Gln Ile Tyr
                2120                2125                2130

AAT ACC GAT GCA AAC GGT AAT AAG ATC GTT AAA AAA GCT GAC GGA AAA       6606
Asn Thr Asp Ala Asn Gly Asn Lys Ile Val Lys Lys Ala Asp Gly Lys
            2135                2140                2145

TGG TAT GAA CTG AAT GCT GAT GGT ACG GCG AGT AAC AAA GAA GTG ACA       6654
Trp Tyr Glu Leu Asn Ala Asp Gly Thr Ala Ser Asn Lys Glu Val Thr
                2150                2155                2160

CTT GGT AAC GTG GAT GCA AAC GGT AAG AAA GTT GTG AAA GTA ACC GAA       6702
Leu Gly Asn Val Asp Ala Asn Gly Lys Lys Val Val Lys Val Thr Glu
2165                2170                2175                2180

AAT GGT GCG GAT AAG TGG TAT TAC ACC AAT GCT GAC GGT GCT GCG GAT       6750
Asn Gly Ala Asp Lys Trp Tyr Tyr Thr Asn Ala Asp Gly Ala Ala Asp
            2185                2190                2195

AAA ACC AAA GGC GAA GTG AGC AAT GAT AAA GTT TCT ACC GAT GAA AAA       6798
Lys Thr Lys Gly Glu Val Ser Asn Asp Lys Val Ser Thr Asp Glu Lys
                2200                2205                2210

CAC GTT GTC CGC CTT GAT CCG AAC AAT CAA TCG AAC GGC AAA GGC GTG       6846
His Val Val Arg Leu Asp Pro Asn Asn Gln Ser Asn Gly Lys Gly Val
            2215                2220                2225

GTC ATT GAC AAT GTG GCT AAT GGC GAA ATT TCT GCC ACT TCC ACC GAT       6894
Val Ile Asp Asn Val Ala Asn Gly Glu Ile Ser Ala Thr Ser Thr Asp
                2230                2235                2240

GCG ATT AAC GGA AGT CAG TTG TAT GCC GTG GCA AAA GGG GTA ACA AAC       6942
Ala Ile Asn Gly Ser Gln Leu Tyr Ala Val Ala Lys Gly Val Thr Asn
2245                2250                2255                2260

CTT GCT GGA CAA GTG AAT AAT CTT GAG GGC AAA GTG AAT AAA GTG GGC       6990
Leu Ala Gly Gln Val Asn Asn Leu Glu Gly Lys Val Asn Lys Val Gly
            2265                2270                2275

AAA CGT GCA GAT GCA GGT ACA GCA AGT GCA TTA GCG GCT TCA CAG TTA       7038
Lys Arg Ala Asp Ala Gly Thr Ala Ser Ala Leu Ala Ala Ser Gln Leu
                2280                2285                2290

CCA CAA GCC ACT ATG CCA GGT AAA TCA ATG GTT GCT ATT GCG GGA AGT       7086
Pro Gln Ala Thr Met Pro Gly Lys Ser Met Val Ala Ile Ala Gly Ser
```

```
Pro Gln Ala Thr Met Pro Gly Lys Ser Met Val Ala Ile Ala Gly Ser
        2295                2300                2305

AGT TAT CAA GGT CAA AAT GGT TTA GCT ATC GGG GTA TCA AGA ATT TCC     7134
Ser Tyr Gln Gly Gln Asn Gly Leu Ala Ile Gly Val Ser Arg Ile Ser
    2310                2315                2320

GAT AAT GGC AAA GTG ATT ATT CGC TTG TCA GGC ACA ACC AAT AGT CAA     7182
Asp Asn Gly Lys Val Ile Ile Arg Leu Ser Gly Thr Thr Asn Ser Gln
2325            2330                2335                2340

GGT AAA ACA GGC GTT GCA GCA GGT GTT GGT TAC CAG TGG TAAAGTTTGG      7231
Gly Lys Thr Gly Val Ala Ala Gly Val Gly Tyr Gln Trp
                2345                2350

ATTATCTCTC TTAAAAAGCG GCATTTGCCG CTTTTTTTAT GGGTGGCTAT TATGTATCGT   7291

(2) INFORMATION FOR SEQ ID NO: 4:

(i) SEQUENCE CHARACTERISTICS:
        (A) LENGTH: 2353 amino acids
        (B) TYPE: amino acid
        (D) TOPOLOGY: linear (ii) MOLECULE TYPE: protein (xi) SEQUENCE DESCRIPTION: SEQ ID NO: 4:

Met Asn Lys Ile Phe Asn Val Ile Trp Asn Val Met Thr Gln Thr Trp
1               5                   10                  15

Val Val Val Ser Glu Leu Thr Arg Thr His Thr Lys Arg Ala Ser Ala
                20                  25                  30

Thr Val Glu Thr Ala Val Leu Ala Thr Leu Leu Phe Ala Thr Val Gln
            35                  40                  45

Ala Asn Ala Thr Asp Glu Asp Glu Glu Leu Asp Pro Val Val Arg Thr
        50                  55                  60

Ala Pro Val Leu Ser Phe His Ser Asp Lys Glu Gly Thr Gly Glu Lys
65                  70                  75                  80

Glu Val Thr Glu Asn Ser Asn Trp Gly Ile Tyr Phe Asp Asn Lys Gly
                85                  90                  95

Val Leu Lys Ala Gly Ala Ile Thr Leu Lys Ala Gly Asp Asn Leu Lys
                100                 105                 110

Ile Lys Gln Asn Thr Asp Glu Ser Thr Asn Ala Ser Ser Phe Thr Tyr
            115                 120                 125

Ser Leu Lys Lys Asp Leu Thr Asp Leu Thr Ser Val Ala Thr Glu Lys
130                 135                 140

Leu Ser Phe Gly Ala Asn Gly Asp Lys Val Asp Ile Thr Ser Asp Ala
145                 150                 155                 160

Asn Gly Leu Lys Leu Ala Lys Thr Gly Asn Gly Asn Val His Leu Asn
                165                 170                 175

Gly Leu Asp Ser Thr Leu Pro Asp Ala Val Thr Asn Thr Gly Val Leu
            180                 185                 190

Ser Ser Ser Ser Phe Thr Pro Asn Asp Val Glu Lys Thr Arg Ala Ala
        195                 200                 205

Thr Val Lys Asp Val Leu Asn Ala Gly Trp Asn Ile Lys Gly Ala Lys
    210                 215                 220

Thr Ala Gly Gly Asn Val Glu Ser Val Asp Leu Val Ser Ala Tyr Asn
225                 230                 235                 240

Asn Val Glu Phe Ile Thr Gly Asp Lys Asn Thr Leu Asp Val Val Leu
                245                 250                 255

Thr Ala Lys Glu Asn Gly Lys Thr Thr Glu Val Lys Phe Thr Pro Lys
                260                 265                 270
```

```
Thr Ser Val Ile Lys Glu Lys Asp Gly Lys Leu Phe Thr Gly Lys Glu
        275                 280                 285

Asn Asn Asp Thr Asn Lys Val Thr Ser Asn Thr Ala Thr Asp Asn Thr
    290                 295                 300

Asp Glu Gly Asn Gly Leu Val Thr Ala Lys Ala Val Ile Asp Ala Val
305                 310                 315                 320

Asn Lys Ala Gly Trp Arg Val Lys Thr Thr Ala Asn Gly Gln Asn
                325                 330                 335

Gly Asp Phe Ala Thr Val Ala Ser Gly Thr Asn Val Thr Phe Glu Ser
            340                 345                 350

Gly Asp Gly Thr Thr Ala Ser Val Thr Lys Asp Thr Asn Gly Asn Gly
        355                 360                 365

Ile Thr Val Lys Tyr Asp Ala Lys Val Gly Asp Gly Leu Lys Phe Asp
    370                 375                 380

Ser Asp Lys Lys Ile Val Ala Asp Thr Thr Ala Leu Thr Val Thr Gly
385                 390                 395                 400

Gly Lys Val Ala Glu Ile Ala Lys Glu Asp Asp Lys Lys Lys Leu Val
                405                 410                 415

Asn Ala Gly Asp Leu Val Thr Ala Leu Gly Asn Leu Ser Trp Lys Ala
            420                 425                 430

Lys Ala Glu Ala Asp Thr Asp Gly Ala Leu Glu Gly Ile Ser Lys Asp
        435                 440                 445

Gln Glu Val Lys Ala Gly Glu Thr Val Thr Phe Lys Ala Gly Lys Asn
    450                 455                 460

Leu Lys Val Lys Gln Asp Gly Ala Asn Phe Thr Tyr Ser Leu Gln Asp
465                 470                 475                 480

Ala Leu Thr Gly Leu Thr Ser Ile Thr Leu Gly Gly Thr Thr Asn Gly
                485                 490                 495

Gly Asn Asp Ala Lys Thr Val Ile Asn Lys Asp Gly Leu Thr Ile Thr
            500                 505                 510

Pro Ala Gly Asn Gly Gly Thr Thr Gly Thr Asn Thr Ile Ser Val Thr
        515                 520                 525

Lys Asp Gly Ile Lys Ala Gly Asn Lys Ala Ile Thr Asn Val Ala Ser
    530                 535                 540

Gly Leu Arg Ala Tyr Asp Asp Ala Asn Phe Asp Val Leu Asn Asn Ser
545                 550                 555                 560

Ala Thr Asp Leu Asn Arg His Val Glu Asp Ala Tyr Lys Gly Leu Leu
                565                 570                 575

Asn Leu Asn Glu Lys Asn Ala Asn Lys Gln Pro Leu Val Thr Asp Ser
            580                 585                 590

Thr Ala Ala Thr Val Gly Asp Leu Arg Lys Leu Gly Trp Val Val Ser
        595                 600                 605

Thr Lys Asn Gly Thr Lys Glu Glu Ser Asn Gln Val Lys Gln Ala Asp
    610                 615                 620

Glu Val Leu Phe Thr Gly Ala Gly Ala Ala Thr Val Thr Ser Lys Ser
625                 630                 635                 640

Glu Asn Gly Lys His Thr Ile Thr Val Ser Val Ala Glu Thr Lys Ala
                645                 650                 655

Asp Cys Gly Leu Glu Lys Asp Gly Asp Thr Ile Lys Leu Lys Val Asp
            660                 665                 670

Asn Gln Asn Thr Asp Asn Val Leu Thr Val Gly Asn Asn Gly Thr Ala
        675                 680                 685
```

```
Val Thr Lys Gly Gly Phe Glu Thr Val Lys Thr Gly Ala Thr Asp Ala
    690             695             700

Asp Arg Gly Lys Val Thr Val Lys Asp Ala Thr Ala Asn Asp Ala Asp
705             710             715             720

Lys Lys Val Ala Thr Val Lys Asp Val Ala Thr Ala Ile Asn Ser Ala
                725             730             735

Ala Thr Phe Val Lys Thr Glu Asn Leu Thr Thr Ser Ile Asp Glu Asp
            740             745             750

Asn Pro Thr Asp Asn Gly Lys Asp Asp Ala Leu Lys Ala Gly Asp Thr
        755             760             765

Leu Thr Phe Lys Ala Gly Lys Asn Leu Lys Val Lys Arg Asp Gly Lys
    770             775             780

Asn Ile Thr Phe Asp Leu Ala Lys Asn Leu Glu Val Lys Thr Ala Lys
785             790             795             800

Val Ser Asp Thr Leu Thr Ile Gly Gly Asn Thr Pro Thr Gly Gly Thr
                805             810             815

Thr Ala Thr Pro Lys Val Asn Ile Thr Ser Thr Ala Asp Gly Leu Asn
            820             825             830

Phe Ala Lys Glu Thr Ala Asp Ala Ser Gly Ser Lys Asn Val Tyr Leu
        835             840             845

Lys Gly Ile Ala Thr Thr Leu Thr Glu Pro Ser Ala Gly Ala Lys Ser
    850             855             860

Ser His Val Asp Leu Asn Val Asp Ala Thr Lys Lys Ser Asn Ala Ala
865             870             875             880

Ser Ile Glu Asp Val Leu Arg Ala Gly Trp Asn Ile Gln Gly Asn Gly
                885             890             895

Asn Asn Val Asp Tyr Val Ala Thr Tyr Asp Thr Val Asn Phe Thr Asp
            900             905             910

Asp Ser Thr Gly Thr Thr Thr Val Thr Val Thr Gln Lys Ala Asp Gly
        915             920             925

Lys Gly Ala Asp Val Lys Ile Gly Ala Lys Thr Ser Val Ile Lys Asp
    930             935             940

His Asn Gly Lys Leu Phe Thr Gly Lys Asp Leu Lys Asp Ala Asn Asn
945             950             955             960

Gly Ala Thr Val Ser Glu Asp Asp Gly Lys Asp Thr Gly Thr Gly Leu
                965             970             975

Val Thr Ala Lys Thr Val Ile Asp Ala Val Asn Lys Ser Gly Trp Arg
            980             985             990

Val Thr Gly Glu Gly Ala Thr Ala Glu Thr Gly Ala Thr Ala Val Asn
        995             1000            1005

Ala Gly Asn Ala Glu Thr Val Thr Ser Gly Thr Ser Val Asn Phe Lys
    1010            1015            1020

Asn Gly Asn Ala Thr Thr Ala Thr Val Ser Lys Asp Asn Gly Asn Ile
1025            1030            1035            1040

Asn Val Lys Tyr Asp Val Asn Val Gly Asp Gly Leu Lys Ile Gly Asp
                1045            1050            1055

Asp Lys Lys Ile Val Ala Asp Thr Thr Thr Leu Thr Val Thr Gly Gly
            1060            1065            1070

Lys Val Ser Val Pro Ala Gly Ala Asn Ser Val Asn Asn Lys Lys
        1075            1080            1085

Leu Val Asn Ala Glu Gly Leu Ala Thr Ala Leu Asn Asn Leu Ser Trp
    1090            1095            1100

Thr Ala Lys Ala Asp Lys Tyr Ala Asp Gly Glu Ser Glu Gly Glu Thr
```

```
                1105              1110              1115              1120
Asp Gln Glu Val Lys Ala Gly Asp Lys Val Thr Phe Lys Ala Gly Lys
                    1125              1130              1135
Asn Leu Lys Val Lys Gln Ser Glu Lys Asp Phe Thr Tyr Ser Leu Gln
                1140              1145              1150
Asp Thr Leu Thr Gly Leu Thr Ser Ile Thr Leu Gly Gly Thr Ala Asn
                1155              1160              1165
Gly Arg Asn Asp Thr Gly Thr Val Ile Asn Lys Asp Gly Leu Thr Ile
            1170              1175              1180
Thr Leu Ala Asn Gly Ala Ala Gly Thr Asp Ala Ser Asn Gly Asn
1185              1190              1195              1200
Thr Ile Ser Val Thr Lys Asp Gly Ile Ser Ala Gly Asn Lys Glu Ile
                1205              1210              1215
Thr Asn Val Lys Ser Ala Leu Lys Thr Tyr Lys Asp Thr Gln Asn Thr
                1220              1225              1230
Ala Asp Glu Thr Gln Asp Lys Glu Phe His Ala Ala Val Lys Asn Ala
                1235              1240              1245
Asn Glu Val Glu Phe Val Gly Lys Asn Gly Ala Thr Val Ser Ala Lys
            1250              1255              1260
Thr Asp Asn Asn Gly Lys His Thr Val Thr Ile Asp Val Ala Glu Ala
1265              1270              1275              1280
Lys Val Gly Asp Gly Leu Glu Lys Asp Thr Asp Gly Lys Ile Lys Leu
                1285              1290              1295
Lys Val Asp Asn Thr Asp Gly Asn Asn Leu Leu Thr Val Asp Ala Thr
                1300              1305              1310
Lys Gly Ala Ser Val Ala Lys Gly Glu Phe Asn Ala Val Thr Thr Asp
                1315              1320              1325
Ala Thr Thr Ala Gln Gly Thr Asn Ala Asn Glu Arg Gly Lys Val Val
                1330              1335              1340
Val Lys Gly Ser Asn Gly Ala Thr Ala Thr Glu Thr Asp Lys Lys Lys
1345              1350              1355              1360
Val Ala Thr Val Gly Asp Val Ala Lys Ala Ile Asn Asp Ala Ala Thr
                1365              1370              1375
Phe Val Lys Val Glu Asn Asp Asp Ser Ala Thr Ile Asp Asp Ser Pro
                1380              1385              1390
Thr Asp Asp Gly Ala Asn Asp Ala Leu Lys Ala Gly Asp Thr Leu Thr
                1395              1400              1405
Leu Lys Ala Gly Lys Asn Leu Lys Val Lys Arg Asp Gly Lys Asn Ile
            1410              1415              1420
Thr Phe Ala Leu Ala Asn Asp Leu Ser Val Lys Ser Ala Thr Val Ser
1425              1430              1435              1440
Asp Lys Leu Ser Leu Gly Thr Asn Gly Asn Lys Val Asn Ile Thr Ser
                1445              1450              1455
Asp Thr Lys Gly Leu Asn Phe Ala Lys Asp Ser Lys Thr Gly Asp Asp
                1460              1465              1470
Ala Asn Ile His Leu Asn Gly Ile Ala Ser Thr Leu Thr Asp Thr Leu
            1475              1480              1485
Leu Asn Ser Gly Ala Thr Thr Asn Leu Gly Gly Asn Gly Ile Thr Asp
            1490              1495              1500
Asn Glu Lys Lys Arg Ala Ala Ser Val Lys Asp Val Leu Asn Ala Gly
1505              1510              1515              1520
Trp Asn Val Arg Gly Val Lys Pro Ala Ser Ala Asn Asn Gln Val Glu
                1525              1530              1535
```

-continued

```
Asn Ile Asp Phe Val Ala Thr Tyr Asp Thr Val Asp Phe Val Ser Gly
         1540                1545                1550

Asp Lys Asp Thr Thr Ser Val Thr Val Glu Ser Lys Asp Asn Gly Lys
    1555                1560                1565

Arg Thr Glu Val Lys Ile Gly Ala Lys Thr Ser Val Ile Lys Asp His
    1570                1575                1580

Asn Gly Lys Leu Phe Thr Gly Lys Glu Leu Lys Asp Ala Asn Asn Asn
1585                1590                1595                1600

Gly Val Thr Val Thr Glu Thr Asp Gly Lys Asp Glu Gly Asn Gly Leu
            1605                1610                1615

Val Thr Ala Lys Ala Val Ile Asp Ala Val Asn Lys Ala Gly Trp Arg
        1620                1625                1630

Val Lys Thr Thr Gly Ala Asn Gly Gln Asn Asp Asp Phe Ala Thr Val
        1635                1640                1645

Ala Ser Gly Thr Asn Val Thr Phe Ala Asp Gly Asn Gly Thr Thr Ala
        1650                1655                1660

Glu Val Thr Lys Ala Asn Asp Gly Ser Ile Thr Val Lys Tyr Asn Val
1665                1670                1675                1680

Lys Val Ala Asp Gly Leu Lys Leu Asp Gly Asp Lys Ile Val Ala Asp
            1685                1690                1695

Thr Thr Val Leu Thr Val Ala Asp Gly Lys Val Thr Ala Pro Asn Asn
        1700                1705                1710

Gly Asp Gly Lys Lys Phe Val Asp Ala Ser Gly Leu Ala Asp Ala Leu
            1715                1720                1725

Asn Lys Leu Ser Trp Thr Ala Thr Ala Gly Lys Glu Gly Thr Gly Glu
    1730                1735                1740

Val Asp Pro Ala Asn Ser Ala Gly Gln Glu Val Lys Ala Gly Asp Lys
1745                1750                1755                1760

Val Thr Phe Lys Ala Gly Asp Asn Leu Lys Ile Lys Gln Ser Gly Lys
            1765                1770                1775

Asp Phe Thr Tyr Ser Leu Lys Lys Glu Leu Lys Asp Leu Thr Ser Val
        1780                1785                1790

Glu Phe Lys Asp Ala Asn Gly Gly Thr Gly Ser Glu Ser Thr Lys Ile
        1795                1800                1805

Thr Lys Asp Gly Leu Thr Ile Thr Pro Ala Asn Gly Ala Gly Ala Ala
    1810                1815                1820

Gly Ala Asn Thr Ala Asn Thr Ile Ser Val Thr Lys Asp Gly Ile Ser
1825                1830                1835                1840

Ala Gly Asn Lys Ala Val Thr Asn Val Ser Gly Leu Lys Lys Phe
        1845                1850                1855

Gly Asp Gly His Thr Leu Ala Asn Gly Thr Val Ala Asp Phe Glu Lys
        1860                1865                1870

His Tyr Asp Asn Ala Tyr Lys Asp Leu Thr Asn Leu Asp Glu Lys Gly
        1875                1880                1885

Ala Asp Asn Asn Pro Thr Val Ala Asp Asn Thr Ala Ala Thr Val Gly
        1890                1895                1900

Asp Leu Arg Gly Leu Gly Trp Val Ile Ser Ala Asp Lys Thr Thr Gly
1905                1910                1915                1920

Glu Pro Asn Gln Glu Tyr Asn Ala Gln Val Arg Asn Ala Asn Glu Val
            1925                1930                1935

Lys Phe Lys Ser Gly Asn Gly Ile Asn Val Ser Gly Lys Thr Leu Asn
        1940                1945                1950
```

-continued

Gly Thr Arg Val Ile Thr Phe Glu Leu Ala Lys Gly Glu Val Val Lys
          1955                1960                1965

Ser Asn Glu Phe Thr Val Lys Asn Ala Asp Gly Ser Glu Thr Asn Leu
    1970                1975                1980

Val Lys Val Gly Asp Met Tyr Tyr Ser Lys Glu Asp Ile Asp Pro Ala
1985                1990                1995                2000

Thr Ser Lys Pro Met Thr Gly Lys Thr Glu Lys Tyr Lys Val Glu Asn
            2005                2010                2015

Gly Lys Val Val Ser Ala Asn Gly Ser Lys Thr Glu Val Thr Leu Thr
                2020                2025                2030

Asn Lys Gly Ser Gly Tyr Val Thr Gly Asn Gln Val Ala Asp Ala Ile
        2035                2040                2045

Ala Lys Ser Gly Phe Glu Leu Gly Leu Ala Asp Ala Ala Glu Ala Glu
    2050                2055                2060

Lys Ala Phe Ala Glu Ser Ala Lys Asp Lys Gln Leu Ser Lys Asp Lys
2065                2070                2075                2080

Ala Glu Thr Val Asn Ala His Asp Lys Val Arg Phe Ala Asn Gly Leu
            2085                2090                2095

Asn Thr Lys Val Ser Ala Ala Thr Val Glu Ser Thr Asp Ala Asn Gly
                2100                2105                2110

Asp Lys Val Thr Thr Thr Phe Val Lys Thr Asp Val Glu Leu Pro Leu
        2115                2120                2125

Thr Gln Ile Tyr Asn Thr Asp Ala Asn Gly Asn Lys Ile Val Lys Lys
    2130                2135                2140

Ala Asp Gly Lys Trp Tyr Glu Leu Asn Ala Asp Gly Thr Ala Ser Asn
2145                2150                2155                2160

Lys Glu Val Thr Leu Gly Asn Val Asp Ala Asn Gly Lys Lys Val Val
            2165                2170                2175

Lys Val Thr Glu Asn Gly Ala Asp Lys Trp Tyr Tyr Thr Asn Ala Asp
                2180                2185                2190

Gly Ala Ala Asp Lys Thr Lys Gly Glu Val Ser Asn Asp Lys Val Ser
        2195                2200                2205

Thr Asp Glu Lys His Val Val Arg Leu Asp Pro Asn Asn Gln Ser Asn
    2210                2215                2220

Gly Lys Gly Val Val Ile Asp Asn Val Ala Asn Gly Glu Ile Ser Ala
2225                2230                2235                2240

Thr Ser Thr Asp Ala Ile Asn Gly Ser Gln Leu Tyr Ala Val Ala Lys
            2245                2250                2255

Gly Val Thr Asn Leu Ala Gly Gln Val Asn Asn Leu Glu Gly Lys Val
                2260                2265                2270

Asn Lys Val Gly Lys Arg Ala Asp Ala Gly Thr Ala Ser Ala Leu Ala
        2275                2280                2285

Ala Ser Gln Leu Pro Gln Ala Thr Met Pro Gly Lys Ser Met Val Ala
    2290                2295                2300

Ile Ala Gly Ser Ser Tyr Gln Gly Gln Asn Gly Leu Ala Ile Gly Val
2305                2310                2315                2320

Ser Arg Ile Ser Asp Asn Gly Lys Val Ile Ile Arg Leu Ser Gly Thr
            2325                2330                2335

Thr Asn Ser Gln Gly Lys Thr Gly Val Ala Ala Gly Val Gly Tyr Gln
                2340                2345                2350

Trp (2) INFORMATION FOR SEQ ID NO: 5:

-continued

```
    (i) SEQUENCE CHARACTERISTICS:
        (A) LENGTH: 658 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 5:

Met Asn Lys Ile Phe Asn Val Ile Trp Asn Val Val Thr Gln Thr Trp
1               5                  10                  15

Val Val Val Ser Glu Leu Thr Arg Thr His Thr Lys Cys Ala Ser Ala
            20                  25                  30

Thr Val Ala Val Ala Val Leu Ala Thr Leu Leu Ser Ala Thr Val Glu
        35                  40                  45

Ala Asn Asn Asn Thr Pro Val Thr Asn Lys Leu Lys Ala Tyr Gly Asp
    50                  55                  60

Ala Asn Phe Asn Phe Thr Asn Asn Ser Ile Ala Asp Ala Glu Lys Gln
65                  70                  75                  80

Val Gln Glu Ala Tyr Lys Gly Leu Leu Asn Leu Asn Glu Lys Asn Ala
                85                  90                  95

Ser Asp Lys Leu Leu Val Glu Asp Asn Thr Ala Ala Thr Val Gly Asn
            100                 105                 110

Leu Arg Lys Leu Gly Trp Val Leu Ser Ser Lys Asn Gly Thr Arg Asn
        115                 120                 125

Glu Lys Ser Gln Gln Val Lys His Ala Asp Glu Val Leu Phe Glu Gly
    130                 135                 140

Lys Gly Gly Val Gln Val Thr Ser Thr Ser Glu Asn Gly Lys His Thr
145                 150                 155                 160

Ile Thr Phe Ala Leu Ala Lys Asp Leu Gly Val Lys Thr Ala Thr Val
                165                 170                 175

Ser Asp Thr Leu Thr Ile Gly Gly Ala Ala Ala Gly Ala Thr Thr
            180                 185                 190

Thr Pro Lys Val Asn Val Thr Ser Thr Asp Gly Leu Lys Phe Ala
        195                 200                 205

Lys Asp Ala Ala Gly Ala Asn Gly Asp Thr Thr Val His Leu Asn Gly
210                 215                 220

Ile Gly Ser Thr Leu Thr Asp Thr Leu Val Gly Ser Pro Ala Thr His
225                 230                 235                 240

Ile Asp Gly Gly Asp Gln Ser Thr His Tyr Thr Arg Ala Ala Ser Ile
                245                 250                 255

Lys Asp Val Leu Asn Ala Gly Trp Asn Ile Lys Gly Val Lys Ala Gly
            260                 265                 270

Ser Thr Thr Gly Gln Ser Glu Asn Val Asp Phe Val His Thr Tyr Asp
        275                 280                 285

Thr Val Glu Phe Leu Ser Ala Asp Thr Glu Thr Thr Val Thr Val
    290                 295                 300

Asp Ser Lys Glu Asn Gly Lys Arg Thr Glu Val Lys Ile Gly Ala Lys
305                 310                 315                 320

Thr Ser Val Ile Lys Glu Lys Asp Gly Lys Leu Phe Thr Gly Lys Ala
                325                 330                 335

Asn Lys Glu Thr Asn Lys Val Asp Gly Ala Asn Ala Thr Glu Asp Ala
            340                 345                 350

Asp Glu Gly Lys Gly Leu Val Thr Ala Lys Asp Val Ile Asp Ala Val
        355                 360                 365
```

```
Asn Lys Thr Gly Trp Arg Ile Lys Thr Thr Asp Ala Asn Gly Gln Asn
    370                 375                 380

Gly Asp Phe Ala Thr Val Ala Ser Gly Thr Asn Val Thr Phe Ala Ser
385                 390                 395                 400

Gly Asn Gly Thr Thr Ala Thr Val Thr Asn Gly Thr Asp Gly Ile Thr
                    405                 410                 415

Val Lys Tyr Asp Ala Lys Val Gly Asp Gly Leu Lys Leu Asp Gly Asp
                420                 425                 430

Lys Ile Ala Ala Asp Thr Thr Ala Leu Thr Val Asn Asp Gly Lys Asn
            435                 440                 445

Ala Asn Asn Pro Lys Gly Lys Val Ala Asp Val Ala Ser Thr Asp Glu
        450                 455                 460

Lys Lys Leu Val Thr Ala Lys Gly Leu Val Thr Ala Leu Asn Ser Leu
465                 470                 475                 480

Ser Trp Thr Thr Thr Ala Ala Glu Ala Asp Gly Gly Thr Leu Asp Gly
                    485                 490                 495

Asn Ala Ser Glu Gln Glu Val Lys Ala Gly Asp Lys Val Thr Phe Lys
                500                 505                 510

Ala Gly Lys Asn Leu Lys Val Lys Gln Glu Gly Ala Asn Phe Thr Tyr
            515                 520                 525

Ser Leu Gln Asp Ala Leu Thr Gly Leu Thr Ser Ile Thr Leu Gly Thr
        530                 535                 540

Gly Asn Asn Gly Ala Lys Thr Glu Ile Asn Lys Asp Gly Leu Thr Ile
545                 550                 555                 560

Thr Pro Ala Asn Gly Ala Gly Ala Asn Asn Ala Asn Thr Ile Ser Val
                    565                 570                 575

Thr Lys Asp Gly Ile Ser Ala Gly Gly Gln Ser Val Lys Asn Val Val
                580                 585                 590

Ser Gly Leu Lys Lys Phe Gly Asp Ala Asn Phe Asp Pro Leu Thr Ser
            595                 600                 605

Ser Ala Asp Asn Leu Thr Lys Gln Asn Asp Asp Ala Tyr Lys Gly Leu
        610                 615                 620

Thr Asn Leu Asp Glu Lys Gly Thr Asp Lys Gln Thr Pro Val Val Ala
625                 630                 635                 640

Asp Asn Thr Ala Ala Thr Val Gly Asp Leu Arg Gly Leu Gly Trp Val
                    645                 650                 655

Ile Ser
```

(2) INFORMATION FOR SEQ ID NO: 6:

(i) SEQUENCE CHARACTERISTICS:
        (A) LENGTH: 607 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 6:

```
Met Asn Lys Ile Phe Asn Val Ile Trp Asn Val Met Thr Gln Thr Trp
1               5                   10                  15

Val Val Val Ser Glu Leu Thr Arg Thr His Thr Lys Arg Leu Arg Asn
                20                  25                  30

Arg Gly Asp Pro Val Leu Ala Thr Leu Leu Phe Ala Thr Val Gln Ala
            35                  40                  45
```

-continued

```
Asn Ala Thr Asp Glu Asp Glu Leu Asp Pro Val Val Arg Thr Ala
     50                  55                  60
Pro Val Leu Ser Phe His Ser Asp Lys Glu Gly Thr Gly Lys Glu
 65                  70                  75                  80
Val Thr Glu Asn Ser Asn Trp Gly Ile Tyr Phe Asp Asn Lys Gly Val
                 85                  90                  95
Leu Lys Ala Gly Ala Ile Thr Leu Lys Ala Gly Asp Asn Leu Lys Xaa
                100                 105                 110
Lys Gln Xaa Thr Asp Glu Xaa Thr Asn Ala Ser Ser Phe Thr Tyr Ser
            115                 120                 125
Leu Lys Lys Asp Leu Thr Asp Leu Thr Ser Val Ala Thr Glu Lys Leu
    130                 135                 140
Ser Phe Gly Ala Asn Gly Asp Lys Val Asp Ile Thr Ser Asp Ala Asn
145                 150                 155                 160
Gly Leu Lys Leu Ala Lys Thr Gly Asn Gly Asn Val His Leu Asn Gly
                165                 170                 175
Leu Asp Ser Thr Leu Pro Asp Ala Val Thr Asn Thr Gly Val Leu Ser
            180                 185                 190
Ser Ser Ser Phe Thr Pro Asn Asp Val Glu Lys Thr Arg Ala Ala Thr
        195                 200                 205
Val Lys Asp Val Leu Asn Ala Gly Trp Asn Ile Lys Gly Ala Lys Thr
    210                 215                 220
Ala Gly Gly Asn Val Glu Ser Val Asp Leu Val Ser Ala Tyr Asn Asn
225                 230                 235                 240
Val Glu Phe Ile Thr Gly Asp Lys Asn Thr Leu Asp Val Val Leu Thr
                245                 250                 255
Ala Lys Glu Asn Xaa Lys Thr Thr Glu Val Lys Phe Thr Pro Lys Thr
            260                 265                 270
Ser Val Ile Lys Glu Lys Asp Gly Lys Leu Phe Thr Gly Lys Glu Asn
        275                 280                 285
Asn Asp Thr Asn Lys Val Thr Ser Asn Thr Ala Thr Asp Asn Thr Asp
    290                 295                 300
Glu Gly Asn Gly Leu Val Thr Ala Lys Ala Val Ile Asp Ala Val Asn
305                 310                 315                 320
Lys Ala Gly Trp Arg Val Lys Thr Thr Thr Ala Asn Gly Gln Asn Gly
                325                 330                 335
Asp Phe Ala Thr Val Ala Ser Gly Thr Asn Val Thr Phe Glu Ser Gly
            340                 345                 350
Asp Gly Thr Thr Ala Ser Val Thr Lys Asp Thr Asn Gly Asn Gly Ile
        355                 360                 365
Thr Val Lys Tyr Asp Ala Lys Val Gly Asp Gly Leu Lys Phe Asp Ser
    370                 375                 380
Asp Lys Lys Ile Val Ala Asp Thr Thr Ala Leu Thr Val Thr Gly Gly
385                 390                 395                 400
Lys Val Ala Glu Ile Ala Lys Glu Asp Asp Lys Lys Leu Val Asn
                405                 410                 415
Ala Gly Asp Leu Val Thr Ala Leu Gly Asn Leu Ser Trp Lys Ala Lys
            420                 425                 430
Ala Glu Ala Asp Thr Asp Gly Ala Leu Glu Gly Ile Ser Lys Asp Gln
        435                 440                 445
Glu Val Lys Ala Gly Glu Thr Val Thr Phe Lys Ala Gly Lys Asn Leu
    450                 455                 460
Lys Val Lys Gln Asp Gly Ala Asn Phe Thr Tyr Ser Leu Gln Asp Ala
```

-continued

```
                465                 470                 475                 480
Leu Thr Gly Leu Thr Ser Ile Thr Leu Gly Gly Thr Thr Asn Gly Gly
                    485                 490                 495
Asn Asp Ala Lys Thr Val Ile Asn Lys Asp Gly Leu Thr Ile Thr Pro
                500                 505                 510
Ala Gly Asn Gly Gly Thr Thr Gly Thr Asn Thr Ile Ser Val Thr Lys
                515                 520                 525
Asp Gly Ile Lys Ala Gly Asn Lys Ala Ile Thr Asn Val Ala Ser Gly
            530                 535                 540
Leu Arg Ala Tyr Asp Asp Ala Asn Phe Asp Val Leu Asn Asn Ser Ala
545                 550                 555                 560
Thr Asp Leu Asn Arg His Val Glu Asp Ala Tyr Lys Gly Leu Leu Asn
                    565                 570                 575
Leu Asn Glu Lys Asn Ala Asn Lys Gln Pro Leu Val Thr Asp Ser Thr
                580                 585                 590
Ala Ala Thr Val Gly Asp Leu Arg Lys Leu Gly Trp Val Val Ser
            595                 600                 605
```

(2) INFORMATION FOR SEQ ID NO: 7:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 7:

```
Met Asn Lys Ile Phe Asn Val Ile Trp Asn Val Met Thr Gln Thr Trp
1               5                   10                  15
Val Val Val Ser Glu Leu Thr Arg
            20
```

(2) INFORMATION FOR SEQ ID NO: 8:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 8:

```
Met Asn Lys Ile Phe Asn Val Ile Trp Asn Val Val Thr Gln Thr Trp
1               5                   10                  15
Val Val Val Ser Glu Leu Thr Arg
            20
```

(2) INFORMATION FOR SEQ ID NO: 9:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 9:

```
Met Asn Lys Ile Tyr Arg Leu Lys Phe Ser Lys Arg Leu Asn Ala Leu
1               5                   10                  15
```

```
Val Ala Val Ser Glu Leu Ala Arg
            20

(2) INFORMATION FOR SEQ ID NO: 10:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 10:

Met Asn Lys Ile Tyr Arg Leu Lys Phe Ser Lys Arg Leu Asn Ala Leu
1               5                   10                  15

Val Ala Val Ser Glu Leu Ala Arg
            20

(2) INFORMATION FOR SEQ ID NO: 11:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 11:

Met Asn Lys Ala Tyr Ser Ile Ile Trp Ser His Ser Arg Gln Ala Trp
1               5                   10                  15

Ile Val Ala Ser Glu Leu Ala Arg
            20

(2) INFORMATION FOR SEQ ID NO: 12:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 12:

Met Asn Arg Ile Tyr Ser Leu Arg Tyr Ser Ala Val Ala Arg Gly Phe
1               5                   10                  15

Ile Ala Val Ser Glu Phe Ala Arg
            20

(2) INFORMATION FOR SEQ ID NO: 13:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 13:

Met Asn Lys Ile Tyr Tyr Leu Lys Tyr Cys His Ile Thr Lys Ser Leu
1               5                   10                  15

Ile Ala Val Ser Glu Leu Ala Arg
            20
```

(2) INFORMATION FOR SEQ ID NO: 14:

(i) SEQUENCE CHARACTERISTICS:
        (A) LENGTH: 2037 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 14:

```
ATGAACAAAA TTTTTAACGT TATTTGGAAT GTTGTGACTC AAACTTGGGT TGTCGTATCT    60
GAACTCACTC GCACCCACAC CAAATGCGCC TCCGCCACCG TGGCAGTTGC CGTATTGGCA   120
ACCCTGTTGT CCGCAACGGT TCAGGCGAAT GCTACCGATG AAAACGAAGA TGATGAAGAA   180
GAGTTAGAAC CCGTACAACG CTCTGTTTTA AGGTGGAGCT TCAAATCCGC TAAGGAAGGC   240
ACTGGAGAAC AAGAGGGAAC AACAGAGGTA ATAAATTTGA ACACAGATTC ATCAGGAAAT   300
GCAGTAGGAA GCAGCACAAT CACCTTCAAA GCCGGCGACA ACCTGAAAAT CAAACAAAGC   360
GGCAATGACT TCACCTACTC GCTGAAAAAA GAGCTGAAAA ACCTGACCAG TGTTGAAACT   420
GAAAAATTAT CGTTTGGCGC AAACGGCAAT AAAGTTGATA TTACCAGTGA TGCAAATGGC   480
TTGAAATTGG CGAAAACAGG TAACGGAAAT GGTCAAAACA GTAATGTTCA CTTAAACGGT   540
ATTGCTTCGA CTTTGACCGA TACGCTTGCC GGTGGCACAA CAGGACACGT TGACACCAAC   600
ATTGATGCGG TTAATTATCA TCGCGCTGCA AGCGTACAAG ATGTGTTAAA CAGCGGTTGG   660
AATATCCAAG GCAATGGAAA CAATGTCGAT TTTGTCCGTA CTTACGACAC CGTGGACTTT   720
GTCAATGGCG CGAATGCCAA TGTGAGCGTT ACGGCTGATA CGGCTCACAA AAAGACAACT   780
GTCCGTGTGG ATGTAACAGG CTTGCCGGTT CAATATGTTA CGGAAGACGG CAAAACCGTT   840
GTGAAAGTGG GCAATGAGTA TTACAAAGCC AAAGATGACG GTTCGGCGGA TATGAATCAA   900
AAAGTCGAAA ACGGCGAGCT GGCGAAAACC AAAGTGAAAT TGGTATCGGC AAGCGGTACA   960
AATCCGGTGA AAATTAGCAA TGTTGCAGAC GGCACGGAAG ACACCGATGC GGTCAGCTTT  1020
AAGCAATTAA AAGCCTTGCA AGACAAACAG GTTACGTTGA GCACGAGCAA TGCTTATGCC  1080
AATGGCGGTA CAGATAACGA CGGCGGCAAG GCAACTCAAA CTTTAAGCAA TGGTTTGAAT  1140
TTTAAATTTA AATCTAGCGA TGGCGAGTTG TTGAAAATTA GCGCGACCGG CGATACGGTT  1200
ACTTTTACGC CGAAAAAAGG TTCGGTACAG GTTGGCGATG ATGGCAAGGC TTCAATTTCA  1260
AAAGGTGCAA ATACAACTGA AGGTTTGGTT GAGGCTTCTG AATTGGTTGA AAGCCTGAAC  1320
AAACTGGGTT GGAAAGTAGG GGTTGAGAAA GTCGGCAGCG GCGAGCTTGA TGGTACATCC  1380
AAGGAAACTT TAGTGAAGTC GGGCGATAAA GTAACTTTGA AGCCGGCGA CAATCTGAAG  1440
GTCAAACAAG AGGGCACAAA CTTCACTTAC GCGCTCAAAG ATGAATTGAC GGGCGTGAAG  1500
AGCGTGGAGT TTAAAGACAC GGCGAATGGT GCAAACGGTG CAAGCACGAA GATTACCAAA  1560
GACGGCTTGA CCATTACGCT GGCAAACGGT GCGAATGGTG CGACGGTGAC TGATGCCGAC  1620
AAGATTAAAG TTGCTTCGGA CGGCATTAGC GCGGGTAATA AAGCAGTTAA AAACGTCGCG  1680
GCAGGCGAAA TTTCTGCCAC TTCCACCGAT GCGATTAACG GAAGCCAGTT GTATGCCGTG  1740
GCAAAAGGGG TAACAAACCT TGCTGGACAA GTGAATAATC TTGAGGGCAA AGTGAATAAA  1800
GTGGGCAAAC GTGCAGATGC AGGTACTGCA AGTGCATTAG CGGCTTCACA GTTACCACAA  1860
GCCACTATGC CAGGTAAATC AATGGTTTCT ATTGCGGGAA GTAGTTATCA AGGTCAAAAT  1920
GGTTTAGCTA TCGGGGTATC AAGAATTTCC GATAATGGCA AAGTGATTAT TCGCTTGTCT  1980
```

-continued

```
GGCACAACCA ATAGTCAAGG TAAAACAGGC GTTGCAGCAG GTGTTGGTTA CCAGTGG       2037
```

(2) INFORMATION FOR SEQ ID NO: 15:

(i) SEQUENCE CHARACTERISTICS:
        (A) LENGTH: 679 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 15:

```
Met Asn Lys Ile Phe Asn Val Ile Trp Asn Val Val Thr Gln Thr Trp
 1               5                  10                  15

Val Val Val Ser Glu Leu Thr Arg Thr His Thr Lys Cys Ala Ser Ala
            20                  25                  30

Thr Val Ala Val Ala Val Leu Ala Thr Leu Leu Ser Ala Thr Val Gln
        35                  40                  45

Ala Asn Ala Thr Asp Glu Asn Glu Asp Asp Glu Glu Leu Glu Pro
50                  55                  60

Val Gln Arg Ser Val Leu Arg Trp Ser Phe Lys Ser Ala Lys Glu Gly
65                  70                  75                  80

Thr Gly Glu Gln Glu Gly Thr Thr Glu Val Ile Asn Leu Asn Thr Asp
                85                  90                  95

Ser Ser Gly Asn Ala Val Gly Ser Ser Thr Ile Thr Phe Lys Ala Gly
            100                 105                 110

Asp Asn Leu Lys Ile Lys Gln Ser Gly Asn Asp Phe Thr Tyr Ser Leu
        115                 120                 125

Lys Lys Glu Leu Lys Asn Leu Thr Ser Val Glu Thr Glu Lys Leu Ser
    130                 135                 140

Phe Gly Ala Asn Gly Asn Lys Val Asp Ile Thr Ser Asp Ala Asn Gly
145                 150                 155                 160

Leu Lys Leu Ala Lys Thr Gly Asn Gly Asn Gln Asn Ser Asn Val
                165                 170                 175

His Leu Asn Gly Ile Ala Ser Thr Leu Thr Asp Thr Leu Ala Gly Gly
            180                 185                 190

Thr Thr Gly His Val Asp Thr Asn Ile Asp Ala Val Asn Tyr His Arg
        195                 200                 205

Ala Ala Ser Val Gln Asp Val Leu Asn Ser Gly Trp Asn Ile Gln Gly
    210                 215                 220

Asn Gly Asn Asn Val Asp Phe Val Arg Thr Tyr Asp Thr Val Asp Phe
225                 230                 235                 240

Val Asn Gly Ala Asn Ala Asn Val Ser Val Thr Ala Asp Thr Ala His
                245                 250                 255

Lys Lys Thr Thr Val Arg Val Asp Val Thr Gly Leu Pro Val Gln Tyr
            260                 265                 270

Val Thr Glu Asp Gly Lys Thr Val Lys Val Gly Asn Glu Tyr Tyr
        275                 280                 285

Lys Ala Lys Asp Asp Gly Ser Ala Asp Met Asn Gln Lys Val Glu Asn
    290                 295                 300

Gly Glu Leu Ala Lys Thr Lys Val Lys Leu Ser Ala Ser Gly Thr
305                 310                 315                 320

Asn Pro Val Lys Ile Ser Asn Val Ala Asp Gly Thr Glu Asp Thr Asp
                325                 330                 335
```

-continued

```
Ala Val Ser Phe Lys Gln Leu Lys Ala Leu Gln Asp Lys Gln Val Thr
            340                 345                 350

Leu Ser Thr Ser Asn Ala Tyr Ala Asn Gly Gly Thr Asp Asn Asp Gly
            355                 360                 365

Gly Lys Ala Thr Gln Thr Leu Ser Asn Gly Leu Asn Phe Lys Phe Lys
        370                 375                 380

Ser Ser Asp Gly Glu Leu Leu Lys Ile Ser Ala Thr Gly Asp Thr Val
385                 390                 395                 400

Thr Phe Thr Pro Lys Lys Gly Ser Val Gln Val Gly Asp Asp Gly Lys
                405                 410                 415

Ala Ser Ile Ser Lys Gly Ala Asn Thr Thr Glu Gly Leu Val Glu Ala
                420                 425                 430

Ser Glu Leu Val Glu Ser Leu Asn Lys Leu Gly Trp Lys Val Gly Val
            435                 440                 445

Glu Lys Val Gly Ser Gly Glu Leu Asp Gly Thr Ser Lys Glu Thr Leu
450                 455                 460

Val Lys Ser Gly Asp Lys Val Thr Leu Lys Ala Gly Asp Asn Leu Lys
465                 470                 475                 480

Val Lys Gln Glu Gly Thr Asn Phe Thr Tyr Ala Leu Lys Asp Glu Leu
                485                 490                 495

Thr Gly Val Lys Ser Val Glu Phe Lys Asp Thr Ala Asn Gly Ala Asn
            500                 505                 510

Gly Ala Ser Thr Lys Ile Thr Lys Asp Gly Leu Thr Ile Thr Leu Ala
            515                 520                 525

Asn Gly Ala Asn Gly Ala Thr Val Thr Asp Ala Asp Lys Ile Lys Val
        530                 535                 540

Ala Ser Asp Gly Ile Ser Ala Gly Asn Lys Ala Val Lys Asn Val Ala
545                 550                 555                 560

Ala Gly Glu Ile Ser Ala Thr Ser Thr Asp Ala Ile Asn Gly Ser Gln
                565                 570                 575

Leu Tyr Ala Val Ala Lys Gly Val Thr Asn Leu Ala Gly Gln Val Asn
            580                 585                 590

Asn Leu Glu Gly Lys Val Asn Lys Val Gly Lys Arg Ala Asp Ala Gly
        595                 600                 605

Thr Ala Ser Ala Leu Ala Ala Ser Gln Leu Pro Gln Ala Thr Met Pro
610                 615                 620

Gly Lys Ser Met Val Ser Ile Ala Gly Ser Ser Tyr Gln Gly Gln Asn
625                 630                 635                 640

Gly Leu Ala Ile Gly Val Ser Arg Ile Ser Asp Asn Gly Lys Val Ile
                645                 650                 655

Ile Arg Leu Ser Gly Thr Thr Asn Ser Gln Gly Lys Thr Gly Val Ala
            660                 665                 670

Ala Gly Val Gly Tyr Gln Trp
            675
```

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 16:

```
                                    -continued

CCGTGCTTGC CCAACACGCT T                                               21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 17:

GCTGCCACCT TGCACAACAA C                                               21

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 18:

CTTTCAATGC CAGAAAGTAG G                                               21

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 19:

CTTCAACCGT TGCGGACAAC A                                               21
```

HAEMOPHILUS ADHESION PROTEINS

This is a divisional of application U.S. Ser. No. 08/913,942, filed Dec. 29, 1997 now U.S. Pat. No. 6,200,578; which application is a 371 of PCT/US96/0403, filed Mar. 22, 1996, which is a continuation of Ser. No. 08/409,995, filed Mar. 24, 1995, now U.S. Pat. No. 5,646,259 which is incorporated herein by reference and to which applications priority is claimed under 35 USC §§119–120.

The U.S. Government has certain rights in this invention pursuant to grant numbers AI-21707 and HD-29687 from National Institutes of Health.

FIELD OF THE INVENTION

The invention relates to novel Haemophilus adhesion proteins, nucleic acids, and antibodies.

BACKGROUND OF THE INVENTION

Most bacterial diseases begin with colonization of a particular mucosal surface (Beachey et al., 1981, J. Infect. Dis. 143:325–345). Successful colonization requires that an organism overcome mechanical cleansing of the mucosal surface and evade the local immune response. The process of colonization is dependent upon specialized microbial factors that promote binding to host cells (Hultgren et al., 1993 Cell, 73:887–901). In some cases the colonizing organism will subsequently enter (invade) these cells and survive intracellularly (Falkow, 1991, Cell 65:1099–1102).

*Haemophilus influenzae* is a common commensal organism of the human respiratory tract (Kuklinska and Kilian. 1984, Eur. J. Clin. Microbiol. 3:249–252). It is the most common cause of bacterial meningitis and a leading cause of other invasive (bacteraemic) diseases. In addition, this organism is responsible for a sizeable fraction of acute and chronic otitis media, sinusitis, bronchitis, and pneumonia.

*Haemophilus influenzae* is a human-specific organism that normally resides in the human nasopharynx and must colonize this site in order to avoid extinction. This microbe has a number of surface structures capable of promoting attachment to host cells (Guerina et al., 1982, J. Infect. Dis. 146:564; Pichichero et al., 1982, Lancet ii:960–962; St. Geme et al., 1993, Proc. Natl. Acad. Sci. U.S.A. 90:2875–2879). In addition, *H. influenzae* has acquired the capacity to enter and survive within these cells (Forsgren et al., 1994, Infect. Immun. 62:673–679; St. Geme and Falkow, 1990, Infect. Immun. 58:4036–4044; St. Geme and Falkow, 1991, Infect. Immun. 59:1325–1333, Infect. Immun. 59:3366–3371). As a result, this bacterium is an important cause of both localized respiratory tract and systemic disease (Turk, 1984, J. Med. Microbiol. 18:1–16). Nonencapsulated, non-typable strains account for the majority of local disease (Turk, 1984, supra); in contrast, serotype b strains, which express a capsule composed of a polymer of ribose and ribitol-5-phosphate (PRP), are responsible for over 95% of cases of *H. influenzae* systemic disease (Turk, 1982, Clinical importance of *Haemophilus influenzae*, p. 3–9. In S. H. Sell and P. F. Wright (ed.). *Haemophilus influenzae* epidemiology, immunology, and prevention of disease. Elsevier/North-Holland Publishing Co., New York).

The initial step in the pathogenesis of disease due to *H. influenzae* involves colonization of the upper respiratory mucosa (Murphy et al., 1987, J. Infect. Dis. 5:723–731). Colonization with a particular strain may persist for weeks to months and most individuals remain asymptomatic throughout this period (Spinola et al., 1986.1, Infect. Dis. 154:100–109). However, in certain circumstances colonization will be followed by contiguous spread within the respiratory tract, resulting in local disease in the middle ear, the sinuses, the conjunctiva, or the lungs. Alternatively. on occasion bacteria will penetrate the nasopharyngeal epithelial barrier and enter the bloodstream.

In vitro observations and animal studies suggest that bacterial surface appendages called pili (or fimbriae) play an important role in *H. influenzae* colonization. In 1982 two groups reported a correlation between piliation and increased attachment to human oropharyngeal epithelial cells and erythrocytes (Guerina et al., supra: Pichichero et al., supra). Other investigators have demonstrated that anti-pilus antibodies block in vitro attachment by piliated *H. influenzae* (Forney et al., 1992, J. Infect. Dis. 165:464–470; van Alphen et al., 1988, Infect. Immun. 56:1800–1806) Recently Weber et al. insertionally inactivated the pilus structural gene in an *H. influenzae* type b strain and thereby eliminated expression of pili; the resulting mutant exhibited a reduced capacity for colonization of year-old monkeys (Weber et al., 1991, Infect. Immun. 59:4724–4728).

A number of reports suggest that nonpilus factors also facilitate Haemophilus colonization. Using the human nasopharyngeal organ culture model. Farley et al. (1986, J. Infect. Dis. 161:274–280) and Loeb et al. (1988, Infect. Immun. 49:484–489) noted that nonpiliated type b strains were capable of mucosal attachment. Read and coworkers made similar observations upon examining nontypable strains in a model that employs nasal turbinate tissue in organ culture (1991, J. Infect. Dis. 163:549–558). In the monkey colonization study by Weber et al. (1991, supra), nonpiliated organisms retained a capacity for colonization, though at reduced densities: moreover, among monkeys originally infected with the piliated strain, virtually all organisms recovered from the nasopharynx were nonpiliated. All of these observations are consistent with the finding that nasopharyngeal isolates from children colonized with *H. influenzae* are frequently nonpiliated (Mason et al., 1985, Infect. Immun. 49:98–103; Brinton et al., 1989, Pediatr. Infect. Dis. J. 8:554–561)

Previous studies have shown that *H. influenzae* are capable of entering (invading) cultured human epithelial cells via a pili-independent mechanism (St. Geme and Falkow, 1990, supra; St. Geme and Falkow, 1991, supra). Although *H. influenzae* is not generally considered an intracellular parasite, a recent report suggests that these in vitro findings may have an in vivo correlate (Forsgren et al., 1994, supra). Forsgren and coworkers examined adenoids from 10 children who had their adenoids removed because of long-standing secretory otitis media or adenoidal hypertrophy. In all 10 cases there were viable intracellular *H. influenzae*. Electron microscopy demonstrated that these organisms were concentrated in the reticular crypt epithelium and in macrophage-like cells in the subepithelial layer of tissue. One possibility is that bacterial entry into host cells provides a mechanism for evasion of the local immune response, thereby allowing persistence in the respiratory tract Thus, a vaccine for the therapeutic and prophylactic treatment of Haemophilus infection is desirable. Accordingly, it is an object of the present invention to provide for recombinant Haemophilus Adherence (HA) proteins and variants thereof, and to produce useful quantities of these HA proteins using recombinant DNA techniques.

It is a further object of the invention to provide recombinant nucleic acids encoding HA proteins, and expression vectors and host cells containing the nucleic acid encoding the HA protein.

An additional object of the invention is to provide monoclonal antibodies for the diagnosis of Haemophilus infection.

A further object of the invention is to provide methods for producing the HA proteins, and a vaccine comprising the HA proteins of the present invention.

Methods for the therapeutic and prophylactic treatment of Haemophilus infection are also provided.

SUMMARY OF THE INVENTION

In accordance with the foregoing objects, the present invention provides recombinant HA proteins, and isolated or recombinant nucleic acids which encode the HA proteins of the present invention. Also provided are expression vectors which comprise DNA encoding a HA protein operably linked to transcriptional and translational regulatory DNA, and host cells which contain the expression vectors.

The invention provides also provides methods for producing HA proteins which comprises culturing a host cell transformed with an expression vector and causing expression of the nucleic acid encoding the HA protein to produce a recombinant HA protein.

The invention also includes vaccines for *Haemophilus influenzae* infection comprising an HA protein for prophylactic or therapeutic use in generating an immune response in a patient. Methods of treating or preventing *Haemophilus influenzae* infection comprise administering a vaccine.

BRIEF DESCRIPTION OF THE DRAWINGS

FIGS. 1A, 1B, and 1C (SEQ ID NO:1) depict the nucleic acid sequence of HA1.

FIGS. 2A–2D (SEQ ID NO:2) depict the amino acid sequence of HA1.

FIGS. 3A, 3B, 3C, 3D, 3E, 3F and 3G (SEQ ID NOS:3 &4) depict the nucleic acid sequence and amino acid sequence of HA2.

FIG. 4 shows the schematic alignment of HA1 and HA2. Regions of sequence similarity are indicated by shaded, striped, and open bars, corresponding to N-terminal domains, internal domains, and C-terminal domains, respectively. The solid circles represent a conserved Walker box ATP-binding motif (GINVSGKT). Numbers above the bars refer to amino acid residue positions in the full-length proteins. Numbers in parentheses below the HA2 bars represent percent similarity/percent identity between these domains and the corresponding HA1 domains. The regions of HA2 defined by amino acid residues 51 to 173, 609 to 846, and 1292 to 1475 show minimal similarity to amino acids 51 to 220 of HA1.

FIGS. 5A and 5B (SEQ ID NOS:5 & 6) depict the homology between the N-terminal amino acid sequences of HA1 and HA2. Single letter abbreviations are used for the amino acids. A line indicates identity between the residues, and two dots indicate conservative changes, i.e. similarity between residues.

FIG. 6 depicts the restriction maps of phage 11-17 and plasmid pT7-7 subclones.

FIG. 7 depicts the restriction map of pDC400 and derivatives. pDC400 contains a 9.1 kb insert from strain C54 cloned into pUC19. Vector sequences are represented by hatched boxes. Letters above the top horizontal line indicate restriction enzyme sites: Bg, BglII; E, EcoRI; H, HindIII; P, PstI; S, SalI; Ss, SstI; X, XbaI. The heavy horizontal line with arrow represents the location of the hsf locus within pDC400 and the direction of transcription. The striated horizontal line represents the 3.3 kb intragenic fragment used as a probe for Southern analysis. The plasmid pDC602, which is not shown, contains the same insert as pDC601, but in the opposite orientation.

FIG. 8 shows the identification of plasmid-encoded proteins using the bacteriophage T7 expression system. Bacteria were radiolabelled with trans-[$^{35}$S]-label, and whole cell lysates were resolved on a 7.5% SDS-polyacrylamide gel. Proteins were visualized by autoradiography. Lane 1, *E. coli* BL21(DE3)/pT7-7 uninduced; lane 2, BL21(DE3)/pT7-7 induced; lane 3, BL21(DE3)/pDC602 uninduced; lane 4, BL21(DE3)/pDC602 induced; lane 5, BL21(DE3)/pDC601 uninduced; lane 6, BL21(DE3)/pDC601 induced. The plasmids pDC602 and pDC601 are derivatives of pT7-7 that contain the 8.3 kb XbaI fragment from pDC400 in opposite orientations. The asterisk indicates the overexpressed protein in BL21(DE3)/pDC601.

FIGS. 9A and 9B depict the southern analysis of chromosomal DNA from *H. influenzae* strains C54 and 11, probing with HA2 versus HA1. DNA fragments were separated on a 0.7% agarose gel and transferred bidirectionally to nitrocellulose membranes prior to probing with either HA1 or HA2. Lane 1, C54 chromosomal DNA digested with BglII; lane 2, C54 chromosomal DNA digested with ClaI; lane 3, C54 chromosomal DNA digested with PstI; lane 4, 11 chromosomal DNA digested with BglII; lane 5, 11 chromosomal DNA digested with ClaI; lane 6, 11 chromosomal DNA digested with XbaI. A. Hybridization with the 3.3 kb PstI-BglII intragenic fragment of HA2 from strain C54. B. Hybridization with the 1.6 kb StyI-SspI intragenic fragment of HA1 from strain 11.

FIG. 10 depicts the comparison of cellular binding specificities of *E. coli* DH5α harboring HA2 versus HA1. Adherence was measured after incubating bacteria with eucaryotic cell monolayers for 30 minutes as described and was calculated by dividing the number of adherent colony forming units by the number of inoculated colony forming units (St. Geme et al., 1993). Values are the mean±SEM of measurements made in triplicate from representative experiments. The plasmid pDC601 contains the HA2 gene from *H. influenzae* strain C54, while pHMW8-5 contains the HA1 gene from nontypable *H. influenzae* strain 11. Both pDC601 and pHMW8-5 were prepared using pT7-7 as the cloning vector.

FIG. 11 depicts the comparison of the N-terminal extremities of HA2 (SEQ ID NO:7), HMW1 (SEQ ID NO:9), HMW2 (SEQ ID NO:10), AIDA-I (SEQ ID NO:11), Tsh (SEQ ID NO:12), and SepA (SEQ ID NO:13). The N-terminal sequence of HA2 (SEQ ID NO:7) is aligned with those of HA1 (SEQ ID NO:8) (Barenkamp, S. J., and J. W. St. Geme, III. Identification of a second family of high molecular weight adhesion proteins expressed by nontypable *Haemophilus influenzae*. Mol. Microbiol., in press.), HMW1 (SEQ ID NO:9) and HMW2 (SEQ ID NO:10) (Barenkamp, S. J., and E. Leininger. 1992. Cloning, expression, and DNA sequence analysis of genes encoding nontypeable *Haemophilus influenzae* high molecular weight surface-exposed proteins related to filamentous hemagglutinin of *Bordetella pertussis*. Infect. Immun. 60:1302–1313.), AIDA-I (SEQ ID NO:11) (Benz, I., and M. A. Schmidt. 1992. AIDA-I, the adhesin involved in diffuse adherence of the diarrhoeagenic *Escherichia coli* strain 2787 (O126:H27), is synthesized via a precursor molecule. Mol. Microbiol. 6:1539–1546.), Tsh (SEQ ID NO:12) (Provence, D. and R. Curtiss III 1994. Isolation and characterization of a gene involved in hemagglutination by an avian pathogenic *Escherichia coli* strain. Infect. Immun. 62:1369–1380.), and Sep A (SEQ ID NO:13) (Benjelloun-Touimi, Z., P. J. Sansonetti, and C. Parsot. 1995. SepA, the major extracellular protein of*Shigella flexneri*: autonomous secretion and involvement in tissue invasion. Mol. Microbiol. 17:123–135.). A consensus sequence is shown on the lower line.

FIG. 12 depicts the southern analysis of chromosomal DNA from epidemiologically distinct strains of *H. influenzae* type b. Chromosomal DNA was digested with BglII, separated on a 0.7% agarose gel, transferred to nitrocellulose, and probed with the 3.3 kb PstI-BglII intragenic fragment of hsf from strain C54. Lane 1, strain C54; lane 2, strain 1081; lane 3, strain 1065; lane 4, strain 1058; lane 5, strain 1060; lane 6, strain 1053; lane 7, strain 1063; lane 8, strain 1069; lane 9, strain 1070; lane 10, strain 1076; lane 11, strain 1084.

FIG. 13 depicts the southern analysis of chromosomal DNA from non-type b encapsulated strains of *H. influenzae*. Chromosomal DNA was digested with BglII, separated on a 0.7% agarose gel, transferred to nitrocellulose, and probed with the 3.3 kb PstI-BgtII intragenic fragment of hsf from strain C54. Lane 1, SM4 (type a); lane 2, SM72 (type c); lane 3, SM6 (type d); lane 4, Rd (type d); lane 5, SM7 (type e); lane 6, 142 (type e); lane 7, 327 (type e); lane 8, 351 (type e); lane 9, 134 (type f); lane 10, 219 (type f); lane 11, 346 (type f); lane 12, 503 (type f).

FIGS. 14A and 14B (SEQ ID NO:14) are the nucleic acid sequence of HA3.

FIG. 15 (SEQ ID NO:15) is the amino acid sequence of HA3.

FIGS. 16A and 16B (SEQ ID NOS:2 & 15) depict the homology between the amino acid sequences of HA1 and HA3. Single letter abbreviations are used for the amino acids. A line indicates identity between the residues, and two dots indicate conservative changes, i.e. similarity between residues.

DETAILED DESCRIPTION OF THE INVENTION

The present invention provides novel Haemophilus Adhesion (HA) proteins. In a preferred embodiment, the HA proteins are from Haemophilus strains, and in the preferred embodiment, from *Haemophilus influenza*. In particular. *H. influenzae* encapsulated type b strains are used to clone the HA proteins of the invention. However, using the techniques outlined below, HA proteins from other *Haemophilus influenzae* strains, or from other bacterial species such as Neisseria spp. or Bordetalla spp. may also be obtained.

Three HA proteins, HA1, HA2 and HA3, are depicted in FIGS. 2, 3 and 15 (SEQ ID NOS:2, 3–4, & 15), respectively. HA2 is associated with the formation of surface fibrils, which are involved in adhesion to various host cells. HA1 has also been implicated in adhesion to a similar set of host cells. When the HA1 or HA2 nucleic acid is expressed in a non-adherent strain of *E. coli* as described below, the *E. coli* acquire the ability to adhere to human host cells. It should be noted that in the literature, HA1 is referred to as hia (*H. influenza* adherence) and HA2 is referred to as hsf (Haemophilus surface fibrils).

A HA protein may be identified in several ways. A HA nucleic acid or HA protein is initially identified by substantial nucleic acid and/or amino acid sequence homology to the sequences shown in FIGS. 1, 2, 3, 14 or 15 (SEQ ID NOS:1, 2, 3–4, 14 or 15). Such homology can be based upon the overall nucleic acid or amino acid sequence or portions thereof.

As used herein, a protein is a "HA protein" if the overall homology of the protein sequence to the amino acid sequence shown in FIGS. 2 (SEQ ID NO:2) and/or FIG. 3 (SEQ ID NO:4) and/or FIG. 15 (SEQ ID NO:15) is preferably greater than about 45 to 50%, more preferably greater than about 65% and most preferably greater than 80%. In some embodiments the homology will be as high as about 90 to 95 or 98%. That is, a protein that has at least 50% homology (or greater) to one, two or all three of the amino acid sequences of HA1, HA2 and HA3 is considered a HA protein. This homology will be determined using standard techniques known in the art, such as the Best Fit sequence program described by Devereux et al., *Nucl. Acid Res.* 12:387–395 (1984) or the BLASTX program (Altschul et al., *J. Mol. Biol.* 215:403–410 (1990)). The alignment may include the introduction of gaps in the sequences to be aligned. As noted below, in the comparison of proteins of different lengths, such as HA1 and HA3 with HA2, the homology is determined on the basis of the length of the shorter sequence.

In a preferred embodiment, a HA protein is defined as having significant homology to either the N-terminal region or the C-terminal region, or both, of the HA1, HA2 and HA3 proteins depicted in FIGS. 4, 5 and 15. The N-terminal region of about 50 amino acids is virtually identical as between HA1 and HA3 (98% homology), and as between either HA1 or HA3 and HA2 is 74%. As shown in FIG. 11, the first 24 amino acids of the N-terminus of HA1 and HA2 has limited homology to several other proteins, but this homology is 50% or less. Thus, a HA protein may be defined as having homology to the N-terminal region of at least about 60%, preferably at least about 70%, and most preferably at least about 80%, with homology as high as 90 or 95% especially preferred. Similarly, the C-terminal region of at least about 75, preferably 100 and most preferably 125 amino acid residues is also highly homologous and can be used to identify a HA protein. As shown in FIG. 16, the homology between the C-terminal 120 or so amino acids of HA1 and HA3 is about 98%, and as between either HA1 or HA3 and HA2 is also about 98%. Thus homology at the C-terminus is a particularly useful way of identifying a HA protein. Accordingly, a HA protein can be defined as having homology to the C-terminal region of at least about 60%, preferably at least about 70%, and most preferably at least about 80%, with homology as high as 90 or 95% especially preferred. In a preferred embodiment, the HA protein has homology to both the N- and C-terminal regions.

In addition, a HA protein may be identified as containing at least one stretch of amino acid homology found at least in the HA1 and HA2 proteins as depicted in FIG. 4. HA2 contains three separate stretchs of amino acids (174 to 608, 847 to 1291, and 1476 to 1914, respectively) that shows significant homology to the region of HA1 defined by amino acids 221 to 658.

The HA proteins of the present invention have limited homology to the high molecular weight protein-1 (HMW1) of *H. influenzae*, as well as the AIDA-1 adhesin of *E. coli*. For the HMW1 protein, this homology is greatest between residues 60-540 of the HA1 protein and residues 1100 to about 1550 of HMW1, with 20% homology in this overlap region. For the AIDA-I protein, there is a roughly 50% homology between the first 30 amino acids of AIDA-I and HA1, and the overall homology between the proteins is roughly 22%.

In addition, the HA1, HA2 and HA3 proteins of the present invention have homology to each other, as shown in FIGS. 4, 5 and 16. As between HA1 and HA2, the homology is 81% similarity and 72% identity overall. HA3 and HA1 are 51% identical and 65% similar. Thus, for the purposes of the invention, HA1, HA2 and HA3 are all HA proteins.

An "HA1" protein is defined by substantial homology to the sequence shown in FIG. 2 (SEQ ID NO:2). This homology is preferably greater than about 60%, more preferably greater than about 70% and most preferably greater than 80%. In preferred embodiments the homology will be as high as about 90 to 95 or 98%. Similarly, an "HA2" protein may be defined by the same substantial homology to the sequence shown in FIG. 3 (SEQ ID NO:4), and a "HA3" protein is defined with reference to FIG. 15 (SEQ ID NO:15), as defined above.

In addition, for sequences which contain either more or fewer amino acids than the proteins shown in FIGS. 2, 3 and 15 (SEQ ID NOS:2, 4 & 15), it is understood that the percentage of homology will be determined based on the number of homologous amino acids in relation to the total number of amino acids. Thus, for example, homology of sequences shorter than that shown in FIGS. 2, 3 and 15 (SEQ ID NOS:2, 4 & 15), as discussed below, will be determined using the number of amino acids in the shorter sequence.

HA proteins of the present invention may be shorter than the amino acid sequences shown in FIGS. 2, 3 and 15 (SEQ ID NOS:2, 4 & 15). Thus, in a preferred embodiment, included within the definition of HA proteins are portions or fragments of the sequence shown in FIGS. 2, 3 and 15 (SEQ ID NOS:2, 4 & 15). Generally, the HA protein fragments may range in size from about 7 amino acids to about 800 amino acids, with from about 15 to about 700 amino acids being preferred, and from about 100 to about 650 amino acids also preferred. Particularly preferred fragments are sequences unique to HA; these sequences have particular use in cloning HA proteins from other organisms, to generate antibodies specific to HA proteins, or for particular use as a vaccine. Unique sequences are easily identified by those skilled in the art after examination of the HA protein sequence and comparison to other proteins; for example, by examination of the sequence alignment shown in FIGS. 5 (SEQ ID NOS:5 & 6) and 16 (SEQ ID NOS:2 & 15). Preferred unique sequences include the N-terminal region of the HA1, HA2 and HA3 sequences, comprising roughly 50 amino acids and the C-terminal 120 amino acids, depicted in FIGS. 2, 3 and 15 (SEQ ID NOS:2, 4 & 15). HA protein fragments which are included within the definition of a HA protein include N- or C-terminal truncations and deletions which still allow the protein to be biologically active; for example, which still allow adherence, as described below. In addition, when the HA protein is to be used to generate antibodies, for example as a vaccine, the HA protein must share at least one epitope or determinant with the sequences shown in FIGS. 2, 3 and 15 (SEQ ID NOS:2, 4 & 15). In a preferred embodiment, the epitope is unique to the HA protein; that is, antibodies generated to a unique epitope exhibit little or no cross-reactivity with other proteins. However, cross reactivity with other proteins does not preclude such epitopes or antibodies for immunogenic or diagnostic uses. By "epitope" or "determinant" herein is meant a portion of a protein which will generate and/or bind an antibody. Thus, in most instances, antibodies made to a smaller HA protein will be able to bind to the full length protein.

In some embodiments, the fragment of the HA protein used to generate antibodies are small; thus, they may be used as haptens and coupled to protein carriers to generate antibodies, as is known in the art.

In addition, sequences longer than those shown in FIGS. 2, 3 and 15 are also included within the definition of HA proteins.

Preferably, the antibodies are generated to a portion of the HA protein which is exposed at the outer membrane, i.e. surface exposed. The amino-terminal portions of HA1, HA2 and HA3 are believed to be externally exposed proteins.

The HA proteins may also be identified as associated with bacterial adhesion. Thus, deletions of the HA proteins from the naturally occuring microorganism such as Haemophilus species results in a decrease or absence of binding ability. In some embodiments, the expression of the HA proteins in a non-adherent bacteria such as E. coli results in the ability of the organism to bind to cells.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIGS. 1, 3 and 14 (SEQ ID NOS:1, 3 & 14) is preferably greater than about 40%, more preferably greater than about 60% and most preferably greater than 80%. In some embodiments the homology will be as high as about 90 to 95 or 98%.

As outlined for the protein sequences, a preferred embodiment utilizes HA nucleic acids with substantial homology to the unique N-terminal and C-terminal regions of the HA1, HA2 and HA3 sequences.

In one embodiment, the nucleic acid homology is determined through hybridization studies. Thus, for example, nucleic acids which hybridize under high stringency to all or part of the nucleic acid sequences shown in FIGS. 1, 3 and 14 (SEQ ID NOS:1, 3 & 14) are considered HA protein genes. High stringency conditions include, but are not limited to, washes with 0.1×SSC at 65° C. for 2 hours.

The HA proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequences shown in FIGS. 1, 3 and 14, but may contain ribonucleotides as well as deoxyribonucleotides. Generally, anti-sense nucleic acids function to prevent expression of mRNA, such that a HA protein is not made, or made at reduced levels. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated HA protein gene, in a linear form, or an expression vector formed in vitro by ligating DNA molecules that are not normally joined, are both considered recombinant for the purposes of this invention; i.e. the HA nucleic acid is joined to other than the naturally occurring Haemophilus chromosome in which it is normally found. It is understood that once a recombinant nucleic acid is made and reintroduced into a host cell or organism, it will replicate non-recombinantly, i.e. using the in vivo cellular machinery of the host cell rather than in vitro manipulations: however, such nucleic acids, once produced recombinantly, although subsequently replicated non-recombinantly, are still considered recombinant for the purposes of the invention.

Similarly, a "recombinantprotein" is a protein made using recombinant techniques i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host, or found in the absence of the host cells themselves. Thus, the protein may be partially or substantially purified. The definition includes the production of a HA protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions. Furthermore, although not normally considered "recombinant" proteins or portions of proteins which are synthesized chemically, using the sequence information of FIGS. 2, 3 and 15, are considered recombinant herein as well.

Also included with the definition of HA protein are HA proteins from other organisms, which are cloned and expressed as outlined below.

In the case of anti-sense nucleic acids, an anti-sense nucleic acid is defined as one which will hybridize to all or part of the corresponding non-coding sequence of the sequences shown in FIGS. 1, 3 and 14. Generally, the hybridization conditions used for the determination of anti-sense hybridization will be high stringency conditions, such as 0.1×SSC at 65° C.

Once the HA protein nucleic acid is identified, it can be cloned and, if necessary, its constituent parts recombined to form the entire HA protein nucleic acid. Once isolated from its natural source, e.g., contained within a plasmid or other vector or excised therefrom as a linear nucleic acid segment, the recombinant HA protein nucleic acid can be further used as a probe to identify and isolate other HA protein nucleic acids. It can also be used as a "precursor" nucleic acid to make modified or variant HA protein nucleic acids and proteins.

Using the nucleic acids of the present invention which encode HA protein a variety of expression vectors are made. The expression vectors may be either self-replicating extra-chromosomal vectors or vectors which integrate into a host genome. Generally, these expression vectors include transcriptional and translational regulatory nucleic acid operably linked to the nucleic acid encoding the HA protein. "Operably linked" in this context means that the transcriptional and translational regulatory DNA is positioned relative to the coding sequence of the HA protein in such a manner that transcription is initiated. Generally, this will mean that the promoter and transcriptional initiation or start sequences are positioned 5' to the HA protein coding region. The transcriptional and translational regulatory nucleic acid will generally be appropriate to the host cell used to express the HA protein; for example, transcriptional and translational regulatory nucleic acid sequences from Bacillus will be used to express the HA protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The HA proteins of the present invention are produced by culturing a host cell transformed with an expression vector containing nucleic acid encoding a HA protein, under the appropriate conditions to induce or cause expression of the HA protein. The conditions appropriate for HA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, immortalized mammalian myeloid and lymphoid cell lines.

In a preferred embodiment, HA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of HA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful: for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno(SD) sequence and includes an initiation codon and a sequence 3–9 nucleotides in length located 3–11 nucleotides upstream of the initiation codon.

The expression vector may also include a signal peptide sequence that provides for secretion of the HA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans*, among others.

The bacterial expression vectors are transformed into bacterial host cells using techniques well known in the art, such as calcium chloride treatment, electroporation, and others.

In one embodiment, HA proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the HA protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for HA protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenyltion signals include those derived form SV40.

The methods of introducing exogenous nucleic acid into mammalian hosts, as well as other hosts, is well known in the art, and will vary with the host cell used.

Techniques include dextran-mediated transfection, calcium phosphate precipitation polybrene mediated transfection, protoplast fusion, electroporation, encapsulation of the polynucleotide(s) in liposomes, and direct microinjection of the DNA into nuclei.

In a preferred embodiment, HA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. Preferred promoter sequences for expression in yeast include the inducible GAL1.10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP 1, and ALG7, which confers resistance to tunicamycin; the G418 resistance gene, which confers resistance to G418, and the CUP1 gene, which allows yeast to grow in the presence of copper ions.

A recombinant HA protein may be expressed intracellularly or secreted. The HA protein may also be made as a fusion protein, using techniques well known in the art. Thus, for example, if the desired epitope is small, the HA protein may be fused to a carrier protein to form an immunogen. Alternatively, the HA protein may be made as a fusion protein to increase expression.

Also included within the definition of HA proteins of the present invention are amino acid sequence variants. These variants fall into one or more of three classes: substitutional, insertional or deletional variants. These variants ordinarily are prepared by site specific mutagenesis of nucleotides in the DNA encoding the HA protein, using cassette mutagenesis or other techniques well known in the art, to produce DNA encoding the variant, and thereafter expressing the DNA in recombinant cell culture as outlined above. However, variant HA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the HA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed HA protein variants screened for the optimal combination of desired activity. Techniques for making substitution mutations at predetermined sites in DNA having a known sequence are well known, for example, M13 primer mutagenesis. Screening of the mutants is done using assays of HA protein activities: for example, mutated HA genes are placed in HA deletion strains and tested for HA activity, as disclosed herein. The creation of deletion strains, given a gene sequence, is known in the art. For example, nucleic acid encoding the variants may be expressed in an adhesion deficient strain, and the adhesion and infectivity of the variant *Haemophilus influenzae* evaluated. For example, as outlined below, the variants may be expressed in the *E. coli* DH5a non-adherent strain, and the transformed *E. coli* strain evaluated for adherence using Chang conjunctival cells.

Amino acid substitutions are typically of single residues: insertions usually will be on the order of from about 1 to 20 amino acids, although considerably larger insertions may be tolerated. Deletions range from about 1 to 30 residues, although in some cases deletions may be much larger, as for example when one of the domains of the HA protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the HA protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl: (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the HA protein is altered. For example, the Walker box ATP-binding motif may be altered or eliminated.

In a preferred embodiment, the HA protein is purified or isolated after expression. HA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the HA protein may be purified using a standard anti-HA antibody column.

Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the HA protein. In some instances no purification will be necessary.

Once expressed and purified if necessary, the HA proteins are useful in a number of applications.

For example, the HA proteins can be coupled, using standard technology, to affinity chromatography columns. These columns may then be used to purify antibodies from samples obtained from animals or patients exposed to the *Haemophilus influenzae* organism. The purified antibodies may then be used as outlined below.

Additionally, the HA proteins are useful to make antibodies to HA proteins. These antibodies find use in a number of applications. The antibodies are used to diagnose the presence of an *Haemophilus influenzae* infection in a sample or patient. In a preferred embodiment, the antibodies are used to detect the presence of nontypable *Haemophilus influenza* (NTHI), although typable *H. influenzae* infections are also detected using the antibodies.

This diagnosis will be done using techniques well known in the art: for example, samples such as blood or tissue samples may be obtained from a patient and tested for reactivity with the antibodies, for example using standard techniques such as ELISA. In a preferred embodiment, monoclonal antibodies are generated to the HA protein, using techniques well known in the art. As outlined above, the antibodies may be generated to the full length HA protein, or a portion of the HA protein.

Antibodies generated to HA proteins may also be used in passive immunization treatments, as is known in the art.

Antibodies generated to unique sequences of HA proteins may also be used to screen expression libraries from other organisms to find, and subsequently clone, HA nucleic acids from other organisms.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the HA protein antibody may be labelled for detection, or a secondary antibody to the HA protein antibody may be created and labelled. In one embodiment, the antibodies generated to the HA proteins of the present invention are used to purify or separate HA proteins or the *Haemophilus influenzae* organism from a sample. Thus for example, antibodies generated to HA proteins which will bind to the *Haemophilus influenzae* organism may be coupled, using standard technology, to affinity chromatography columns. These columns can be used to pull out the Haemophilus organism from environmental or tissue samples.

In a preferred embodiment, the HA proteins of the present invention are used as vaccines for the prophylactic or therapeutic treatment of a *Haemophilus influenzae* infection in a patient. By "vaccine" or "immunogenic compositions" herein is meant an antigen or compound which elicits an immune response in an animal or patient The vaccine may be administered prophylactically, for example to a patient never previously exposed to the antigen, such that subsequent infection by the *Haemophilus influenzae* organism is prevented. Alternatively, the vaccine may be administered therapeutically to a patient previously exposed or infected by the *Haemophilus influenzae* organism. While infection cannot be prevented, in this case an immune response is generated which allows the patient's immune system to more effectively combat the infection. Thus, for example, there may be a decrease or lessening of the symptoms associated with infection.

A "patient" for the purposes of the present invention includes both humans and other animals and organisms. Thus the methods are applicable to both human therapy and veterinary applications.

The administration of the HA protein as a vaccine is done in a variety of ways. Generally, the HA proteins can be formulated according to known methods to prepare pharmaceutically useful compositions, whereby therapeutically effective amounts of the HA protein are combined in admixture with a pharmaceutically acceptable carrier vehicle. Suitable vehicles and their formulation are well known in the art. Such compositions will contain an effective amount of the HA protein together with a suitable amount of vehicle in order to prepare pharmaceutically acceptable compositions for effective administration to the host. The composition may include salts, buffers, carrier proteins such as serum albumin, targeting molecules to localize the HA protein at the appropriate site or tissue within the organism, and other molecules. The composition may include adjuvants as well.

In one embodiment, the vaccine is administered as a single dose; that is, one dose is adequate to induce a sufficient immune response to prophylactically or therapeutically treat a *Haemophilus influenzae* infection. In alternate embodiments the vaccine is administered as several doses over a period of time, as a primary vaccination and "booster" vaccinations.

By "therapeutically effective amounts" herein is meant an amount of the HA protein which is sufficient to induce an immune response. This amount may be different depending on whether prophylactic or therapeutic treatment is desired. Generally, this ranges from about 0.001 mg to about 1 gm, with a preferred range of about 0.05 to about 0.5 gm. These amounts may be adjusted if adjuvants are used.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are specifically incorporated by reference.

EXAMPLE 1

Cloning of HA1

Many protocols are substantially the same as those outlined in St. Geme et al., Mol. Microbio, 15(1):77–85 (1995).

Bacterial strains, plasmids, and phages.

Nontypable *H. influenzae* strain II was the clinical isolate chosen as a prototypic HMW1/HMW2-non-expressing strain, although a variety of encapsulated typable strains can be used to clone the protein using the sequences of the figures. The organism was isolated in pure culture from the middle ear fluid of a child with acute otitis media. The strain was identified as *H. influenzae* by standard methods and was classified as nontypable by its failure to agglutinate with a panel of typing antisera for *H. influenzae* types a to f (Burroughs Wellcome Co., Research Triangle Park. N.C.) and failure to show lines of precipitation with these antisera in counterimmunoelectrophoresis assays. Strain 11 adheres efficiently to Chang conjunctival cells in vitro, at levels comparable to those previously demonstrated for NTHI strains expressing HMW1/HMW2-like proteins (data not shown). Convalescent serum from the child infected with this strain demonstrated an antibody response directed predominantly against surface-exposed high molecular weight proteins with molecular weights greater than 100 kDa.

M13mp18 and M13mp19 were obtained from New England BioLabs, Inc. (Beverly, Mass.) pT7-7 was the kind gift of Stanley Tabor. This vector contains the T7 RNA polymerase promoter ϕ10, a ribosome-binding site, and the translational start site for the T7 gene 10 protein upstream from a multiple cloning site.

Molecular cloning and plasmid subcloning.

The recombinant phage containing the HA1 gene was isolated and characterized using methods similar to those described previously. In brief, chromosomal DNA from strain 11 was prepared and Sau3A partial restriction digests of the DNA were prepared and fractionated on 0.7% agarose gels. Fractions containing DNA fragments in the 9- to 20-kbp range were pooled, and a library was prepared by ligation into λEMBL3 arms. Ligation mixtures were packaged in vitro with Gigapack (Stratagene) and plate-amplified in a P2 lysogen of *E. coli* LE392. Lambda plaque immunological screening was performed as described by Maniatis et al., Molecular Cloning: A Laboratory Manual, 2d Ed. (1989). Cold Spring Harbor Press. For plasmid subcloning studies. DNA from recombinant phage was subcloned into the T7 expression plasmid pT7-7. Standard methods were used for manipulation of cloned DNA as described by Maniatis et al (supra).

Plasmid pHMW8-3 was generated by isolating an 11 kbp Xbal fragment from purified DNA from recombinant phage clone 11-17 and ligating into Xbal cut pT7-7. Plasmid pHMW8-4 was generated by isolating a 10 kbp BamHI-Cial cut pT7-7.

Plasmid pHMW8-5 was generated by digesting plasmid pHMW8-3 DNA with Clal, isolating the larger fragment and religating. Plasmid pHMW8-6 was generated by digesting pHMW8-4 with Spel, which cuts at a unique site within the HA1 gene, blunt-ending the resulting fragment, inserting a kanamycin resistance cassette into the Spel site. Plasmid pHMW8-7 was generated by digesting pHMW8-3 with Nrul and HindIII, isolating the fragment containing pT7-7, blunt-ending and religating: The plasmid restriction maps are shown in FIG. 6.

DNA sequence analysis.

DNA sequence analysis was performed by the dideoxy method with the U.S. Biochemicals Sequenase kit as suggested by the manufacturer. [$^{36}$S]dATP was purchased from New England Nuclear (Boston, Mass.). Data were analyzed with Compugene software and the Genetics Computer Group program from the University of Wisconsin on a Digital VAX 8530 computer. Several 21-mer oligonucleotide primers were generated as necessary to complete the sequence.

Adherence assays.

Adherence assays were done with Chang epithelial cells [Wong-Kilboume derivative, clone 1-5c-4 (human conjunctiva), ATCC CCL20.2)], which were seeded into wells of 24-well tissue culture plates, as described (St. Geme III et al., Infect. Immun. 58:4036(1990)). Bacteria were inoculated into broth and allowed to grow to a density of approximately $2\times10^9$ colony-forming units per ml. Approximately $2\times10^7$ colony-forming units were inoculated onto epithelial cells monolayers, and plates were gently centrifuged at 165×g for 5 min to facilitate contact between bacteria and the epithelial surface. After incubation for 30 min at 37° C. in 5% $CO_2$, monolayers were rinsed five times with phosphate buffered saline (PBS) to remove nonadherent organisms and were treated with trypsin-EDTA (0.05% trypsin/0.5% EDTA) in PBS to release them from the plastic support. Well contents were agitated, and dilution were plated on solid medium to yield the number of adherent bacteria per monolayer. Percent adherence was calculated by dividing the number of adherent colony-forming units per monolayer by the number of inoculated colony-forming units.

Isolation and characterization of recombinant phage expressing the strain 11 high molecular weight adhesion protein.

The nontypable *Haemophilus influenzae* strain 11 chromosomal DNA library was screened immunologically with convalescent serum from the child infected with strain 11. Immunoreactive clones were screened by Western blot for expression of high molecular weight proteins with apparent molecular weights >100 dDa and two different classes of recombinant clones were recovered. A single clone designated 11-17 was recovered which expressed the HA1 protein. The recombinant protein expressed by this clone had an apparent molecular weight of greater than 200 kDa.

Transformation into *E. coli*

Plasmids were introduced into DH5α strain of *E. coli* (Maniatis, supra), which is a non-adherent strain, using electroporation (Dower et al., Nucl. Acids Res. 16:6127 (1988). The results are shown in Table 1.

TABLE 1

| Strain | % Adherence* |
| --- | --- |
| DH5α(pHMW 8-4) | 43.3 ± 5.0% |
| DH5α(pHMW 8-5) | 41.3 ± 3.3% |
| DH5α(pHMW 8-6) | 0.6 ± 0.3% |
| DH5α(pHMW 8-7) | |
| DH5α(pT7-7) | 0.4 ± 0.1% |

*Adherence was measured in a 30 minute assay and was calculated by dividing the number of adherent bacteria by the number of inoculated bacteria. Values are the mean ± SEM of measurements made in triplicate from a representative experiment.

In addition, a monoclonal antibody made by standard procedures, directed against the strain 11 protein recognized proteins in 57 of 60 epidemiologically-unrelated NTHI. However, Southern analysis using the gene indicated that roughly only 25% of the tested strains actually hybridized to the gene (data not shown).

EXAMPLE 2

Cloning of HA2

In a recent study we examined a series of *H. influenza* type b isolates by transmission electron microscopy and visualized short, thin surface fibrils distinct from pili (St. Geme. J. W. III. and D. Cutter. 1995. Evidence that surface fibrils expressed by *Haemophilus influenzae* type b promote attachment to human epithelial cells. Mol. Microbiol. 15:77–85.). In that study, the large genetic locus involved in the expression of these appendages was isolated.

Bacterial strains and plasmids

*H. influenzae* strain C54 is a type b strain that has been described previously (Pichichero, M. E., P. Anderson, M. Loeb, and D. H. Smith. 1982. Do pili play a role in pathogenicity of *Haemophilus influenzae* type b? Lancet. ii:960–962.). Strain C54-Tn400.23 is a mutant that contains a mini-Tn10 kan element in the hsf locus and demonstrates minimal in vitro adherence (St. Geme, J. W. III, and D. Cutter. 1995. Evidence that surface fibrils expressed by *Haemophilus influenzae* type b promote attachment to human epithelial cells. Mol. Microbiol. 15:77–85.). Strains 1053, 1058, 1060, 1063, 1065, 1069, 1070, 1076, 1081, and 1084 are *H. influenzae* type b isolates generously provided by J. Musser (Baylor University, Houston, Tex.) (Musser et al., 1990. Global genetic structure and molecular epidemiology of encapsulated *Haemophilus influenzae*, Rev. Infect. Dis. 12:75–111.). *H. influenzae* strains SM4 (type a), SM6 (type d), SM7 (type e), and SM72 (type c) are type strains obtained from R. Facklam at the Centers for Disease Control (Atlanta, Ga.). Strains 142, 327, and 351 are *H. influenzae* type e isolates, and strains 134, 219, 256, and 501 are *H. influenzae* type f isolates obtained from H. Kayhty (Finnish National Public Health Institute, Helsinki). Strain Rd (typed) and the 15 nontypable isolates examined by Southern analysis have been described previously (Alexander et al., J. Exp. Med. 83:345–359(1951): Barencamp et al., Infect. Immun. 60:1302–1313 (1992)). *E. coli* DH5α is a nonadherent laboratory strain that was originally obtained from Gibco BRL. *E. coli* strain BL21 (DE3) was a gift from F. W. Studier and contains a single copy of the T7 RNA polymerase gene under the control of the lac regulatory system (Studier, F. W., and B. A. Moffatt. 1986. Use of bacteriophage T7 RNA polymerase to direct high-level expression of cloned genes. J. Mol. Biol. 189:113–130.). Plasmid pT7-7 was provided by S. Tabor and contains the T7 RNA polymerase promoter f10, a ribosome-bindingsite, and the translational start site for the T7 gene 10 protein upstream from a multiple cloning site (Tabor, S., and C. C. Richardson. 1985. A bacteriophage T7 RNA polymerase/promoter system for controlled exclusive expression of specific genes. Proc. Natl. Acad. Sci. USA. 82:1074–1078.). pUC 19 is a high-copy-number plasmid that has been previously described (Yanish-Perronet al., Gene 33:103–119(1985)), pDC400 is a pUC19 derivative that harbors the *H. influenzae* strain C54 surface fibril locus and is sufficient to promote in vitro adherence by laboratory strains of *E. coli* (St. Geme, J. W. III, and D. Cutter. 1995. Evidence that surface fibrils expressed by *Haemophilus influenzae* type b promote attachment to human epithelial cells. Mol. Microbiol. 15:77–85.). pHMW8-5 is a pT7-7 derivative that contains the *H. influenzae* strain 11 hia locus and also promotes adherence by nonadherent laboratory, strains of *E. coli* (Barenkamp. S. J., and J. W. St. Geme, III. Identification of a second family of high molecular weight adhesion proteins expressed by nontypable *Haemophilus influenzae*, Mol. Microbiol., in press.). pHMW8-6 contains the *H. influenzae* hia locus interrupted by a kanamycin cassette (Barenkamp. S. J., and J. W. St. Geme, III. Identification of a second family of high molecular weight adhesion proteins expressed by nontypable *Haemophilus influenzae*, Mol. Microbiol., in press.). pUC4K served as the source of the kanamycin-resistancegene that was used as a probe in Southern analysis (Vieira, J., and J. Messing. 1982. The pUC plasmids, an M13mp7-derived system for insertion mutagenesis and sequencing with synthetic universal primers. Gene. 19:259–268.).

Culture conditions

*H. influenzae* strains were grown on chocolate agar supplemented with 1% Isovitale X, on brain heart infusion agar supplemented with hemin and NAD (BHI-DB agar), or in brain heart infusion broth supplemented with hemin and NAD (BHIs) (Anderson, P., R. B. Johnston, Jr., and D. H. Smith. 1972. Human serum activity against *Haemophilus influenzae* type b. J. Clin. Invest. 51:31–38.). These strains were stored at −80° C. in brain heart infusion broth with 25% glycerol. *E. coli* strains were grown on Luria Bertani (LB) agar or in LB broth and were stored at −80° C. in LB broth with 50% glycerol. For *H. influenzae*, kanamycin was used in a concentration of 25 mg/ml. Antibiotic concentrations for *E. coli* included the following: ampicillin or carbenicillin 100 mg/ml and kanamycin 50 mg/ml.

Induction of plasmid-encoded proteins

To identify plasmid-encoded proteins, the bacteriophage T7 expression vector pT7-7was employed and the relevant pT7-7 derivatives were transformed into *E. coli* BL21 (DE3). Activation of the T7 promoter was achieved by inducing expression of T7 RNA polymerase with isopropyl-b-D-thiogalactopyranoside (final concentration, 1 mM). After induction for 30 minutes at 37° C. rifampicin was added to a final concentration of 200 mg/ml. Thirty minutes later, 1 ml of culture was pulsed with 50 mCi of trans-[$^{35}$S]-label (ICN, Irvine, Calif.) for 5 minutes. Bacteria were harvested, and whole cell lysates were resuspended in Laemmli buffer for analysis by sodium dodecyl sulfate-polyacrylamide gel electrophoresis on 7.5% acrylamide gels (Laemmli, U. K. 1970. Cleavage of structural proteins during the assembly of the head of bacteriophage T4. Nature (London). 227:680–685.). Autoradiography was performed with Kodak XAR-5 film.

Recombinant DNA methods

DNA ligations, restriction endonuclease digestions, and gel electrophoresis were performed according to standard techniques (Sambrook. J., E. F. Fritsch, and T. Maniatis. 1989. Molecular cloning: a laboratory manual, 2nd ed. Cold Spring Harbor Laboratory, Cold Spring Harbor, N.Y.). Plasmids were introduced into *E. coli* strains by either chemical transformation or electroporation, as described (Dower, W. J., J. F. Miller, and C. W. Ragsdale. 1988. High efficiency transformation of *E. coli* by high voltage electroporation, Nucleic Acids Res. 16:6127–6145. Sambrook J., E. F. Fritsch, and T. Maniatis. 1989. Molecular cloning: a laboratory manual, 2nd ed. Cold Spring Harbor Laboratory, Cold Spring Harbor, N.Y.). Transformation in *H. influenzae* was performed using the MIV method of Herriott et al. (Herriott, R. M., E. M. Meyer, and M. Vogt. 1970. Defined nongrowth media for stage 11 competence in *Haemophilus influenzae*, J. Bacteriol. 101:517–524.).

Adherence assays

Adherence assays were performed with tissue culture cells which were seeded into wells of 24-well tissue culture plates as previously described (St. Geme et al., Infect. Immun. 58:4036–4044(1991)). Adherence was measured after incubating bacteria with epithelial monolayers for 30 minutes as described (St. Geme, J. W. III, S. Falkow, and S. J. Barenkamp. 1993. High-molecular-weightproteins of nontypable *Haemophilus influenzae* mediate attachment to human epithelial cells. Proc. Natl. Acad. Sci. U.S.A. 90:2875–2879.). Tissue culture cells included Chang epithelial cells (Wong-Kilboume derivative, clone 1-5c-4 (human conjunctiva))(ATCC CCL 20.2). KB cells (human oral epidermoid carcinoma) (ATCC CCL 17). HEp-2 cells (human laryngeal epidermoid carcinoma) (ATCC CCL 23). A549 cells (human lung carcinoma) (ATCC CCL 185). Intestine 407 cells (human embryonic intestine) (ATCC CCL 6). HeLa cells (human cervical epitheloid carcinoma) (ATCC CCL 2). ME-1 80 cells (human cervical epidermoid carcinoma) (ATCC HTB 33). HEC-IB cells (human endometrium) (ATCC HTB 113). and CHO-K1 cells (Chinese hamster ovary) (ATCC CCL 61). Chang, KB, Intestine407, HeLa, and HEC-IB cells were maintained in modified Eagle medium with Earle's salts and non-essential amino acids. HEp-2 cells were maintained in Dulbecco's modified Eagle medium. A549 cells and CHO-K1 cells in F12 medium (Ham), and ME-1 80 cells in McCoy5A medium. All media were supplemented with 10% heat-inactivated fetal bovine serum.

Southern analysis

Southern blotting was performed using high stringency conditions as previously described (St. Geme, J. W. III, and S. Falkow. 1991. Loss of capsule expression by *Haemophilus influenzae* type b results in enhanced adherence to and invasion of human cells. Infect. Immun. 59:1325–1333.).

Microscopy

Samples of epithelial cells with associated bacteria were stained with Giemsa stain and examined by light microscopy as described (St. Geme, J. W. III, and S. Falkow, S. 1990. *Haemophilus influenzae* adheres to and enters cultured human epithelial cells. Infect. Immun. 58:4036–4044.).

For negative-staining electron microscopy, bacteria were stained with 0.5% aqueous uranyl acetate (St. Geme, J. W. III, and S. Falkow. 1991. Loss of capsule expression by *Haemophilus influenzae* type b results in enhanced adherence to and invasion of human cells. Infect. Immun. 59:1325–1333.) and examined using a Zeiss 10A microscope.

The previous study indicated that laboratory *E. coli* strains harboring the plasmid pDC400 were capable of efficient attachment to cultured human epithelial cells (St. Geme, J. W. III, and D. Cutter. 1995. Evidence that surface fibrils expressed by *Haemophilus influenzae* type b promote attachment to human epithelial cells. Mol. Microbiol. 15:77–85.). Subcloning studies and transposon mutagenesis indicated that the relevant coding region of pDC400 was present within an 8.3 kb XbaI fragment (St. Geme, J. W. III, and D. Cutter. 1995. Evidence that surface fibrils expressed by *Haemophilus influenzae* type b promote attachment to human epithelial cells. Mol. Microbiol. 15:77–85.) (FIG. 7). To confirm this conclusion, in the present study this XbaI fragment was subcloned into pT7-7, generating plasmids designated pDC601 and pDC602, which contained the insert in opposite orientations (FIG. 7). As predicted, expression of these plasmids in *E. coli* DH5α was associated with a capacity for high level in vitro attachment (Table 1).

TABLE 1

Adherence to Chang conjunctival cells.

| Strain | ADHERENCE (% inoculum)[a] |
|---|---|
| DH5α/pT7-7 | 0.4 ± 0.1 |
| DH5α/pDC400 | 25.3 ± 1.2 |
| DH5α/pDC601 | 54.3 ± 7.5 |
| DH5α/pDC602 | 55.5 ± 4.3 |
| C54b$^-$p$^-$ | 98.7 ± 9.5 |
| C54-HA1::kan[b] | 1.5 ± 0.2 |
| C54-Tn400.23[c] | 3.3 ± 0.4 |

[a]Adherence was measured in a 30 minute assay and was calculated by dividing the number of adherent bacteria by the number of inoculated bacteria. Values are the mean ± SEM of measurements made in triplicate from representative experiments.
[b]Strain C54-HA1::kan was constructed by transforming C54b$^-$p$^-$ with linearized pHMW8-6, which contains the HA1 gene with an intragenic kanamycin cassette.
[c]Strain C54-Tn400.23 contains a mini-Tn10 kan element in the hsf locus (St. Geme et al., Mol. Microbiol. 15:77–85 (1995)).

To determine the direction of transcription and identify plasmid-encoded proteins, pDC601 and pDC602 were subsequently introduced into *E. coli* BL21(DE3), producing BL21(DE3)/pDC601 and BL21(DE3)/pDC602, respectively. As a negative control, pT7-7 was also transformed into BL21 (DE3). The T7 promoter in these three strains was induced with IPTG, and induced proteins were detected using trans-[$^{35}$S]-label. As shown in FIG. 8, induction of BL21 (DE3)/pDC601 resulted in expression of a large protein over 200 kDa in size along with several slightly smaller proteins, which presumably represent degradation products. In contrast, when BL21(DE3)/pDC602 and BL21(DE3)/pT7-7 were induced, there was no expression of these proteins. This experiment indicated that the genetic material contained in the 8.3 kb XbaI fragment is transcribed from left to right as shown in FIG. 7 and suggested that a single long open reading frame may be present.

Nucleotide sequencing

Nucleotide sequence was determined using a Sequenase kit and double-stranded plasmid template. DNA fragments were subcloned into pUC 19 and sequenced along both strands by primer walking. DNA sequence analysis was performed using the Genetics Computer Group (GCG) software package from the University of Wisconsin (Devereux, J., P. Haeberli, and O. Smithies. 1984. A comprehensive set of sequence analysis programs for the VAX. Nucleic Acids Res. 12:387–395.). Sequence similarity searches were carried out using the BLAST program of the National Center for Biotechnology Information (Altschul. S. F., W. Gish, W. Miller, E. W. Myers, and D. J. Lipman. 1990. Basis local alignment search tool. J. Mol. Biol. 215:403–410.).

Sequencing of the 8.3 kb XbaI fragment revealed a 7059 bp gene, which is designated for literature purposes as hsf for Hae6mophilus surface fibrils, and is referred to herein as HA2. This gene encodes a 2353-amino acid polypeptide, referred to as Hsf or HA2, with a calculated molecular mass of 243.8 kDa, which is similar in size to the observed protein species detected after induction of BL21(DE3)/pDC601. The HA2 gene has a GC content of 42.8%, somewhat greater than the published estimate of 38–39% for the whole genome (Fleischmann et al., 1995. Whole-genomerandom sequencing and assembly of *Haemophilus influenzae* Rd. Science. 269: 496–512., Kilian, M. 1976. A taxonomic study of the genus Haemophilus, with proposal of a new species. J. Gen. Microbiol. 93:9–62.). A putative ribosomal binding site with the sequence AAGGTA begins 13 base pairs upstream of the presumed initiation codon. A sequence similar to a rho-independent transcription terminator is present beginning 20 nucleotides beyond the stop codon and contains interrupted inverted repeats with the potential for forming a hairpin structure containing a loop of two bases and a stem of 11 bases. Of note, a string of 29 thymines spans the region from 149 to 121 nucleotides upstream of HA2.

Homology to HA1/HA1

The nontypable *H. influenzae* nonpilus protein HA1 protein (called Hia in the literature) promotes attachment to cultured human epithelial cells as outlined above. Comparison of the predicted amino acid sequence of HA2 and the sequence of HA1 revealed 81% similarity and 72% identity overall. As depicted in FIG. 5, the two sequences are highly conserved at their N-terminal and C-terminal ends, and both contain a Walker box nucleotide-bindingmotif. Interestingly. HA1 is encoded by a 3.2 kb gene and is only 115-kDa. In this context, it is noteworthy that three separate stretches of HA2 (corresponding to amino acids 174 to 608.847 to 1291, and 1476 to 1914, respectively) show significant homology to the region of HA1 defined by amino acids 221 to 658 (FIG. 5). Table 2 summarizes the level of similarity and identity between these three stretches of HA2 and one another. The suggestion is that the larger size of HA2 may relate in part to the presence of a repeated domain which is present in single copy in HA1.

TABLE 2

Percent similarity and percent identity between HA2 repeats.

| | Percent Similarity/Percent Identity | | |
|---|---|---|---|
| | HA2 174–608[a] | HA2 847–1291[a] | HA2 1476–1914[a] |
| HA2 174–608 | * | 65/53 | 76/60 |
| HA2 847–1291 | | * | 70/56 |
| HA2 1476–1914 | | | * |

[a]Numbers correspond to amino acid residue positions in the full-length HA2 (Hsf) protein.

To evaluate whether HA1 and HA2 are alleles of the same locus, a series of Southern blots were performed. Samples of chromosomal DNA from strains C54 and 11 were subjected to digestion with BglII, ClaI and either PstI or XbaI. Resulting DNA fragments were separated by agarose electrophoresis and transferred bidirectionally to nitrocellulose membranes. One membrane was probed with a 3.3 kb internal fragment of the HA2 gene (FIG. 7), and the other membrane was probed with a 1.6 kb intragenic fragment of the HA1 gene. As shown in FIG. 9, both probes recognized exactly the same chromosomal fragments.

To obtain additional evidence that the HA2 and HA1 genes are homologs, the inactivation of HA2 by transformation of *H. influenzae* strain C54 bp with insertionally inactivated HA1 was attempted. The plasmid pHMW8-6 (Barenkamp, S. J., and J. W. St. Geme, III. Identification of a second family of high molecular weight adhesion proteins expressed by nontypable *Haemophilus influenzae*. Mol. Microbiol., in press.), which contains the H.A1 gene with an intragenic kanamycin cassette, was linearized with NdeI and introduced into competent C54. Southern hybridization confirmed insertion of the kanamycin cassette into HA2 (not shown). Furthermore, examination of the C54 mutant by negative staining transmission electron microscopy revealed the loss of surface fibrils (not shown). Consistent with these findings, the mutant strain demonstrated minimal attachment to Chang conjunctival cells (Table 1).

In additional experiments, the cellular binding specificities conferred by the HA2 and HA1 proteins were compared. As shown in FIG. 10, DH5α/pDC601 (expressing HA2) demonstrated high level attachment to Chang cells, KB cells. HeLa cells, and Intestine 407 cells, moderate level attachment to HEp-2 cells, and minimal attachment to HEC-IB cells, ME-180 cells, and CHO-K1 cells. DH5α harboring pHMW8-5 (expressing HA1) showed virtually the same pattern of attachment. Giemsa staining and subsequent examination by light microscopy confirmed these viable count adherence assay results.

Homology to other bacterial extracellular proteins

A protein sequence similarity search was performed with the HA2 predicted amino acid sequence using the BLAST network service of the National Center for Biotechnology Information (Altschul, S. F., W. Gish, W. Miller, E. W. Myers, and D. J. Lipman. 1990. Basis local alignment search tool. J. Mol. Biol. 215:403–410.). This search revealed low-level sequence similarity to a series of other bacterial adherence factors, including HMW1 and HMW2 (the proteins previously identified as being important adhesins in HA1-deficient nontypable *H. influenzae* strains; (St. Geme, J. W. III, S. Falkow, and S. J. Barenkamp. 1993. High-molecular-weight proteins of nontypable *Haemophilus influenzae* mediate attachment to human epithelial cells. Proc. Natl. Acad. Sci. U.S.A. 90:2875–2879.). AIDA-I (an adhesion protein expressed by some diarrheagenic *E. coli* strains: Benz, I., and M. A. Schmidt. 1992. AIDA-I, the adhesin involved in diffuse adherence of the diarrhoeagenic *Escherichia coli*; strain 2787 (O126:H27), is synthesized via a precursor molecule. Mol. Microbiol. 6:1539–1546.), and Tsh (a hemagglutinin produced by an avian pathogenic *E. coli* strain: Provence, D, and R. Curtiss III. 1994. Isolation and characterization of a gene involved in hemagglutination by an avian pathogenic *Escherichia coli* strain. Infect. Immun. 62:1369–1380.). In addition, HA2 showed homology to SepA, a *Shigella flexneri* secreted protein that appears to play a role in tissue invasion (Benjelloun-Touimi, Z., P. J. Sansonetti, and C. Parsot. 1995. SepA, the major extracellular protein of *Shigelia flexneri*: autonomous secretion and involvement in tissue invasion. Mol. Microbiol. 17:123–135.). Alignment of HA2 with HMW1, HMW2, AIDA-I, Tsh, and SepA revealed a highly conserved N-terminal domain (FIG. 11). In AIDA-I, Tsh, and SepA, this N-terminal extremity precedes a typical procaryotic signal sequence (Benjelloun-Touimi, Z., P. J. Sansonetti, and C. Parsot. 1995. SepA, the major extracellular protein of *Shigelia flexneri*: autonomous secretion and involvement in tissue invasion. Mol. Microbiol. 17:123–135.). Similarly in HA2 this conserved domain precedes a 26 amino acid segment that is characterized by a positively charged region, followed by a string of hydrophobic residues, and then alanine-glutamine-alanine.

Presence of an HA2 homolog in other encapsulated and nonencapsulated strains

Previous work demonstrated that an HA2 homolog is present in *H. influenzae* type b strains M42 and Eagan (St. Geme, J. W. III, and D. Cutter. 1995. Evidence that surface fibrils expressed by *Haemophilus influenzae* type b promote attachment to human epithelial cells. Mol. Microbiol. 15:77–85.). To define the extent to which the HA2 locus is shared by other type b strains, a panel of evolutionarily diverse type b isolates by Southern analysis were examined. Among these strains were six belonging to phylogenic division I and four belonging to phylogenic division II (Musser, J. M., J. S. Kroll, E. R. Moxon, and R. K. Selander. 1988. Evolutionary genetics of the encapsulated strains of *Haemophilus influenzae*. Proc. Natl. Acad. Sci. U.S.A. 85:7758–7762.). Chromosomal DNA was digested with BglII and then probed with the intragenic 3.3 kb fragment of the HA2 gene. As shown in FIG. 12, all 10 strains showed hybridization. The universal presence among *H. influenzae* type b raised the question of the prevalence of this locus in other non-type b encapsulated *H. influenzae*. Southern analysis of a series of type a, c, d, e, and f isolates again demonstrated a homolog in all cases (FIG. 13).

Recently Fleischmann et al. (Fleischmann R. D., et al., 1995. Whole-genomerandom sequencing and assembly of *Haemophilus influenzae* Rd. Science. 269: 496–512.) reported the genome sequence of *H. influenzae* strain Rd, a protein with a predicted amino acid sequence that is 61% similar and 33% identical at its C-terminal end to exoribonuclease II. Of note, the Rd HA2 homolog is also flanked upstream by the exoribonuclease II locus.

EXAMPLE 3

Cloning of HA3

Recombinant phage containing the nontypable Haemophilus strain 32 HA3 gen were isolated and characterized using methods modified slightly from those described previously (Barenkamp and St. Geme. Molecular Microbiology 1996, in press). In brief, chromosomal DNA from strain 32 was prepared by a modification of the method of Marmur (Marmur, 1961). Sau3A partial restriction digests of the DNA were prepared fractionated on 0.7% agarose gels. Fractions containing DNA fragments in the 9- to 20-kbp range were pooled, and a library was prepared by ligation into λEMBL3 arms. Ligation mixtures were packaged in vitro with Gigapack® (Stratagene, La Jolla, Calif.) and plate amplified in a P2 lysogen of *E. coli* LE392.

Lambda plaque screening was performed using a mixture of three PCR products derived from strain 32 chromosomal DNA. These PCR products were amplified using primer pairs previously shown to amplify DNA segments at the 5' end of the strain 11 HA1 gene. The primers were as follows:

| Primer designation | strand | sequence |
| --- | --- | --- |
| 44P | positive | CCG TGC TTG CCC AAC ACG CTT (SEQ ID NO:16) |
| 64P | positive | GCT GCC ACC TTG CAC AAC AAC (SEQ ID NO:17) |
| 93G-2 | positive | CTT TCA ATG CCA GAA AGT AGG (SEQ ID NO:18) |
| 18T-1 | negative | CTT CAA CCG TTG CGG ACA ACA (SEQ ID NO:19) | which was one of the two serotype d strains examined by Southern analysis. In accord with the Southern blotting results, search of the Rd genome revealed an open reading frame with striking sequence similarity to HA2. The Rd gene is 894 nucleotides in length and is predicted to encode a protein of 298 amino acids. Overall, the Rd locus is 70% identical to the C54 HA2 gene, and the Rd derived amino acid sequence is 62% identical and 75% similar to C54 HA2. Interestingly, the Rd open reading frame appears to be truncated due to a "premature" stop codon.

Previous experiments revealed that 13 of 15 nontypable strains lacking an HMW1/HMW2-related protein had evidence of an HA1 homolog (Barenkamp, S. J., and J. W. St. Geme, III. Identification of a second family of high molecular weight adhesion proteins expressed by nontypable *Haemophilus influenzae*. Mol. Microbiol., in press.). Consistent with the demonstration that HA2 and HA1 are homologous, Southern analysis of these 15 strains, probing with the 3.3 kb fragment of hsf, demonstrated hybridization in 12 of the same 13 (not shown).

Chromosomal location of the HA2 locus

In earlier work, the HA1 locus in nontypable strain II was found to be flanked upstream by an open reading frame with significant homology to *E. coli* exoribonuclease II (Barenkamp, S. J., and J. W. St. Geme, III. Identification of a second family of high molecular weight adhesion proteins expressed by nontypable *Haemophilus influenzae*. Mol. Microbiol., in press.). Similarly, the HA2 locus in strain C54 likewise is flanked on the 5' side by an open reading frame with similarity to *E. coli* exonuclease II. This gene terminates 357 base pairs before the HA2 start codon and encodes Each of the positive strand primers was used with the single negative strand primer to generate the three fragments used for probing the library.

The PCR products generated from strain 11 and strain 32 chromosomal DNA were identical in size, suggesting that the nucleotide sequences of these chromosomal regions were similar in the two strains. Plaque screening was performed using standard methodology (Berger and Kimmel, 1987) at high stringency: final wash conditions were 65C for 1 hour in buffer containing 2×SSC and 1% SDS. Positive plaques were identified by autoradiography, plaque purified and phage DNA was purified by standard methods. The same primer pairs used to generate the screening probes were then used to localize the HA3 gene by amplifying various restriction fragments derived from the phage DNA. Once localized, the strain 32 HA3 gene and flanking DNA were sequenced using standard methods.

In order to construct strain 32 isogenic *Haemophilus influenzae* mutants deficient in expression of the HA3 gene, bacteria were made competent using the MIV (Herriott et al. 1970) and were transformed with linearized pHMW8-6, selecting for kanamycin resistance. Allelic exchange was confirmed by Southern analysis. The mutants that no longer expressed HA3 exhibited a marked decrease in binding to Chang epithelial cells, using the methods outlined above (data not shown).

Expression in non-adherent strains of *E. coli* did not result in adherence, although it has not been confirmed that the protein was actually expressed.

We claim:

1. A recombinant nucleic acid encoding a Haemophilus adhesion protein, having greater than 90% identity to a sequence selected from the group consisting of the sequence shown in (SEQ ID NO:2), (SEQ ID NO:4) and (SEQ ID NO:15).

2. The nucleic acid according to claim 1, wherein said Haemophilus adhesion protein has greater than 90% identity to the sequence shown in (SEQ ID NO:2).

3. The nucleic acid according to claim 1 wherein said Haemophilus adhesion protein has greater than 90% identity the sequence shown in (SEQ ID NO:4).

4. The nucleic acid according to claim 1 wherein said Haemophilus adhesion protein has greater than 90% identity to the sequence shown in (SEQ ID NO:15).

5. The nucleic acid of claim 1 comprising DNA having the sequence shown in (SEQ ID NO:14).

6. An expression vector comprising transcriptional and translational regulatory nucleic acid operably linked to the nucleic acid according to claim 1, claim 2, claim 3, claim 4 or claim 5.

7. A host cell transformed with an expression vector according to claim 6.

8. A method of producing an Haemophilus adhesion protein comprising:

a) culturing a host cell according to claim 4 and b) expressing said nucleic acid to produce polypeptide.

* * * * *

UNITED STATES PATENT AND TRADEMARK OFFICE
CERTIFICATE OF CORRECTION

PATENT NO. : 6,759,213 B1
DATED : July 6, 2004
INVENTOR(S) : St. Geme et al.

It is certified that error appears in the above-identified patent and that said Letters Patent is hereby corrected as shown below:

Title page,
Item [73], Assignee, after "Washington University, St. Louis, MO (US)" insert
-- Saint Louis University, St. Louis, MO (US) --

Signed and Sealed this

Twenty-eighth Day of December, 2004

JON W. DUDAS
*Director of the United States Patent and Trademark Office*